United States Patent
Bhalla et al.

(10) Patent No.: US 9,273,336 B2
(45) Date of Patent: Mar. 1, 2016

(54) RECOMBINANT HOST CELLS HAVING AN INCREASE IN BUOYANT DENSITY

(75) Inventors: Ritu Bhalla, New Delhi (IN); Qi Chen, Wallingford, PA (US); Qiong Cheng, Wilmington, DE (US); Neeraj Pandey, Haryana (IN); Pierre E. Rouviere, Wilmington, DE (US); Kristin Ruebling-Jass, Wilmington, DE (US); Annapurna Sachan, Kanpur (IN)

(73) Assignee: E. I. du Pont de Nemours and Company, Wilmington, DE (US)

( * ) Notice: Subject to any disclaimer, the term of this patent is extended or adjusted under 35 U.S.C. 154(b) by 628 days.

(21) Appl. No.: 13/164,990

(22) Filed: Jun. 21, 2011

(65) Prior Publication Data
US 2012/0214202 A1  Aug. 23, 2012

(30) Foreign Application Priority Data
Feb. 21, 2011  (IN) .............................. 441/DEL/2011

(51) Int. Cl.
| C12P 21/06 | (2006.01) |
| C12P 21/02 | (2006.01) |
| C12N 1/02 | (2006.01) |
| C12N 9/10 | (2006.01) |
| C12N 15/70 | (2006.01) |

(52) U.S. Cl.
CPC . *C12P 21/02* (2013.01); *C12N 1/02* (2013.01); *C12N 9/1025* (2013.01); *C12N 15/70* (2013.01)

(58) Field of Classification Search
USPC ....................................................... 435/69.1
See application file for complete search history.

(56) References Cited

U.S. PATENT DOCUMENTS

| 4,480,038 A | 10/1984 | Cheng |
| 4,748,234 A | 5/1988 | Dorin et al. |
| 5,565,350 A | 10/1996 | Kmiec |
| 6,620,419 B1 | 9/2003 | Lintner |
| 6,696,089 B2 | 2/2004 | Kabanov et al. |
| 6,815,426 B2 | 11/2004 | Scialdone et al. |
| 7,129,326 B2 | 10/2006 | Janssen et al. |
| 7,220,405 B2 | 5/2007 | Huang et al. |
| 7,276,088 B2 | 10/2007 | Huang et al. |
| 7,285,264 B2 | 10/2007 | Obrien et al. |
| 7,309,482 B2 | 12/2007 | Buse-Williams et al. |
| 7,341,604 B2 | 3/2008 | Rothe et al. |
| 7,427,656 B2 | 9/2008 | Decarolis et al. |
| 7,585,495 B2 | 9/2009 | Obrien et al. |
| 7,632,919 B2 | 12/2009 | Cunningham et al. |
| 7,662,587 B1 | 2/2010 | Cheng et al. |
| 7,662,913 B2 | 2/2010 | Decarolis et al. |
| 7,678,883 B2 | 3/2010 | Cheng et al. |
| 7,700,716 B2 | 4/2010 | Cunningham et al. |
| 7,709,601 B2 | 5/2010 | Cunningham et al. |
| 7,732,569 B2 | 6/2010 | Decarolis et al. |
| 7,736,633 B2 | 6/2010 | Beck et al. |
| 7,749,957 B2 | 7/2010 | Ittel et al. |
| 7,754,680 B2 | 7/2010 | Cunningham et al. |
| 7,794,963 B2 | 9/2010 | Cheng et al. |
| 7,795,382 B2 | 9/2010 | Decarolis et al. |
| 7,858,581 B2 | 12/2010 | Cunningham et al. |
| 7,906,617 B2 | 3/2011 | Cunningham et al. |
| 7,928,076 B2 | 4/2011 | Cunningham et al. |
| 7,951,559 B2 | 5/2011 | Cheng et al. |
| 2002/0098524 A1 | 7/2002 | Murray et al. |
| 2003/0152976 A1 | 8/2003 | Janssen et al. |
| 2003/0185870 A1 | 10/2003 | Grinstaff et al. |
| 2005/0054752 A1 | 3/2005 | Obrien et al. |
| 2005/0112692 A1 | 5/2005 | Murray et al. |
| 2005/0226839 A1 | 10/2005 | Huang et al. |
| 2006/0171885 A1 | 8/2006 | Janssen et al. |
| 2006/0199206 A1 | 9/2006 | Wang et al. |
| 2007/0065387 A1 | 3/2007 | Beck et al. |
| 2007/0110686 A1 | 5/2007 | Lowe et al. |
| 2007/0196395 A1 | 8/2007 | Huang et al. |
| 2008/0107614 A1 | 5/2008 | Fahnestock et al. |
| 2008/0175798 A1 | 7/2008 | Beck et al. |
| 2008/0280810 A1 | 11/2008 | Obrien et al. |
| 2010/0227361 A1 | 9/2010 | Chen et al. |

FOREIGN PATENT DOCUMENTS

| WO | 0179479 | 10/2001 |
| WO | 2004048399 | 6/2004 |

OTHER PUBLICATIONS

Pandey et al.; Screening and identification of genetic loci involved in producing more/denser inclusion bodies in *Escherichia coli*; Microbial Cell Factories; (2013); vol. 12; vol. 43; pp. 1-12.*
Wang et al.; Abnormal proteins can form aggresome in yeast: aggresome-targeting signals and components of the machinery; The FASEB Journal; vol. 23; pp. 451-463; Feb. 2009.*
Human Growth Hormone; growth hormone 1 isoform 1; NCBI reference sequence NP_000506.2; pp. 1-3, available Dec. 21, 2008.*
Lilie et al.; Advances in refolding of proteins produced in *E. coli*; Current Opinion in Biotechnology; vol. 8, pp. 497-501 (1998).*

(Continued)

*Primary Examiner* — Antonio Galisteo Gonzalez
(74) *Attorney, Agent, or Firm* — E. I. du Pont de Nemours and Company

(57) ABSTRACT

Methods are provided to obtain recombinant microbial cells having at least one genetic modification that increase the buoyant density of a recombinant microbial cell or the buoyant density of inclusion bodies produced within a recombinant microbial cell. Exemplified are genetic modifications that increase the buoyant density of a recombinant microbial cell expressing heterologous peptides and polypeptides. Increasing expression of the genes ysaB, glyQ, glyS or a combination thereof within the recombinant microbial cell produces cells or inclusion bodies having higher buoyant density. A similar effect was achieved by decreasing or disrupting expression of the endogenous gltA gene. Increases in buoyant density render peptide production more efficient with respect to time and costs.

21 Claims, 9 Drawing Sheets

(56) References Cited

OTHER PUBLICATIONS

Machida et al.; Overproduction of L-glucosidase in active form by an *Escherichia coli* system coexpressing the chaperonin GroEL/ES; FEMS Microbiology Letters, vol. 159, pp. 41-46 (1998).*
Chen et al., Biotech Bioengin., 85:463 (2004).
Baba et al., Mol. Syst. Biol., 2:Article 2006.0008 (2006).
Chang et al., Nature, 275:615 (1978).
Goeddel et al., Nature, 281:544 (1979).
Guzman et al., J. Bacteriol. 174:7716 (1992).
Goeddel et al., Nucleic Acids Research, 8:4057 (1980).
De Boer et al., Proc. Natl. Acad. Sci. USA, 80:21 (1983).
Hamilton et al., J. Bacteriol., 171:4617 (1989).
Balbas et al., Gene, 136:211 (1993).
Gueldener et al., Nucleic Acids Research, 24:2519 (1996).
Deshpande, M., Appl. Biochem. Biotechnol., 26:227 (1992).
Talanian et al., J. Biol. Chem., 272:9677 (1997).

* cited by examiner

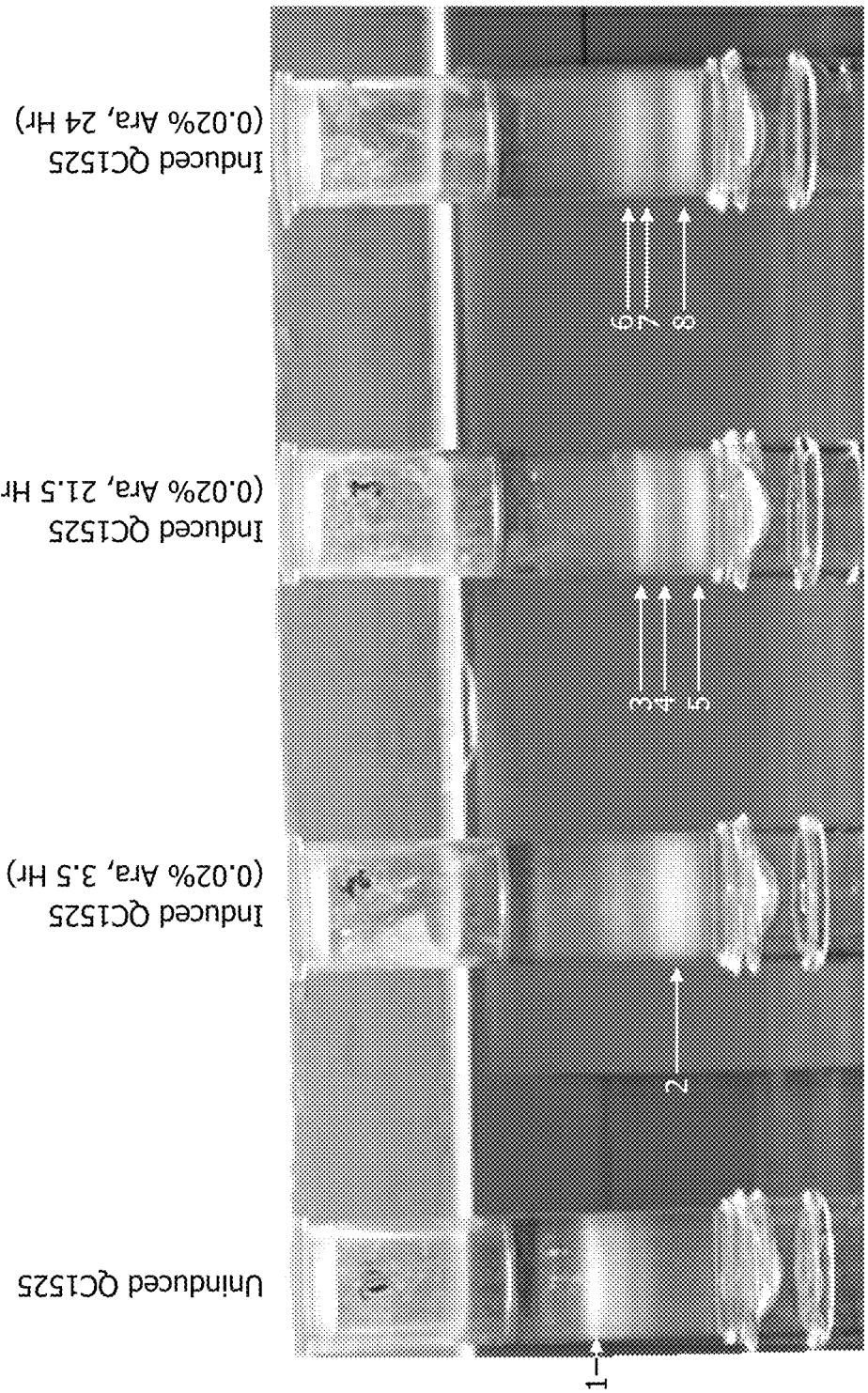

FIG. 8

| Isolates | BW | F1 | B3 | C6 | F1 | A12 | B11 | D2 | E4 |
|---|---|---|---|---|---|---|---|---|---|
| WC | | | | | | | | | |
| IB | | | | | | | | | |

```
SEQUENCE LISTING

<160> NUMBER OF SEQ ID NOS: 165

<210> SEQ ID NO 1
<211> LENGTH: 12
<212> TYPE: PRT
<213> ORGANISM: artificial sequence
<220> FEATURE:
<223> OTHER INFORMATION: Hair-binding peptide

<400> SEQUENCE: 1

Arg Val Pro Asn Lys Thr Val Thr Val Asp Gly Ala
1               5                   10

<210> SEQ ID NO 2
<211> LENGTH: 12
<212> TYPE: PRT
<213> ORGANISM: artificial sequence
<220> FEATURE:
<223> OTHER INFORMATION: Hair-binding peptide

<400> SEQUENCE: 2

Asp Arg His Lys Ser Lys Tyr Ser Ser Thr Lys Ser
1               5                   10

<210> SEQ ID NO 3
<211> LENGTH: 12
<212> TYPE: PRT
<213> ORGANISM: artificial sequence
<220> FEATURE:
<223> OTHER INFORMATION: Hair-binding peptide

<400> SEQUENCE: 3

Lys Asn Phe Pro Gln Gln Lys Glu Phe Pro Leu Ser
1               5                   10

<210> SEQ ID NO 4
<211> LENGTH: 12
<212> TYPE: PRT
<213> ORGANISM: artificial sequence
<220> FEATURE:
<223> OTHER INFORMATION: Hair-binding peptide

<400> SEQUENCE: 4

Gln Arg Asn Ser Pro Pro Ala Met Ser Arg Arg Asp
1               5                   10

<210> SEQ ID NO 5
<211> LENGTH: 12
<212> TYPE: PRT
<213> ORGANISM: artificial sequence
<220> FEATURE:
<223> OTHER INFORMATION: Hair-binding peptide

<400> SEQUENCE: 5

Thr Arg Lys Pro Asn Met Pro His Gly Gln Tyr Leu
1               5                   10

<210> SEQ ID NO 6
<211> LENGTH: 12
```

```
<212> TYPE: PRT
<213> ORGANISM: artificial sequence
<220> FEATURE:
<223> OTHER INFORMATION: Hair-binding peptide

<400> SEQUENCE: 6

Lys Pro Pro His Leu Ala Lys Leu Pro Phe Thr Thr
1               5                   10

<210> SEQ ID NO 7
<211> LENGTH: 12
<212> TYPE: PRT
<213> ORGANISM: artificial sequence
<220> FEATURE:
<223> OTHER INFORMATION: Hair-binding peptide

<400> SEQUENCE: 7

Asn Lys Arg Pro Pro Thr Ser His Arg Ile His Ala
1               5                   10

<210> SEQ ID NO 8
<211> LENGTH: 12
<212> TYPE: PRT
<213> ORGANISM: artificial sequence
<220> FEATURE:
<223> OTHER INFORMATION: Hair-binding peptide

<400> SEQUENCE: 8

Asn Leu Pro Arg Tyr Gln Pro Pro Cys Lys Pro Leu
1               5                   10

<210> SEQ ID NO 9
<211> LENGTH: 12
<212> TYPE: PRT
<213> ORGANISM: artificial sequence
<220> FEATURE:
<223> OTHER INFORMATION: Hair-binding peptide

<400> SEQUENCE: 9

Arg Pro Pro Trp Lys Lys Pro Ile Pro Pro Ser Glu
1               5                   10

<210> SEQ ID NO 10
<211> LENGTH: 12
<212> TYPE: PRT
<213> ORGANISM: artificial sequence
<220> FEATURE:
<223> OTHER INFORMATION: Hair-binding peptide

<400> SEQUENCE: 10

Arg Gln Arg Pro Lys Asp His Phe Phe Ser Arg Pro
1               5                   10

<210> SEQ ID NO 11
<211> LENGTH: 12
<212> TYPE: PRT
<213> ORGANISM: artificial sequence
<220> FEATURE:
<223> OTHER INFORMATION: Hair-binding peptide
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 11
```

```
Ser Val Pro Asn Lys Xaa Val Thr Val Asp Gly Xaa
1               5                   10
```

<210> SEQ ID NO 12
<211> LENGTH: 13
<212> TYPE: PRT
<213> ORGANISM: artificial sequence
<220> FEATURE:
<223> OTHER INFORMATION: Skin-binding peptide

<400> SEQUENCE: 12

```
Thr Pro Phe His Ser Pro Glu Asn Ala Pro Gly Ser Lys
1               5                   10
```

<210> SEQ ID NO 13
<211> LENGTH: 16
<212> TYPE: PRT
<213> ORGANISM: artificial sequence
<220> FEATURE:
<223> OTHER INFORMATION: Skin-binding peptide

<400> SEQUENCE: 13

```
Thr Pro Phe His Ser Pro Glu Asn Ala Pro Gly Ser Gly Gly Gly Ser
1               5                   10                  15
```

<210> SEQ ID NO 14
<211> LENGTH: 17
<212> TYPE: PRT
<213> ORGANISM: artificial sequence
<220> FEATURE:
<223> OTHER INFORMATION: Skin-binding peptide

<400> SEQUENCE: 14

```
Thr Pro Phe His Ser Pro Glu Asn Ala Pro Gly Ser Gly Gly Gly Ser
1               5                   10                  15

Ser
```

<210> SEQ ID NO 15
<211> LENGTH: 15
<212> TYPE: PRT
<213> ORGANISM: artificial sequence
<220> FEATURE:
<223> OTHER INFORMATION: Skin-binding peptide

<400> SEQUENCE: 15

```
Thr Pro Phe His Ser Pro Glu Asn Ala Pro Gly Ser Gly Gly Gly
1               5                   10                  15
```

<210> SEQ ID NO 16
<211> LENGTH: 7
<212> TYPE: PRT
<213> ORGANISM: artificial sequence
<220> FEATURE:
<223> OTHER INFORMATION: Skin-binding peptide

<400> SEQUENCE: 16

```
Phe Thr Gln Ser Leu Pro Arg
1               5
```

<210> SEQ ID NO 17
<211> LENGTH: 12
<212> TYPE: PRT
<213> ORGANISM: artificial sequence
<220> FEATURE:
<223> OTHER INFORMATION: Skin-binding peptide

```
<400> SEQUENCE: 17

Lys Gln Ala Thr Phe Pro Pro Asn Pro Thr Ala Tyr
1               5                   10

<210> SEQ ID NO 18
<211> LENGTH: 12
<212> TYPE: PRT
<213> ORGANISM: artificial sequence
<220> FEATURE:
<223> OTHER INFORMATION: Skin-binding peptide

<400> SEQUENCE: 18

His Gly His Met Val Ser Thr Ser Gln Leu Ser Ile
1               5                   10

<210> SEQ ID NO 19
<211> LENGTH: 7
<212> TYPE: PRT
<213> ORGANISM: artificial sequence
<220> FEATURE:
<223> OTHER INFORMATION: Skin-binding peptide

<400> SEQUENCE: 19

Leu Ser Pro Ser Arg Met Lys
1               5

<210> SEQ ID NO 20
<211> LENGTH: 7
<212> TYPE: PRT
<213> ORGANISM: artificial sequence
<220> FEATURE:
<223> OTHER INFORMATION: Skin-binding peptide

<400> SEQUENCE: 20

Leu Pro Ile Pro Arg Met Lys
1               5

<210> SEQ ID NO 21
<211> LENGTH: 7
<212> TYPE: PRT
<213> ORGANISM: artificial sequence
<220> FEATURE:
<223> OTHER INFORMATION: Skin-binding peptide

<400> SEQUENCE: 21

His Gln Arg Pro Tyr Leu Thr
1               5

<210> SEQ ID NO 22
<211> LENGTH: 7
<212> TYPE: PRT
<213> ORGANISM: artificial sequence
<220> FEATURE:
<223> OTHER INFORMATION: Skin-binding peptide

<400> SEQUENCE: 22

Phe Pro Pro Leu Leu Arg Leu
1               5

<210> SEQ ID NO 23
<211> LENGTH: 12
<212> TYPE: PRT
<213> ORGANISM: artificial sequence
<220> FEATURE:
<223> OTHER INFORMATION: Nail binding peptide

<400> SEQUENCE: 23
```

Ala Leu Pro Arg Ile Ala Asn Thr Trp Ser Pro Ser
1               5                   10

<210> SEQ ID NO 24
<211> LENGTH: 12
<212> TYPE: PRT
<213> ORGANISM: artificial sequence
<220> FEATURE:
<223> OTHER INFORMATION: Nail binding peptide

<400> SEQUENCE: 24

Tyr Pro Ser Phe Ser Pro Thr Tyr Arg Pro Ala Phe
1               5                   10

<210> SEQ ID NO 25
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 25

Asp Glu Cys Met Glu Pro Leu Asn Ala Ala His Cys Trp Arg
1               5                   10

<210> SEQ ID NO 26
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 26

Asp Glu Cys Met His Gly Ser Asp Val Glu Phe Cys Thr Ser
1               5                   10

<210> SEQ ID NO 27
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 27

Asp Leu Cys Ser Met Gln Met Met Asn Thr Gly Cys His Tyr
1               5                   10

<210> SEQ ID NO 28
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 28

Asp Leu Cys Ser Ser Pro Ser Thr Trp Gly Ser Cys Ile Arg
1               5                   10

<210> SEQ ID NO 29
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 29

Asp Pro Asn Glu Ser Asn Tyr Glu Asn Ala Thr Thr Val Ser Gln Pro
1               5                   10                  15

Thr Arg His Leu
            20

<210> SEQ ID NO 30
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 30

Glu Pro Thr His Pro Thr Met Arg Ala Gln Met His Gln Ser Leu Arg
1               5                   10                  15

Ser Ser Ser Pro
            20

<210> SEQ ID NO 31
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 31

Gly Asn Thr Asp Thr Thr Pro Pro Asn Ala Val Met Glu Pro Thr Val
1               5                   10                  15

Gln His Lys Trp
            20

<210> SEQ ID NO 32
<211> LENGTH: 15
<212> TYPE: PRT
<213> ORGANISM: artificial sequence
<220> FEATURE:
<223> OTHER INFORMATION: Tooth pellicle-binding peptide

<400> SEQUENCE: 32

Asn Gly Pro Asp Met Val Gln Ser Val Gly Lys His Lys Asn Ser
1               5                   10                  15

<210> SEQ ID NO 33
<211> LENGTH: 15
<212> TYPE: PRT
<213> ORGANISM: artificial sequence
<220> FEATURE:
<223> OTHER INFORMATION: Tooth pellicle-binding peptide

<400> SEQUENCE: 33

Asn Gly Pro Glu Val Arg Gln Ile Pro Ala Asn Phe Glu Lys Leu
1               5                   10                  15

<210> SEQ ID NO 34
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 34

Trp Cys Thr Asp Phe Cys Thr Arg Ser Thr Pro Thr Ser Thr Ser Arg
1               5                   10                  15

Ser Thr Thr Ser
            20

```
<210> SEQ ID NO 35
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 35

Ala Pro Pro Leu Lys Thr Tyr Met Gln Glu Arg Glu Leu Thr Met Ser
1               5                   10                  15

Gln Asn Lys Asp
            20

<210> SEQ ID NO 36
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 36

Glu Pro Pro Thr Arg Thr Arg Val Asn Asn His Thr Val Thr Val Gln
1               5                   10                  15

Ala Gln Gln His
            20

<210> SEQ ID NO 37
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 37

Gly Tyr Cys Leu Arg Gly Asp Glu Pro Ala Val Cys Ser Gly
1               5                   10

<210> SEQ ID NO 38
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 38

Leu Ser Ser Lys Asp Phe Gly Val Thr Asn Thr Asp Gln Arg Thr Tyr
1               5                   10                  15

Asp Tyr Thr Thr
            20

<210> SEQ ID NO 39
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 39

Asn Phe Cys Glu Thr Gln Leu Asp Leu Ser Val Cys Thr Val
1               5                   10

<210> SEQ ID NO 40
<211> LENGTH: 14
<212> TYPE: PRT
```

<213> ORGANISM: artificial sequence
<220> FEATURE:
<223> OTHER INFORMATION: Tooth enamel-binding peptide

<400> SEQUENCE: 40

Asn Thr Cys Gln Pro Thr Lys Asn Ala Thr Pro Cys Ser Ala
1               5                   10

<210> SEQ ID NO 41
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 41

Pro Ser Glu Pro Glu Arg Arg Asp Arg Asn Ile Ala Ala Asn Ala Gly
1               5                   10                  15

Arg Phe Asn Thr
            20

<210> SEQ ID NO 42
<211> LENGTH: 18
<212> TYPE: PRT
<213> ORGANISM: artificial sequence
<220> FEATURE:
<223> OTHER INFORMATION: Tooth enamel-binding peptide

<400> SEQUENCE: 42

Thr His Asn Met Ser His Phe Pro Pro Ser Gly His Pro Lys Arg Thr
1               5                   10                  15

Ala Thr

<210> SEQ ID NO 43
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 43

Thr Thr Cys Pro Thr Met Gly Thr Tyr His Val Cys Trp Leu
1               5                   10

<210> SEQ ID NO 44
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 44

Tyr Cys Ala Asp His Thr Pro Asp Pro Ala Asn Pro Asn Lys Ile Cys
1               5                   10                  15

Gly Tyr Ser His
            20

<210> SEQ ID NO 45
<211> LENGTH: 10
<212> TYPE: PRT
<213> ORGANISM: artificial sequence
<220> FEATURE:
<223> OTHER INFORMATION: Antimicrobial peptide

<400> SEQUENCE: 45

Phe Ala Lys Lys Leu Ala Lys Lys Leu Leu
1               5                   10

<210> SEQ ID NO 46
<211> LENGTH: 13
<212> TYPE: PRT
<213> ORGANISM: artificial sequence
<220> FEATURE:
<223> OTHER INFORMATION: Antimicrobial peptide

<400> SEQUENCE: 46

Phe Ala Lys Leu Leu Ala Lys Leu Ala Lys Lys Val Leu
1               5                   10

<210> SEQ ID NO 47
<211> LENGTH: 13
<212> TYPE: PRT
<213> ORGANISM: artificial sequence
<220> FEATURE:
<223> OTHER INFORMATION: Antimicrobial peptide

<400> SEQUENCE: 47

Lys Tyr Lys Lys Ala Leu Lys Lys Leu Ala Lys Leu Leu
1               5                   10

<210> SEQ ID NO 48
<211> LENGTH: 12
<212> TYPE: PRT
<213> ORGANISM: artificial sequence
<220> FEATURE:
<223> OTHER INFORMATION: Antimicrobial peptide

<400> SEQUENCE: 48

Phe Ala Leu Leu Lys Ala Leu Leu Lys Lys Ala Leu
1               5                   10

<210> SEQ ID NO 49
<211> LENGTH: 14
<212> TYPE: PRT
<213> ORGANISM: artificial sequence
<220> FEATURE:
<223> OTHER INFORMATION: Antimicrobial peptide

<400> SEQUENCE: 49

Lys Arg Leu Phe Lys Lys Leu Lys Phe Ser Leu Arg Lys Tyr
1               5                   10

<210> SEQ ID NO 50
<211> LENGTH: 14
<212> TYPE: PRT
<213> ORGANISM: artificial sequence
<220> FEATURE:
<223> OTHER INFORMATION: Antimicrobial peptide

<400> SEQUENCE: 50

Lys Arg Leu Phe Lys Lys Leu Leu Phe Ser Leu Arg Lys Tyr
1               5                   10

<210> SEQ ID NO 51
<211> LENGTH: 14
<212> TYPE: PRT
<213> ORGANISM: artificial sequence
<220> FEATURE:
<223> OTHER INFORMATION: Antimicrobial peptide

<400> SEQUENCE: 51

Leu Leu Leu Phe Leu Leu Lys Lys Arg Lys Lys Arg Lys Tyr

<210> SEQ ID NO 52
<211> LENGTH: 27
<212> TYPE: PRT
<213> ORGANISM: artificial sequence
<220> FEATURE:
<223> OTHER INFORMATION: Clay-binding peptide

<400> SEQUENCE: 52

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 53
<211> LENGTH: 27
<212> TYPE: PRT
<213> ORGANISM: artificial sequence
<220> FEATURE:
<223> OTHER INFORMATION: Clay-binding peptide

<400> SEQUENCE: 53

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 54
<211> LENGTH: 27
<212> TYPE: PRT
<213> ORGANISM: artificial sequence
<220> FEATURE:
<223> OTHER INFORMATION: Clay-binding peptide

<400> SEQUENCE: 54

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 55
<211> LENGTH: 27
<212> TYPE: PRT
<213> ORGANISM: artificial sequence
<220> FEATURE:
<223> OTHER INFORMATION: Clay-binding peptide

<400> SEQUENCE: 55

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 56
<211> LENGTH: 22
<212> TYPE: PRT
<213> ORGANISM: artificial sequence
<220> FEATURE:
<223> OTHER INFORMATION: Clay-binding peptide

<400> SEQUENCE: 56

Val Gly Arg His His Ser Lys Ala Lys Gln Lys Arg Pro His Gly Gly
1               5                   10                  15

```
Lys Gly Gln Asn Lys Asn
            20

<210> SEQ ID NO 57
<211> LENGTH: 22
<212> TYPE: PRT
<213> ORGANISM: artificial sequence
<220> FEATURE:
<223> OTHER INFORMATION: Clay-binding peptide

<400> SEQUENCE: 57

Val Gly Arg His His Pro Lys Ala Lys Gln Lys Arg Pro His Gly Gly
1               5                   10                  15

Lys Gly Gln Asn Lys Asn
            20

<210> SEQ ID NO 58
<211> LENGTH: 17
<212> TYPE: PRT
<213> ORGANISM: artificial sequence
<220> FEATURE:
<223> OTHER INFORMATION: Clay-binding peptide

<400> SEQUENCE: 58

Gly Arg Arg Pro Arg Ala Arg Gly Arg Ser Arg Arg Gly Ser Thr Lys
1               5                   10                  15

Thr

<210> SEQ ID NO 59
<211> LENGTH: 19
<212> TYPE: PRT
<213> ORGANISM: artificial sequence
<220> FEATURE:
<223> OTHER INFORMATION: Clay-binding peptide

<400> SEQUENCE: 59

Leu Gly Val Ile Arg Asn His Val Val Arg Gly Arg Arg His His Gln
1               5                   10                  15

His Val Arg

<210> SEQ ID NO 60
<211> LENGTH: 27
<212> TYPE: PRT
<213> ORGANISM: artificial sequence
<220> FEATURE:
<223> OTHER INFORMATION: Clay-binding peptide

<400> SEQUENCE: 60

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 61
<211> LENGTH: 27
<212> TYPE: PRT
<213> ORGANISM: artificial sequence
<220> FEATURE:
<223> OTHER INFORMATION: Clay-binding peptide

<400> SEQUENCE: 61

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
```

```
            20                  25

<210> SEQ ID NO 62
<211> LENGTH: 27
<212> TYPE: PRT
<213> ORGANISM: artificial sequence
<220> FEATURE:
<223> OTHER INFORMATION: Clay-binding peptide

<400> SEQUENCE: 62

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 63
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 63

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 64
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 64

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 65
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 65

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 66
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 66

Arg Asn Asn Lys Gly Ser Lys Lys Val Asp Asp Lys Arg Arg Lys Thr
1               5                   10                  15
```

Val His Ser Thr Lys Ser Arg Ala Lys Tyr Ser
            20                  25

<210> SEQ ID NO 67
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 67

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 68
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 68

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 69
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 69

Arg Asn Asn Lys Gly Ser Lys Lys Val Asp Asp Lys Arg Arg Lys Ala
1               5                   10                  15

Val His Asn Lys Lys Ser Arg Ala Lys Tyr Ser
            20                  25

<210> SEQ ID NO 70
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 70

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 71
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 71

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 72
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 72

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 73
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 73

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 74
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 74

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 75
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 75

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 76
<211> LENGTH: 12
<212> TYPE: PRT
<213> ORGANISM: Artificial sequence
<220> FEATURE:
<223> OTHER INFORMATION: Polypropylene-binding peptides -continued

```
<400> SEQUENCE: 76

Thr Ser Asp Ile Lys Ser Arg Ser Pro His His Arg
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 77

His Thr Gln Asn Met Arg Met Tyr Glu Pro Trp Phe
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 78

Leu Pro Pro Gly Ser Leu Ala
1               5

<210> SEQ ID NO 79
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 79

Met Pro Ala Val Met Ser Ser Ala Gln Val Pro Arg
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 80

Asn Gln Ser Phe Leu Pro Leu Asp Phe Pro Phe Arg
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 81

Ser Ile Leu Ser Thr Met Ser Pro His Gly Ala Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Polypropylene-binding peptide
```

```
<400> SEQUENCE: 82

Ser Met Lys Tyr Ser His Ser Thr Ala Pro Ala Leu
1               5                   10

<210> SEQ ID NO 83
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 83

Glu Ser Ser Tyr Ser Trp Ser Pro Ala Arg Leu Ser
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 84

Gly Pro Leu Lys Leu Leu His Ala Trp Trp Gln Pro
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 85

Asn Ala Leu Thr Arg Pro Val
1               5

<210> SEQ ID NO 86
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 86

Ser Ala Pro Ser Ser Lys Asn
1               5

<210> SEQ ID NO 87
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 87

Ser Val Ser Val Gly Met Lys Pro Ser Pro Arg Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 88
```

```
Ser Tyr Tyr Ser Leu Pro Pro Ile Phe His Ile Pro
1               5                   10
```

<210> SEQ ID NO 89
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 89

```
Thr Phe Thr Pro Tyr Ser Ile Thr His Ala Leu Leu
1               5                   10
```

<210> SEQ ID NO 90
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 90

```
Thr Met Gly Phe Thr Ala Pro Arg Phe Pro His Tyr
1               5                   10
```

<210> SEQ ID NO 91
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 91

```
Thr Asn Pro Phe Pro Pro Pro Pro Ser Ser Pro Ala
1               5                   10
```

<210> SEQ ID NO 92
<211> LENGTH: 12
<212> TYPE: PRT
<213> ORGANISM: Artificial sequence
<220> FEATURE:
<223> OTHER INFORMATION: Polyethylene-binding peptides

<400> SEQUENCE: 92

```
His Asn Lys Ser Ser Pro Leu Thr Ala Ala Leu Pro
1               5                   10
```

<210> SEQ ID NO 93
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 93

```
Leu Pro Pro Trp Lys His Lys Thr Ser Gly Val Ala
1               5                   10
```

<210> SEQ ID NO 94
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 94

Leu Pro Trp Trp Leu Arg Asp Ser Tyr Leu Leu Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 95

Val Pro Trp Trp Lys His Pro Pro Leu Pro Val Pro
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 96

His His Lys Gln Trp His Asn His Pro His His Ala
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 97

His Ile Phe Ser Ser Trp His Gln Met Trp His Arg
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 98

Trp Pro Ala Trp Lys Thr His Pro Ile Leu Arg Met
1               5                   10

<210> SEQ ID NO 99
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 99

Lys Thr Pro Pro Thr Arg Pro
1               5

<210> SEQ ID NO 100
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 100

Val Ile Asn Pro Asn Leu Asp

```
1               5
```

<210> SEQ ID NO 101
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 101

```
Lys Val Trp Ile Val Ser Thr
1               5
```

<210> SEQ ID NO 102
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 102

```
Ala Glu Pro Val Ala Met Leu
1               5
```

<210> SEQ ID NO 103
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 103

```
Ala Glu Leu Val Ala Met Leu
1               5
```

<210> SEQ ID NO 104
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 104

```
His Ser Leu Arg Leu Asp Trp
1               5
```

<210> SEQ ID NO 105
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 105

```
Thr Ser Thr Ala Ser Pro Thr Met Gln Ser Lys Ile Arg
1               5                   10
```

<210> SEQ ID NO 106
<211> LENGTH: 12
<212> TYPE: PRT
<213> ORGANISM: Artificial sequence
<220> FEATURE:
<223> OTHER INFORMATION: Polystyrene-binding peptide

<400> SEQUENCE: 106

```
Lys Arg Asn His Trp Gln Arg Met His Leu Ser Ala
1               5                   10
```

```
<210> SEQ ID NO 107
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 107

Ser His Ala Thr Pro Pro Gln Gly Leu Gly Pro Gln
1               5                   10

<210> SEQ ID NO 108
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 108

Ala Thr Thr Pro Pro Ser Gly Lys Ala Ala His Ser Ala Ala Arg
1               5                   10                  15

Gln Lys Gly Asn
            20

<210> SEQ ID NO 109
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 109

Asp Thr Ile His Pro Asn Lys Met Lys Ser Pro Ser Ser Pro Leu
1               5                   10                  15

<210> SEQ ID NO 110
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 110

Asn Gly Asn Asn His Thr Asp Ile Pro Asn Arg Ser Ser Tyr Thr Gly
1               5                   10                  15

Gly Ser Phe Ala
            20

<210> SEQ ID NO 111
<211> LENGTH: 15
<212> TYPE: PRT
<213> ORGANISM: ARTIFICIAL SEQUENCE
<220> FEATURE:
<223> OTHER INFORMATION: cellulose  acetate-binding peptide

<400> SEQUENCE: 111

Ser Asp Glu Thr Gly Pro Gln Ile Pro His Arg Arg Pro Thr Trp
1               5                   10                  15

<210> SEQ ID NO 112
<211> LENGTH: 12
<212> TYPE: PRT
<213> ORGANISM: Artificial Sequence
<220> FEATURE:
<223> OTHER INFORMATION: Carbon black Binding Peptide
```

<400> SEQUENCE: 112

Ser Val Ser Val Gly Met Lys Pro Ser Pro Arg Pro
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Carbon black-binding peptide

<400> SEQUENCE: 113

Phe His Glu Asn Trp Pro Ser
1               5

<210> SEQ ID NO 114
<211> LENGTH: 7
<212> TYPE: PRT
<213> ORGANISM: Artificial Sequence
<220> FEATURE:
<223> OTHER INFORMATION: Carbon black Binding Peptide

<400> SEQUENCE: 114

Met Pro Pro Pro Leu Met Gln
1               5

<210> SEQ ID NO 115
<211> LENGTH: 12
<212> TYPE: PRT
<213> ORGANISM: Artificial Sequence
<220> FEATURE:
<223> OTHER INFORMATION: Carbon black Binding Peptide

<400> SEQUENCE: 115

Arg Thr Ala Pro Thr Thr Pro Leu Leu Leu Ser Leu
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Cromophtal yellow binding peptide

<400> SEQUENCE: 116

Pro His Ala Arg Leu Val Gly
1               5

<210> SEQ ID NO 117
<211> LENGTH: 7
<212> TYPE: PRT
<213> ORGANISM: Artificial Sequence
<220> FEATURE:
<223> OTHER INFORMATION: Cromophtal yellow Binding Peptide

<400> SEQUENCE: 117

Asn Ile Pro Tyr His His Pro
1               5

<210> SEQ ID NO 118
<211> LENGTH: 7
<212> TYPE: PRT
<213> ORGANISM: Artificial Sequence
<220> FEATURE:
<223> OTHER INFORMATION: Cromophtal yellow Binding Peptide

```
<400> SEQUENCE: 118

Thr Thr Met Pro Ala Ile Pro
1               5

<210> SEQ ID NO 119
<211> LENGTH: 7
<212> TYPE: PRT
<213> ORGANISM: Artificial Sequence
<220> FEATURE:
<223> OTHER INFORMATION: Cromophtal yellow Binding Peptide

<400> SEQUENCE: 119

His Asn Leu Pro Pro Arg Ser
1               5

<210> SEQ ID NO 120
<211> LENGTH: 12
<212> TYPE: PRT
<213> ORGANISM: Artificial Sequence
<220> FEATURE:
<223> OTHER INFORMATION: Cromophtal yellow Binding Peptide

<400> SEQUENCE: 120

Ala His Lys Thr Gln Met Gly Val Arg Gln Pro Ala
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 121

Tyr Pro Asn Thr Ala Leu Val
1               5

<210> SEQ ID NO 122
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 122

Val Ala Thr Arg Ile Val Ser
1               5

<210> SEQ ID NO 123
<211> LENGTH: 12
<212> TYPE: PRT
<213> ORGANISM: Artificial Sequence
<220> FEATURE:
<223> OTHER INFORMATION: Sunfast Magenta Binding Peptide

<400> SEQUENCE: 123

His Ser Leu Lys Asn Ser Met Leu Thr Val Met Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 124
```

Asn Tyr Pro Thr Gln Ala Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 125

Lys Cys Cys Tyr Ser Val Gly
1               5

<210> SEQ ID NO 126
<211> LENGTH: 22
<212> TYPE: PRT
<213> ORGANISM: Artificial Sequence
<220> FEATURE:
<223> OTHER INFORMATION: synthetic construct

<400> SEQUENCE: 126

Ser Arg Arg Pro Arg Gln Leu Gln Gln Arg Gln Ser Arg Arg Pro Arg
1               5                   10                  15

Gln Leu Gln Gln Arg Gln
            20

<210> SEQ ID NO 127
<211> LENGTH: 16
<212> TYPE: PRT
<213> ORGANISM: Artificial Sequence
<220> FEATURE:
<223> OTHER INFORMATION: synthetic construct

<400> SEQUENCE: 127

Ser Arg Arg Pro Arg Gln Leu Gln Gln Arg Gln His His Gln Gln
1               5                   10                  15

<210> SEQ ID NO 128
<211> LENGTH: 33
<212> TYPE: PRT
<213> ORGANISM: Artificial Sequence
<220> FEATURE:
<223> OTHER INFORMATION: synthetic construct

<400> SEQUENCE: 128

Ser Arg Arg Pro Arg Gln Leu Gln Gln Arg Gln Ser Arg Arg Pro Arg
1               5                   10                  15

Gln Leu Gln Gln Arg Gln Ser Arg Arg Pro Arg Gln Leu Gln Gln Arg
            20                  25                  30

Gln

<210> SEQ ID NO 129
<211> LENGTH: 11
<212> TYPE: PRT
<213> ORGANISM: Artificial Sequence
<220> FEATURE:
<223> OTHER INFORMATION: synthetic construct

<400> SEQUENCE: 129

Ser Arg Arg Pro Arg Gln Leu Gln Gln Arg Gln
1               5                   10

<210> SEQ ID NO 130

```
<211> LENGTH: 37
<212> TYPE: PRT
<213> ORGANISM: Artificial Sequence
<220> FEATURE:
<223> OTHER INFORMATION: synthetic construct

<400> SEQUENCE: 130

Ser Arg Arg Pro Arg Gln Leu Gln Gln Arg Gln Asp Pro Ser Arg Arg
1               5                   10                  15

Pro Arg Gln Leu Gln Gln Arg Gln Asp Pro Ser Arg Arg Pro Arg Gln
            20                  25                  30

Leu Gln Gln Arg Gln
        35

<210> SEQ ID NO 131
<211> LENGTH: 22
<212> TYPE: PRT
<213> ORGANISM: Artificial Sequence
<220> FEATURE:
<223> OTHER INFORMATION: synthetic construct

<400> SEQUENCE: 131

Ser Arg Arg Pro Glu Gln Leu Gln Gln Arg Gln Ser Arg Arg Pro Glu
1               5                   10                  15

Gln Leu Gln Gln Arg Gln
            20

<210> SEQ ID NO 132
<211> LENGTH: 22
<212> TYPE: PRT
<213> ORGANISM: Artificial Sequence
<220> FEATURE:
<223> OTHER INFORMATION: synthetic construct

<400> SEQUENCE: 132

Ser Arg Glu Pro Glu Gln Leu Gln Gln Arg Gln Ser Arg Arg Pro Glu
1               5                   10                  15

Gln Leu Gln Gln Arg Gln
            20

<210> SEQ ID NO 133
<211> LENGTH: 22
<212> TYPE: PRT
<213> ORGANISM: Artificial Sequence
<220> FEATURE:
<223> OTHER INFORMATION: synthetic construct

<400> SEQUENCE: 133

Ser Arg Glu Pro Glu Gln Leu Gln Gln Arg Gln Ser Arg Glu Pro Glu
1               5                   10                  15

Gln Leu Gln Gln Arg Gln
            20

<210> SEQ ID NO 134
<211> LENGTH: 22
<212> TYPE: PRT
<213> ORGANISM: Artificial Sequence
<220> FEATURE:
<223> OTHER INFORMATION: synthetic construct

<400> SEQUENCE: 134

Ser Glu Glu Pro Glu Gln Leu Gln Gln Glu Gln Ser Arg Arg Pro Arg
1               5                   10                  15

Gln Leu Gln Gln Arg Gln
```

20

<210> SEQ ID NO 135
<211> LENGTH: 22
<212> TYPE: PRT
<213> ORGANISM: Artificial Sequence
<220> FEATURE:
<223> OTHER INFORMATION: synthetic construct

<400> SEQUENCE: 135

Ser Arg Glu Pro Glu Gln Leu Gln Gln Glu Gln Ser Arg Glu Pro Glu
1               5                   10                  15

Gln Leu Gln Gln Arg Gln
            20

<210> SEQ ID NO 136
<211> LENGTH: 56
<212> TYPE: PRT
<213> ORGANISM: artificial sequence
<220> FEATURE:
<223> OTHER INFORMATION: synthetic construct

<400> SEQUENCE: 136

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser
    50                  55

<210> SEQ ID NO 137
<211> LENGTH: 50
<212> TYPE: PRT
<213> ORGANISM: artificial sequence
<220> FEATURE:
<223> OTHER INFORMATION: synthetic construct

<400> SEQUENCE: 137

Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Glu Cys Gly Gln Gln Arg Phe Gln Trp Gln Phe Glu Gln Gln Pro Cys
        35                  40                  45

Gly Ser
    50

<210> SEQ ID NO 138
<211> LENGTH: 64
<212> TYPE: PRT
<213> ORGANISM: artificial sequence
<220> FEATURE:
<223> OTHER INFORMATION: synthetic construct

<400> SEQUENCE: 138

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln

```
                35                  40                  45
Trp Gln Phe Glu Gln Gln Gly Ser Cys Cys Pro Gly Cys Cys Gly Ser
         50                  55                  60

<210> SEQ ID NO 139
<211> LENGTH: 63
<212> TYPE: PRT
<213> ORGANISM: artificial sequence
<220> FEATURE:
<223> OTHER INFORMATION: synthetic construct

<400> SEQUENCE: 139

Met Ala Ser Cys Gly Gln Gln Arg Phe Gln Trp Gln Phe Glu Gln Gln
 1               5                  10                  15

Pro Arg Cys Gly Gln Gln Arg Phe Gln Trp Gln Phe Glu Gln Gln Pro
                20                  25                  30

Arg Cys Gly Gln Gln Arg Phe Gln Trp Gln Phe Glu Gln Gln Pro Glu
             35                  40                  45

Cys Gly Gln Gln Arg Phe Gln Trp Gln Phe Glu Gln Gln Pro Cys
         50                  55                  60

<210> SEQ ID NO 140
<211> LENGTH: 6
<212> TYPE: PRT
<213> ORGANISM: artificial sequence
<220> FEATURE:
<223> OTHER INFORMATION: synthetic construct

<400> SEQUENCE: 140

Cys Cys Pro Gly Cys Cys
 1               5

<210> SEQ ID NO 141
<211> LENGTH: 6034
<212> TYPE: DNA
<213> ORGANISM: artificial sequence
<220> FEATURE:
<223> OTHER INFORMATION: Plasmid pLR199

<400> SEQUENCE: 141
```

| | | | | | |
|---|---|---|---|---|---|
| aagaaaccaa | ttgtccatat | tgcatcagac | attgccgtca | ctgcgtcttt | tactggctct | 60 |
| tctcgctaac | caaaccggta | accccgctta | ttaaaagcat | tctgtaacaa | agcgggacca | 120 |
| aagccatgac | aaaaacgcgt | aacaaaagtg | tctataatca | cggcagaaaa | gtccacattg | 180 |
| attatttgca | cggcgtcaca | ctttgctatg | ccatagcatt | tttatccata | agattagcgg | 240 |
| atcttacctg | acgcttttta | tcgcaactct | ctactgtttc | tccatacccg | ttttttgggc | 300 |
| taacaggagg | aattacatat | gcagcagcgt | ttccagtggc | agttcgaaca | gcagccgcgt | 360 |
| ggtcagcagc | gtttccagtg | gcagttcgaa | cagcagccgc | gtggtcagca | gcgtttccag | 420 |
| tggcagttcg | aacagcagcc | ggaaggtcag | cagcgtttcc | agtggcagtt | cgaacagcag | 480 |
| ggatcttgct | gtccgggctg | ttgcggatcc | gaccctggca | ttccgtggtg | gaacattcgt | 540 |
| gctcctctga | atgcaggtgc | gggcatccct | tggtggaata | ttcgtgctcc | gctgaacgcc | 600 |
| ggtggttccg | gtccgggtag | cggtggtaat | acttctcagc | tgtccacggg | tggcggtaac | 660 |
| actagccagc | tgagcacggg | cggccctaaa | agccgggcg | accgggtat | tccgtggtgg | 720 |
| aatatccgtg | ccccgctgaa | cgcaggtgcc | ggcatcccgt | ggtggaacat | tcgtgcacct | 780 |
| ctgaatgctg | gtggttccgg | tccaggctct | ggcggcaaca | cttcccagct | gtccaccggc | 840 |
| ggtggcaaca | ccagccagct | gtctactggt | ggtccgaaga | aaccgggtga | ctaataaggc | 900 |

```
gcgccgaccc agctttcttg tacaaagtgg ttgattcgag gctgctaaca aagcccgaaa    960
ggaagctgag ttggctgctg ccaccgctga gcaataacta gcataacccc ttggggcctc   1020
taaacgggtc ttgaggggtt ttttgctgaa aggaggaact atatccggat atccacagga   1080
cgggtgtggt cgccatgatc gcgtagtcga tagtggctcc aagtagcgaa gcgagcagga   1140
ctgggcggcg gccaaagcgg tcggacagtg ctccgagaac gggtgcgcat agaaattgca   1200
tcaacgcata tagcgctagc agcacgccat agtgactggc gatgctgtcg gaatggacga   1260
tatcccgcaa gaggcccggc agtaccggca taaccaagcc tatgcctaca gcatccaggg   1320
tgacggtgcc gaggatgacg atgagcgcat tgttagattt catacacggt gcctgactgc   1380
gttagcaatt taactgtgat aaactaccgc attaaagctt gcagtggcgg ttttcatggc   1440
ttgttatgac tgttttttg gggtacagtc tatgcctcgg gcatccaagc agcaagcgcg   1500
ttacgccgtg ggtcgatgtt tgatgttatg gagcagcaac gatgttacgc agcagggcag   1560
tcgccctaaa acaaagttaa acatcatgag ggaagcggtg atcgccgaag tatcgactca   1620
actatcagag gtagttggcg tcatcgagcg ccatctcgaa ccgacgttgc tggccgtaca   1680
tttgtacggc tccgcagtgg atggcggcct gaagccacac agtgatattg atttgctggt   1740
tacggtgacc gtaaggcttg atgaaacaac gcggcgagct ttgatcaacg accttttgga   1800
aacttcggct tcccctggag agagcgagat tctccgcgct gtagaagtca ccattgttgt   1860
gcacgacgac atcattccgt ggcgttatcc agctaagcgc gaactgcaat tggagaatg    1920
gcagcgcaat gacattcttg caggtatctt cgagccagcc acgatcgaca ttgatctggc   1980
tatcttgctg acaaaagcaa gagaacatag cgttgccttg gtaggtccag cggcggagga   2040
actctttgat ccggttcctg aacaggatct atttgaggcg ctaaatgaaa ccttaacgct   2100
atggaactcg ccgcccgact gggctggcga tgagcgaaat gtagtgctta cgttgtcccg   2160
catttggtac agcgcagtaa ccggcaaaat cgcgccgaag gatgtcgctg ccgactgggc   2220
aatggagcgc ctgccggccc agtatcagcc cgtcatactt gaagctagac aggcttatct   2280
tggacaagaa gaagatcgct tggcctcgcg cgcagatcag ttggaagaat tgtccacta    2340
cgtgaaaggc gagatcacca aggtagtcgg caaataatgt ctaacaattc gttcaagctt   2400
ggctgttttg gcggatgaga gaagattttc agcctgatac agattaaatc agaacgcaga   2460
agcggtctga taaaacagaa tttgcctggc ggcagtagcg cggtggtccc acctgacccc   2520
atgccgaact cagaagtgaa acgccgtagc gccgatggta gtgtggggtc tccccatgcg   2580
agagtaggga actgccaggc atcaaataaa acgaaaggct cagtcgaaag actgggcctt   2640
tcgttttatc tgttgtttgt cggtgaacgc tctcctgagt aggacaaatc cgccgggagc   2700
ggatttgaac gttgcgaagc aacgcccgg agggtggcgg gcaggacgcc cgccataaac    2760
tgccaggcat caaattaagc agaaggccat cctgacggat ggcctttttg cgtttctaca   2820
aactcttttg tttatttttc taaatacatt caaatatgta tccgctcatg agacaataac   2880
cctgataaat gcttcaataa tattgaaaaa ggaagagtat gagtattcaa catttccgtg   2940
tcgcccttat tccctttttt gcggcatttt gccttcctgt ttttgctcac ccagaaacgc   3000
tggtgaaagt aaaagatgct gaagatcagt tgggtgcacg agtgggttac atcgaactgg   3060
atctcaacag cggtaagatc cttgagagtt ttcgccccga agaacgtttt ccaatgatga   3120
gcacttttaa agttctgcta tgtggcgcgg tattatcccg tgttgacgcc gggcaagagc   3180
aactcggtcg ccgcatacac tattctcaga atgacttggt tgagtactca ccagtcacag   3240
```

```
aaaagcatct tacggatggc atgacagtaa gagaattatg cagtgctgcc ataaccatga  3300
gtgataacac tgcggccaac ttacttctga caacgatcgg aggaccgaag gagctaaccg  3360
cttttttgca caacatgggg gatcatgtaa ctcgccttga tcgttgggaa ccggagctga  3420
atgaagccat accaaacgac gagcgtgaca ccacgatgcc tgtagcaatg caacaacgt   3480
tgcgcaaact attaactggc gaactactta ctctagcttc ccggcaacaa ttaatagact  3540
ggatggaggc ggataaagtt gcaggaccac ttctgcgctc ggcccttccg gctggctggt  3600
ttattgctga taaatctgga gccggtgagc gtgggtctcg cggtatcatt gcagcactgg  3660
ggccagatgg taagccctcc cgtatcgtag ttatctacac gacggggagt caggcaacta  3720
tggatgaacg aaatagacag atcgctgaga taggtgcctc actgattaag cattggtaac  3780
tgtcagacca gtttactcat atatactttt agattgattt aaaacttcat ttttaattta  3840
aaaggatcta ggtgaagatc cttttgata atctcatgac caaaatccct taacgtgagt  3900
tttcgttcca ctgagcgtca gaccccgtag aaaagatcaa aggatcttct tgagatcctt  3960
tttttctgcg cgtaatctgc tgcttgcaaa caaaaaaacc accgctacca gcggtggttt  4020
gtttgccgga tcaagagcta ccaactcttt ttccgaaggt aactggcttc agcagagcgc  4080
agataccaaa tactgtcctt ctagtgtagc cgtagttagg ccaccacttc aagaactctg  4140
tagcaccgcc tacatacctc gctctgctaa tcctgttacc agtggctgct gccagtggcg  4200
ataagtcgtg tcttaccggg ttggactcaa gacgatagtt accggataag cgcagcggt   4260
cgggctgaac ggggggttcg tgcacacagc ccagcttgga gcgaacgacc tacaccgaac  4320
tgagatacct acagcgtgag ctatgagaaa gcgccacgct tcccgaaggg agaaaggcgg  4380
acaggtatcc ggtaagcggc agggtcggaa caggagagcg cacgagggag cttccagggg  4440
gaaacgcctg gtatctttat agtcctgtcg ggtttcgcca cctctgactt gagcgtcgat  4500
ttttgtgatg ctcgtcaggg gggcggagcc tatggaaaaa cgccagcaac gcggcctttt  4560
tacggttcct ggccttttgc tggccttttg ctcacatgtt ctttcctgcg ttatcccctg  4620
attctgtgga taaccgtatt accgcctttg agtgagctga taccgctcgc cgcagccgaa  4680
cgaccgagcg cagcgagtca gtgagcgagg aagcggaaga gcgcctgatg cggtatttc   4740
tccttacgca tctgtgcggt atttcacacc gcatatatgg tgcactctca gtacaatctg  4800
ctctgatgcc gcatagttaa gccagtatac actccgctat cgctacgtga ctgggtcatg  4860
gctgcgcccc gacacccgcc aacacccgct gacgcgccct gacgggcttg tctgctcccg  4920
gcatccgctt acagacaagc tgtgaccgtc tccgggagct gcatgtgtca gaggttttca  4980
ccgtcatcac cgaaacgcgc gaggcagcag atcaattcgc gcgcgaaggc gaagcggcat  5040
gcataatgtg cctgtcaaat ggacgaagca gggattctgc aaaccctatg ctactccgtc  5100
aagccgtcaa ttgtctgatt cgttaccaat tatgacaact tgacggctac atcattcact  5160
tttcttcac aaccggcacg gaactcgctc gggctggccc cggtgcattt tttaaatacc   5220
cgcgagaaat agagttgatc gtcaaaacca acattgcgac cgacggtggc gataggcatc  5280
cgggtggtgc tcaaaagcag cttcgcctgg ctgatacgtt ggtcctcgcg ccagcttaag  5340
acgctaatcc ctaactgctg gcggaaaaga tgtgacagac gcgacggcga caagcaaaca  5400
tgctgtgcga cgctggcgat atcaaaattg ctgtctgcca ggtgatcgct gatgtactga  5460
caagcctcgc gtacccgatt atccatcggt ggatggagcg actcgttaat cgcttccatg  5520
cgccgcagta acaattgctc aagcagattt atcgccagca gctccgaata gcgcccttcc  5580
ccttgcccgg cgttaatgat ttgcccaaac aggtcgctga aatgcggctg gtgcgcttca  5640
```

```
tccgggcgaa agaaccccgt attggcaaat attgacggcc agttaagcca ttcatgccag     5700
taggcgcgcg gacgaaagta aacccactgg tgataccatt cgcgagcctc cggatgacga     5760
ccgtagtgat gaatctctcc tggcgggaac agcaaaatat cacccggtcg gcaaacaaat     5820
tctcgtccct gattttcac cacccctga ccgcgaatgg tgagattgag aatataacct      5880
ttcattccca gcggtcggtc gataaaaaaa tcgagataac cgttggcctc aatcggcgtt     5940
aaacccgcca ccagatgggc attaaacgag tatcccggca gcaggggatc attttgcgct    6000
tcagccatac ttttcatact cccgccattc agag                                6034
```

<210> SEQ ID NO 142
<211> LENGTH: 579
<212> TYPE: DNA
<213> ORGANISM: artificial sequence
<220> FEATURE:
<223> OTHER INFORMATION: Synthetic construct

<400> SEQUENCE: 142

```
atgcagcagc gtttccagtg gcagttcgaa cagcagccgc gtggtcagca gcgtttccag      60
tggcagttcg aacagcagcc gcgtggtcag cagcgtttcc agtggcagtt cgaacagcag     120
ccggaaggtc agcagcgttt ccagtggcag ttcgaacagc agggatcttg ctgtccgggc     180
tgttgcggat ccgaccctgg cattccgtgg tggaacattc gtgctcctct gaatgcaggt     240
gcgggcatcc cttggtggaa tattcgtgct ccgctgaacg ccggtggttc cggtccgggt     300
agcggtggta atacttctca gctgtccacg ggtggcggta acactagcca gctgagcacg     360
ggcggcccta aaaagccggg cgacccgggt attccgtggt ggaatatccg tgccccgctg     420
aacgcaggtg ccggcatccc gtggtggaac attcgtgcac ctctgaatgc tggtggttcc     480
ggtccaggct ctggcggcaa cacttcccag ctgtccaccg gcggtggcaa caccagccag     540
ctgtctactg gtggtccgaa gaaaccgggt gactaataa                            579
```

<210> SEQ ID NO 143
<211> LENGTH: 190
<212> TYPE: PRT
<213> ORGANISM: artificial sequence
<220> FEATURE:
<223> OTHER INFORMATION: Synthetic construct

<400> SEQUENCE: 143

```
Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Pro Glu Gly Gln Gln Arg Phe Gln Trp
        35                  40                  45

Gln Phe Glu Gln Gln Gly Ser Cys Cys Pro Gly Cys Cys Gly Ser Asp
    50                  55                  60

Pro Gly Ile Pro Trp Trp Asn Ile Arg Ala Pro Leu Asn Ala Gly Ala
65                  70                  75                  80

Gly Ile Pro Trp Trp Asn Ile Arg Ala Pro Leu Asn Ala Gly Gly Ser
                85                  90                  95

Gly Pro Gly Ser Gly Gly Asn Thr Ser Gln Leu Ser Thr Gly Gly Gly
            100                 105                 110

Asn Thr Ser Gln Leu Ser Thr Gly Gly Pro Lys Lys Pro Gly Asp Pro
        115                 120                 125
```

```
Gly Ile Pro Trp Trp Asn Ile Arg Ala Pro Leu Asn Ala Gly Ala Gly
        130                 135                 140

Ile Pro Trp Trp Asn Ile Arg Ala Pro Leu Asn Ala Gly Gly Ser Gly
145                 150                 155                 160

Pro Gly Ser Gly Gly Asn Thr Ser Gln Leu Ser Thr Gly Gly Asn
                165                 170                 175

Thr Ser Gln Leu Ser Thr Gly Gly Pro Lys Lys Pro Gly Asp
        180                 185                 190

<210> SEQ ID NO 144
<211> LENGTH: 6034
<212> TYPE: DNA
<213> ORGANISM: artificial sequence
<220> FEATURE:
<223> OTHER INFORMATION: Plasmid pDCQ523

<400> SEQUENCE: 144
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcttacctg acgcttttta tcgcaactct ctactgtttc tccatacccg tttttggc    300 taacaggagg aattacatat ggctagctgc ggtcaacaac gttttcaatg caattcgaa    360 caacagccgc gttgcggcca gcaacgcttc caatggcagt ttgaacagca accgcgttgc   420
ggtcagcaac gtttccagtg gcaatttgaa caacagccag agtgcggcca gcagcgcttt   480
cagtggcagt tcgagcagca gccgtgcgga tcttgctgtc cgggctgttg cggatccgat   540
ccatctgctc aatctcaact gcctgataaa cattctggtc tgcatgaacg cgctcctcaa   600
cgttacggtc cggaggaggc ggcgaagaaa gaagaggcgg ctaaaaagcc ggctcacatt   660
aataagacca acccgcatca gggcaaccat cactccgaaa agacccagcg tcagggctcc   720
ggtggcggcg gtagcggcag cggtggcggt ggttctgact cccatcacaa ccatcacaag   780
caggactccc gccctcagca ccgtaagacg ccaaacggcg gtggtgactc tcaccataac   840
caccacaaac aggactctcg cccgcagcac cgcaaaaccc ctaacggtaa ataataaggc   900
gcgccgaccc agctttcttg tacaaagtgg ttgattcgag gctgctaaca aagcccgaaa   960
ggaagctgag ttggctgctg ccaccgctga gcaataacta gcataacccc ttggggcctc  1020
taaacgggtc ttgaggggtt ttttgctgaa aggaggaact atatccggat atccacagga  1080
cgggtgtggt cgccatgatc gcgtagtcga tagtggctcc aagtagcgaa gcgagcagga  1140
ctgggcggcg gccaaagcgg tcggacagtg ctccgagaac gggtgcgcat agaaattgca  1200
tcaacgcata tagcgctagc agcacgccat agtgactggc gatgctgtcg gaatggacga  1260
tatcccgcaa gaggcccggc agtaccggca taaccaagcc tatgcctaca gcatccaggg  1320
tgacggtgcc gaggatgacg atgagcgcat tgttagattt catacacggt gcctgactgc  1380
gttagcaatt taactgtgat aaactaccgc attaaagctt gcagtggcgg ttttcatggc  1440
ttgttatgac tgtttttttg gggtacagtc tatgcctcgg gcatccaagc agcaagcgcg  1500
ttacgccgtg ggtcgatgtt tgatgttatg gagcagcaac gatgttacgc agcagggcag  1560
tcgccctaaa acaaagttaa acatcatgag ggaagcggtg atcgccgaag tatcgactca  1620
actatcagag gtagttggcg tcatcgagcg ccatctcgaa ccgacgttgc tggccgtaca  1680
tttgtacggc tccgcagtgg atggcggcct gaagccacac agtgatattg atttgctggt  1740
```

```
tacggtgacc gtaaggcttg atgaaacaac gcggcgagct ttgatcaacg acctttggga    1800
aacttcggct tccctggag agagcgagat tctccgcgct gtagaagtca ccattgttgt    1860
gcacgacgac atcattccgt ggcgttatcc agctaagcgc gaactgcaat ttggagaatg    1920
gcagcgcaat gacattcttg caggtatctt cgagccagcc acgatcgaca ttgatctggc    1980
tatcttgctg acaaaagcaa gagaacatag cgttgccttg gtaggtccag cggcggagga    2040
actctttgat ccggttcctg aacaggatct atttgaggcg ctaaatgaaa ccttaacgct    2100
atggaactcg ccgcccgact gggctggcga tgagcgaaat gtagtgctta cgttgtcccg    2160
catttggtac agcgcagtaa ccggcaaaat cgcgccgaag gatgtcgctg ccgactgggc    2220
aatggagcgc ctgccggccc agtatcagcc cgtcatactt gaagctagac aggcttatct    2280
tggacaagaa gaagatcgct tggcctcgcg cgcagatcag ttggaagaat ttgtccacta    2340
cgtgaaaggc gagatcacca aggtagtcgg caaataatgt ctaacaattc gttcaagctt    2400
ggctgttttg gcggatgaga gaagattttc agcctgatac agattaaatc agaacgcaga    2460
agcggtctga taaaacagaa tttgcctggc ggcagtagcg cggtggtccc acctgacccc    2520
atgccgaact cagaagtgaa acgccgtagc gccgatggta gtgtgggtc tccccatgcg    2580 agagtaggga actgccaggc atcaaataaa acgaaaggct cagtcgaaag actgggcctt    2640
tcgttttatc tgttgtttgt cggtgaacgc tctcctgagt aggacaaatc cgccgggagc    2700
ggatttgaac gttgcgaagc aacggcccgg agggtggcgg gcaggacgcc cgccataaac    2760
tgccaggcat caaattaagc agaaggccat cctgacggat ggccttttg cgtttctaca    2820 aactcttttg tttattttc taaatacatt caaatatgta tccgctcatg agacaataac    2880
cctgataaat gcttcaataa tattgaaaaa ggaagagtat gagtattcaa catttccgtg    2940
tcgcccttat cccttttttt gcggcatttt gccttcctgt ttttgctcac ccagaaacgc    3000
tggtgaaagt aaaagatgct gaagatcagt tgggtgcacg agtgggttac atcgaactgg    3060
atctcaacag cggtaagatc cttgagagtt ttcgccccga agaacgtttt ccaatgatga    3120
gcacttttaa agttctgcta tgtggcgcgg tattatcccg tgttgacgcc gggcaagagc    3180
aactcggtcg ccgcatacac tattctcaga atgacttggt tgagtactca ccagtcacag    3240
aaaagcatct tacgcgatggc atgacagtaa gagaattatg cagtgctgcc ataaccatga    3300
gtgataacac tgcggccaac ttacttctga caacgatcgg aggaccgaag gagctaaccg    3360
cttttttgca acatgggg gatcatgtaa ctcgccttga tcgttgggaa ccggagctga    3420
atgaagccat accaaacgac gagcgtgaca ccacgatgcc tgtagcaatg gcaacaacgt    3480
tgcgcaaact attaactggc gaactactta ctctagcttc ccggcaacaa ttaatagact    3540
ggatggaggc ggataaagtt gcaggaccac ttctgcgctc ggcccttccg gctggctggt    3600
ttattgctga taaatctgga gccggtgagc gtgggtctcg cggtatcatt gcagcactgg    3660
ggccagatgg taagccctcc cgtatcgtag ttatctacac gacggggagt caggcaacta    3720
tggatgaacg aaatagacag atcgctgaga taggtgcctc actgattaag cattggtaac    3780
tgtcagacca agtttactca tatatacttt agattgattt aaaacttcat ttttaattta    3840
aaaggatcta ggtgaagatc cttttttgata atctcatgac caaaatccct taacgtgagt    3900
tttcgttcca ctgagcgtca gaccccgtag aaaagatcaa aggatcttct tgagatcctt    3960 ttttttctgcg cgtaatctgc tgcttgcaaa caaaaaaacc accgctacca gcggtggttt    4020
gtttgccgga tcaagagcta ccaactcttt ttccgaaggt aactggcttc agcagagcgc    4080
```

```
agataccaaa tactgtcctt ctagtgtagc cgtagttagg ccaccacttc aagaactctg   4140
tagcaccgcc tacatacctc gctctgctaa tcctgttacc agtggctgct gccagtggcg   4200
ataagtcgtg tcttaccggg ttggactcaa gacgatagtt accggataag gcgcagcggt   4260
cgggctgaac ggggggttcg tgcacacagc ccagcttgga gcgaacgacc tacaccgaac   4320
tgagatacct acagcgtgag ctatgagaaa gcgccacgct tcccgaaggg agaaaggcgg   4380
acaggtatcc ggtaagcggc agggtcggaa caggagagcg cacgagggag cttccagggg   4440
gaaacgcctg gtatctttat agtcctgtcg ggtttcgcca cctctgactt gagcgtcgat   4500
ttttgtgatg ctcgtcaggg gggcggagcc tatggaaaaa cgccagcaac gcggcctttt   4560
tacggttcct ggccttttgc tggccttttg ctcacatgtt ctttcctgcg ttatcccctg   4620
attctgtgga taaccgtatt accgcctttg agtgagctga taccgctcgc cgcagccgaa   4680
cgaccgagcg cagcgagtca gtgagcgagg aagcggaaga gcgcctgatg cggtattttc   4740
tccttacgca tctgtgcggt atttcacacc gcatatatgg tgcactctca gtacaatctg   4800
ctctgatgcc gcatagttaa gccagtatac actccgctat cgctacgtga ctgggtcatg   4860
gctgcgcccc gacacccgcc aacacccgct gacgcgccct gacgggcttg tctgctcccg   4920
gcatccgctt acagacaagc tgtgaccgtc tccgggagct gcatgtgtca gaggttttca   4980
ccgtcatcac cgaaacgcgc gaggcagcag atcaattcgc gcgcgaaggc gaagcggcat   5040
gcataatgtg cctgtcaaat ggacgaagca gggattctgc aaaccctatg ctactccgtc   5100
aagccgtcaa ttgtctgatt cgttaccaat tatgacaact tgacggctac atcattcact   5160
ttttcttcac aaccggcacg gaactcgctc gggctggccc cggtgcattt tttaaatacc   5220
cgcgagaaat agagttgatc gtcaaaacca acattgcgac cgacggtggc gataggcatc   5280
cgggtggtgc tcaaaagcag cttcgcctgg ctgatacgtt ggtcctcgcg ccagcttaag   5340
acgctaatcc ctaactgctg gcggaaaaga tgtgacagac gcgacggcga caagcaaaca   5400
tgctgtgcga cgctggcgat atcaaaattg ctgtctgcca ggtgatcgct gatgtactga   5460
caagcctcgc gtacccgatt atccatcggt ggatggagcg actcgttaat cgcttccatg   5520
cgccgcagta acaattgctc aagcagattt atcgccagca gctccgaata gcgcccttcc   5580
ccttgcccgg cgttaatgat ttgcccaaac aggtcgctga atgcggctg gtgcgcttca   5640 tccgggcgaa agaaccccgt attggcaaat attgacggcc agttaagcca ttcatgccag   5700
taggcgcgcg gacgaaagta aacccactgg tgataccatt cgcgagcctc cggatgacga   5760
ccgtagtgat gaatctctcc tggcgggaac agcaaaatat cacccggtcg gcaaacaaat   5820
tctcgtccct gattttttcac cacccctga ccgcgaatgg tgagattgag aatataacct   5880
ttcattccca gcggtcggtc gataaaaaaa tcgagataac cgttggcctc aatcggcgtt   5940
aaacccgcca ccagatgggc attaaacgag tatcccggca gcagggatc attttgcgct   6000 tcagccatac ttttcatact cccgccattc agag                              6034

<210> SEQ ID NO 145
<211> LENGTH: 579
<212> TYPE: DNA
<213> ORGANISM: artificial sequence
<220> FEATURE:
<223> OTHER INFORMATION: synthetic construct

<400> SEQUENCE: 145
atggctagct gcggtcaaca acgttttcaa tggcaattcg aacaacagcc gcgttgcggc     60
cagcaacgct tccaatggca gtttgaacag caaccgcgtt gcggtcagca acgtttccag    120
```

```
tggcaatttg aacaacagcc agagtgcggc agcagcgct ttcagtggca gttcgagcag    180
cagccgtgcg gatcttgctg tccgggctgt tgcggatccg atccatctgc tcaatctcaa    240
ctgcctgata acattctgg tctgcatgaa cgcgctcctc aacgttacgg tccggaggag    300
gcggcgaaga aagaagaggc ggctaaaaag ccggctcaca ttaataagac caacccgcat    360
cagggcaacc atcactccga aaagacccag cgtcagggct ccggtggcgg cggtagcggc    420
agcggtggcg gtggttctga ctcccatcac aaccatcaca gcaggactc ccgccctcag    480 caccgtaaga cgccaaacgg cggtggtgac tctcaccata accaccacaa acaggactct    540
cgcccgcagc accgcaaaac ccctaacggt aaataataa                           579
```

<210> SEQ ID NO 146
<211> LENGTH: 191
<212> TYPE: PRT
<213> ORGANISM: artificial sequence
<220> FEATURE:
<223> OTHER INFORMATION: synthetic construct

<400> SEQUENCE: 146

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
                20                  25                  30

Arg Cys Gly Gln Gln Arg Phe Gln Trp Gln Phe Glu Gln Gln Pro Glu
            35                  40                  45

Cys Gly Gln Gln Arg Phe Gln Trp Gln Phe Glu Gln Gln Pro Cys Gly
        50                  55                  60

Ser Cys Cys Pro Gly Cys Cys Gly Ser Asp Pro Ser Ala Gln Ser Gln
65                  70                  75                  80

Leu Pro Asp Lys His Ser Gly Leu His Glu Arg Ala Pro Gln Arg Tyr
                85                  90                  95

Gly Pro Glu Glu Ala Ala Lys Lys Glu Glu Ala Ala Lys Lys Pro Ala
                100                 105                 110

His Ile Asn Lys Thr Asn Pro His Gln Gly Asn His His Ser Glu Lys
            115                 120                 125

Thr Gln Arg Gln Gly Ser Gly Gly Gly Ser Gly Ser Gly Gly Gly
        130                 135                 140

Gly Ser Asp Ser His His Asn His His Lys Gln Asp Ser Arg Pro Gln
145                 150                 155                 160

His Arg Lys Thr Pro Asn Gly Gly Gly Asp Ser His His Asn His His
                165                 170                 175

Lys Gln Asp Ser Arg Pro Gln His Arg Lys Thr Pro Asn Gly Lys
                180                 185                 190
```

<210> SEQ ID NO 147
<211> LENGTH: 16
<212> TYPE: PRT
<213> ORGANISM: artificial sequence
<220> FEATURE:
<223> OTHER INFORMATION: synthetic construct

<400> SEQUENCE: 147

```
Gly Pro Glu Glu Ala Ala Lys Lys Glu Glu Ala Ala Lys Lys Pro Ala
1               5                   10                  15
```

<210> SEQ ID NO 148
<211> LENGTH: 100

<212> TYPE: DNA
<213> ORGANISM: Escherichia coli

<400> SEQUENCE: 148

```
tttttatcca taagattagc ggatcctacc tgacgctttt tatcgcaact ctctactgtt    60
tctccatacc cgttttttgg gctaacagga ggaattaacc                         100
```

<210> SEQ ID NO 149
<211> LENGTH: 591
<212> TYPE: DNA
<213> ORGANISM: Escherichia coli
<220> FEATURE:
<221> NAME/KEY: CDS
<222> LOCATION: (1)..(591)

<400> SEQUENCE: 149

```
atg aaa gta gca aaa gac ctg gtg gtc agc ctg gcc tat cag gta cgt     48
Met Lys Val Ala Lys Asp Leu Val Val Ser Leu Ala Tyr Gln Val Arg
1               5                   10                  15 aca gaa gac ggt gtg ttg gtt gat gag tct ccg gtg agt gcg ccg ctg     96
Thr Glu Asp Gly Val Leu Val Asp Glu Ser Pro Val Ser Ala Pro Leu
                20                  25                  30 gac tac ctg cat ggt cac ggt tcc ctg atc tct ggc ctg gaa acg gcg    144
Asp Tyr Leu His Gly His Gly Ser Leu Ile Ser Gly Leu Glu Thr Ala
            35                  40                  45 ctg gaa ggt cat gaa gtt ggc gac aaa ttt gat gtc gct gtt ggc gcg    192
Leu Glu Gly His Glu Val Gly Asp Lys Phe Asp Val Ala Val Gly Ala
        50                  55                  60 aac gac gct tac ggt cag tac gac gaa aac ctg gtg caa cgt gtt cct    240
Asn Asp Ala Tyr Gly Gln Tyr Asp Glu Asn Leu Val Gln Arg Val Pro
65                  70                  75                  80 aaa gac gta ttt atg ggc gtt gat gaa ctg cag gta ggt atg cgt ttc    288
Lys Asp Val Phe Met Gly Val Asp Glu Leu Gln Val Gly Met Arg Phe
                85                  90                  95 ctg gct gaa acc gac cag ggt ccg gta ccg gtt gaa atc act gcg gtt    336
Leu Ala Glu Thr Asp Gln Gly Pro Val Pro Val Glu Ile Thr Ala Val
                100                 105                 110 gaa gac gat cac gtc gtg gtt gat ggt aac cac atg ctg gcc ggt cag    384
Glu Asp Asp His Val Val Val Asp Gly Asn His Met Leu Ala Gly Gln
            115                 120                 125 aac ctg aaa ttc aac gtt gaa gtt gtg gcg att cgc gaa gcg act gaa    432
Asn Leu Lys Phe Asn Val Glu Val Val Ala Ile Arg Glu Ala Thr Glu
        130                 135                 140 gaa gaa ctg gct cat ggt cac gtt cac ggc gcg cac gat cac cac cac    480
Glu Glu Leu Ala His Gly His Val His Gly Ala His Asp His His His
145                 150                 155                 160 gat cac gac cac gac ggt tgc tgc ggc ggt cat ggc cac gat cac ggt    528
Asp His Asp His Asp Gly Cys Cys Gly Gly His Gly His Asp His Gly
                165                 170                 175 cat gaa cac ggt ggc gaa ggc tgt tgt ggc ggt aaa ggc aac ggc ggt    576
His Glu His Gly Gly Glu Gly Cys Cys Gly Gly Lys Gly Asn Gly Gly
            180                 185                 190 tgc ggt tgc cac taa                                                591
Cys Gly Cys His
        195
```

<210> SEQ ID NO 150
<211> LENGTH: 196
<212> TYPE: PRT
<213> ORGANISM: Escherichia coli

<400> SEQUENCE: 150

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
        50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Ala Ile Arg Glu Ala Thr Glu
        130                 135                 140

Glu Glu Leu Ala His Gly His Val His Gly Ala His Asp His His His
145                 150                 155                 160

Asp His Asp His Asp Gly Cys Cys Gly His Gly His Asp His Gly
            165                 170                 175

His Glu His Gly Gly Glu Gly Cys Cys Gly Gly Lys Gly Asn Gly Gly
            180                 185                 190

Cys Gly Cys His
        195

<210> SEQ ID NO 151
<211> LENGTH: 8
<212> TYPE: PRT
<213> ORGANISM: Artificial Sequence
<220> FEATURE:
<223> OTHER INFORMATION: synthetic construct

<400> SEQUENCE: 151

Leu Glu Ser Gly Asp Glu Val Asp
1               5

<210> SEQ ID NO 152
<211> LENGTH: 1975
<212> TYPE: DNA
<213> ORGANISM: Escherichia coli

<400> SEQUENCE: 152
aattcgtaag atatcagcca ctataccgat ataataata  agactcacct gcaaaccaga       60
cggtaattta atgatgatga acgctttctt tccggcaatg gcgcttatgg tgctagtggg      120
ttgttctaca ccaccaccag aacagaaagc tcaaagggtg aaagttgatc ccattcggtc      180
attgaatatg aagcgttat gcaaggatca ggcggcaaaa cgttataaca ccggcgagca      240
aaaaatcgac gtcaccgcct tcgaacagtt ccagggaagc tatgaaatgc gcggttatac      300
cttccgtaaa gagcagtttg tctgttcttt tgacgcggat ggccattttt tgcatctttc      360
catgcgttaa gccctgcttt ttcccgtttc gtactgtata tcttccatcc agcgggtata      420
ctgatccctt cctttaaatc cacacgtatc cagcacgaaa taatatgcaa agtttgata       480 ccaggaccct ccagggcttg atcctgacct tacaggatta ctgggctcgc cagggctgca      540
```

```
ccattgttca accattggac atggaagtcg gcgcgggaac ctctcaccca atgacctgtc      600
tgcgcgcgct ggggccagaa ccgatggcgg ctgcttatgt tcagccttct cgtcgcccga      660
ccgatggtcg ctacggcgaa accccaacc gtttacagca ctactatcag ttccaggtgg      720
tcattaagcc atcgccggac aatattcagg agctgtacct cggttctctg aaagagctgg      780
gcatggaccc gactattcac gacatccgtt tcgtggaaga taactgggaa acccgacgc      840
tgggtgcctg gggactgggc tggaagtgt ggctgaacgg catggaagtg acgcagttca      900
cttacttcca gcaggttggt ggtctggagt gtaaaccggt taccggcgag atcacctacg      960
gtctggaacg tctggccatg tacattcagg gcgtagacag cgtttacgac ctggtctgga     1020
gcgacggccc gctgggtaaa accacctacg gcgacgtgtt ccatcagaac gaagtggagc     1080
agtccactta caacttcgaa tacgcggatg tggacttcct gttcacctgc ttcgagcagt     1140
acgagaaaga agcgcagcag ctgctggcgc tggaaaatcc gctgccgctg ccagcctacg     1200
agcgtattct gaaagccgcc cacagcttca acctgctgga tgcgcgtaaa gccatctccg     1260
tcaccgagcg tcagcgctac attctgcgca ttcgcaccct gaccaaagca gtggcagaag     1320
catactacgc ttcccgtgaa gccctcggct tcccgatgtg caacaaagat aagtaagagg     1380
cggctatgtc tgagaaaact tttctggtgg aaatcggcac tgaagagctg ccaccaaaag     1440
cactgcgcag cctggctgag tcctttgctg cgaactttac tgcggagctg ataacgctg     1500
gcctcgcaca cggcaccgtt caatggtttg ctgctccgcg tcgtctggcg ctgaaagtag     1560
ctaacctggc ggaagcgcaa ccggatcgtg aaatcgaaaa acgcggcccg gcgattgccc     1620
aggcgttcga cgctgaaggc aaaccgagca agcggcaga aggttgggcg cgtggttgcg     1680
gtattaccgt tgaccaggct gagcgtctga ctaccgataa aggcgaatgg ctgctgtatc     1740
gcgcccatgt gaagggcgaa agcaccgaag cactgctgcc gaatatggtt gcgacttctc     1800
tggcgaaact gccgatcccg aaactgatgc gttggggcgc aagcgacgtg cacttcgtgc     1860
gtccggtgca caccgtgacc ctgctgctgg gcgacaaagt cattccggca accattctgg     1920
gcattcagtc cgatcgcgtg attcgcggcc accgctttat gggcgagccg gaatt          1975
```

<210> SEQ ID NO 153
<211> LENGTH: 300
<212> TYPE: DNA
<213> ORGANISM: Escherichia coli
<220> FEATURE:
<221> NAME/KEY: CDS
<222> LOCATION: (1)..(300)

<400> SEQUENCE: 153

```
atg atg atg aac gct ttc ttt ccg gca atg gcg ctt atg gtg cta gtg       48
Met Met Met Asn Ala Phe Phe Pro Ala Met Ala Leu Met Val Leu Val
1               5                   10                  15 ggt tgt tct aca cca cca cca gaa cag aaa gct caa agg gtg aaa gtt       96
Gly Cys Ser Thr Pro Pro Pro Glu Gln Lys Ala Gln Arg Val Lys Val
                20                  25                  30 gat ccc att cgg tca ttg aat atg gaa gcg tta tgc aag gat cag gcg      144
Asp Pro Ile Arg Ser Leu Asn Met Glu Ala Leu Cys Lys Asp Gln Ala
            35                  40                  45 gca aaa cgt tat aac acc ggc gag caa aaa atc gac gtc acc gcc ttc      192
Ala Lys Arg Tyr Asn Thr Gly Glu Gln Lys Ile Asp Val Thr Ala Phe
        50                  55                  60 gaa cag ttc cag gga agc tat gaa atg cgc ggt tat acc ttc cgt aaa      240
Glu Gln Phe Gln Gly Ser Tyr Glu Met Arg Gly Tyr Thr Phe Arg Lys
65                  70                  75                  80
```

```
gag cag ttt gtc tgt tct ttt gac gcg gat ggc cat ttt ttg cat ctt      288
Glu Gln Phe Val Cys Ser Phe Asp Ala Asp Gly His Phe Leu His Leu
                85                  90                  95 tcc atg cgt taa                                                       300
Ser Met Arg
```

<210> SEQ ID NO 154
<211> LENGTH: 99
<212> TYPE: PRT
<213> ORGANISM: Escherichia coli

<400> SEQUENCE: 154

```
Met Met Met Asn Ala Phe Phe Pro Ala Met Ala Leu Met Val Leu Val
1               5                   10                  15

Gly Cys Ser Thr Pro Pro Glu Gln Lys Ala Gln Arg Val Lys Val
            20                  25                  30

Asp Pro Ile Arg Ser Leu Asn Met Glu Ala Leu Cys Lys Asp Gln Ala
        35                  40                  45

Ala Lys Arg Tyr Asn Thr Gly Glu Gln Lys Ile Asp Val Thr Ala Phe
    50                  55                  60

Glu Gln Phe Gln Gly Ser Tyr Glu Met Arg Gly Tyr Thr Phe Arg Lys
65                  70                  75                  80

Glu Gln Phe Val Cys Ser Phe Asp Ala Asp Gly His Phe Leu His Leu
                85                  90                  95

Ser Met Arg
```

<210> SEQ ID NO 155
<211> LENGTH: 912
<212> TYPE: DNA
<213> ORGANISM: Escherichia coli
<220> FEATURE:
<221> NAME/KEY: CDS
<222> LOCATION: (1)..(912)

<400> SEQUENCE: 155

```
atg caa aag ttt gat acc agg acc ttc cag ggc ttg atc ctg acc tta      48
Met Gln Lys Phe Asp Thr Arg Thr Phe Gln Gly Leu Ile Leu Thr Leu
1               5                   10                  15 cag gat tac tgg gct cgc cag ggc tgc acc att gtt caa cca ttg gac      96
Gln Asp Tyr Trp Ala Arg Gln Gly Cys Thr Ile Val Gln Pro Leu Asp
                20                  25                  30 atg gaa gtc ggc gcg gga acc tct cac cca atg acc tgt ctg cgc gcg      144
Met Glu Val Gly Ala Gly Thr Ser His Pro Met Thr Cys Leu Arg Ala
            35                  40                  45 ctg ggg cca gaa ccg atg gcg gct gct tat gtt cag cct tct cgt cgc      192
Leu Gly Pro Glu Pro Met Ala Ala Ala Tyr Val Gln Pro Ser Arg Arg
    50                  55                  60 ccg acc gat ggt cgc tac ggc gaa aac ccc aac cgt tta cag cac tac      240
Pro Thr Asp Gly Arg Tyr Gly Glu Asn Pro Asn Arg Leu Gln His Tyr
65                  70                  75                  80 tat cag ttc cag gtg gtc att aag cca tcg ccg gac aat att cag gag      288
Tyr Gln Phe Gln Val Val Ile Lys Pro Ser Pro Asp Asn Ile Gln Glu
                85                  90                  95 ctg tac ctc ggt tct ctg aaa gag ctg ggc atg gac ccg act att cac      336
Leu Tyr Leu Gly Ser Leu Lys Glu Leu Gly Met Asp Pro Thr Ile His
                100                 105                 110 gac atc cgt ttc gtg gaa gat aac tgg gaa aac ccg acg ctg ggt gcc      384
Asp Ile Arg Phe Val Glu Asp Asn Trp Glu Asn Pro Thr Leu Gly Ala
            115                 120                 125 tgg gga ctg ggc tgg gaa gtg tgg ctg aac ggc atg gaa gtg acg cag      432
```

```
                Trp Gly Leu Gly Trp Glu Val Trp Leu Asn Gly Met Glu Val Thr Gln
                            130                 135                 140 ttc act tac ttc cag cag gtt ggt ggt ctg gag tgt aaa ccg gtt acc              480
Phe Thr Tyr Phe Gln Gln Val Gly Gly Leu Glu Cys Lys Pro Val Thr
145                 150                 155                 160 ggc gag atc acc tac ggt ctg gaa cgt ctg gcc atg tac att cag ggc              528
Gly Glu Ile Thr Tyr Gly Leu Glu Arg Leu Ala Met Tyr Ile Gln Gly
                165                 170                 175 gta gac agc gtt tac gac ctg gtc tgg agc gac ggc ccg ctg ggt aaa              576
Val Asp Ser Val Tyr Asp Leu Val Trp Ser Asp Gly Pro Leu Gly Lys
            180                 185                 190 acc acc tac ggc gac gtg ttc cat cag aac gaa gtg gag cag tcc act              624
Thr Thr Tyr Gly Asp Val Phe His Gln Asn Glu Val Glu Gln Ser Thr
        195                 200                 205 tac aac ttc gaa tac gcg gat gtg gac ttc ctg ttc acc tgc ttc gag              672
Tyr Asn Phe Glu Tyr Ala Asp Val Asp Phe Leu Phe Thr Cys Phe Glu
    210                 215                 220 cag tac gag aaa gaa gcg cag cag ctg ctg gcg ctg gaa aat ccg ctg              720
Gln Tyr Glu Lys Glu Ala Gln Gln Leu Leu Ala Leu Glu Asn Pro Leu
225                 230                 235                 240 ccg ctg cca gcc tac gag cgt att ctg aaa gcc gcc cac agc ttc aac              768
Pro Leu Pro Ala Tyr Glu Arg Ile Leu Lys Ala Ala His Ser Phe Asn
                245                 250                 255 ctg ctg gat gcg cgt aaa gcc atc tcc gtc acc gag cgt cag cgc tac              816
Leu Leu Asp Ala Arg Lys Ala Ile Ser Val Thr Glu Arg Gln Arg Tyr
            260                 265                 270 att ctg cgc att cgc acc ctg acc aaa gca gtg gca gaa gca tac tac              864
Ile Leu Arg Ile Arg Thr Leu Thr Lys Ala Val Ala Glu Ala Tyr Tyr
        275                 280                 285 gct tcc cgt gaa gcc ctc ggc ttc ccg atg tgc aac aaa gat aag taa              912
Ala Ser Arg Glu Ala Leu Gly Phe Pro Met Cys Asn Lys Asp Lys
    290                 295                 300

<210> SEQ ID NO 156
<211> LENGTH: 303
<212> TYPE: PRT
<213> ORGANISM: Escherichia coli

<400> SEQUENCE: 156

Met Gln Lys Phe Asp Thr Arg Thr Phe Gln Gly Leu Ile Leu Thr Leu
1               5                   10                  15

Gln Asp Tyr Trp Ala Arg Gln Gly Cys Thr Ile Val Gln Pro Leu Asp
            20                  25                  30

Met Glu Val Gly Ala Gly Thr Ser His Pro Met Thr Cys Leu Arg Ala
        35                  40                  45

Leu Gly Pro Glu Pro Met Ala Ala Ala Tyr Val Gln Pro Ser Arg Arg
    50                  55                  60

Pro Thr Asp Gly Arg Tyr Gly Glu Asn Pro Asn Arg Leu Gln His Tyr
65                  70                  75                  80

Tyr Gln Phe Gln Val Val Ile Lys Pro Ser Pro Asp Asn Ile Gln Glu
                85                  90                  95

Leu Tyr Leu Gly Ser Leu Lys Glu Leu Gly Met Asp Pro Thr Ile His
            100                 105                 110

Asp Ile Arg Phe Val Glu Asp Asn Trp Glu Asn Pro Thr Leu Gly Ala
        115                 120                 125

Trp Gly Leu Gly Trp Glu Val Trp Leu Asn Gly Met Glu Val Thr Gln
    130                 135                 140

Phe Thr Tyr Phe Gln Gln Val Gly Gly Leu Glu Cys Lys Pro Val Thr
```

```
                    145                 150                 155                 160
Gly Glu Ile Thr Tyr Gly Leu Glu Arg Leu Ala Met Tyr Ile Gln Gly
                165                 170                 175

Val Asp Ser Val Tyr Asp Leu Val Trp Ser Asp Gly Pro Leu Gly Lys
                180                 185                 190

Thr Thr Tyr Gly Asp Val Phe His Gln Asn Glu Val Glu Gln Ser Thr
                195                 200                 205

Tyr Asn Phe Glu Tyr Ala Asp Val Asp Phe Leu Phe Thr Cys Phe Glu
            210                 215                 220

Gln Tyr Glu Lys Glu Ala Gln Gln Leu Leu Ala Leu Glu Asn Pro Leu
225                 230                 235                 240

Pro Leu Pro Ala Tyr Glu Arg Ile Leu Lys Ala Ala His Ser Phe Asn
                245                 250                 255

Leu Leu Asp Ala Arg Lys Ala Ile Ser Val Thr Glu Arg Gln Arg Tyr
                260                 265                 270

Ile Leu Arg Ile Arg Thr Leu Thr Lys Ala Val Ala Glu Ala Tyr Tyr
                275                 280                 285

Ala Ser Arg Glu Ala Leu Gly Phe Pro Met Cys Asn Lys Asp Lys
                290                 295                 300

<210> SEQ ID NO 157
<211> LENGTH: 2070
<212> TYPE: DNA
<213> ORGANISM: Escherichia coli
<220> FEATURE:
<221> NAME/KEY: CDS
<222> LOCATION: (1)..(2070)

<400> SEQUENCE: 157 atg tct gag aaa act ttt ctg gtg gaa atc ggc act gaa gag ctg cca      48
Met Ser Glu Lys Thr Phe Leu Val Glu Ile Gly Thr Glu Glu Leu Pro
1               5                   10                  15 cca aaa gca ctg cgc agc ctg gct gag tcc ttt gct gcg aac ttt act      96
Pro Lys Ala Leu Arg Ser Leu Ala Glu Ser Phe Ala Ala Asn Phe Thr
                20                  25                  30 gcg gag ctg gat aac gct ggc ctc gca cac ggc acc gtt caa tgg ttt     144
Ala Glu Leu Asp Asn Ala Gly Leu Ala His Gly Thr Val Gln Trp Phe
            35                  40                  45 gct gct ccg cgt cgt ctg gcg ctg aaa gta gct aac ctg gcg gaa gcg     192
Ala Ala Pro Arg Arg Leu Ala Leu Lys Val Ala Asn Leu Ala Glu Ala
        50                  55                  60 caa ccg gat cgt gaa atc gaa aaa cgc ggc ccg gcg att gcc cag gcg     240
Gln Pro Asp Arg Glu Ile Glu Lys Arg Gly Pro Ala Ile Ala Gln Ala
65                  70                  75                  80 ttc gac gct gaa ggc aaa ccg agc aaa gcg gca gaa ggt tgg gcg cgt     288
Phe Asp Ala Glu Gly Lys Pro Ser Lys Ala Ala Glu Gly Trp Ala Arg
                85                  90                  95 ggt tgc ggt att acc gtt gac cag gct gag cgt ctg act acc gat aaa     336
Gly Cys Gly Ile Thr Val Asp Gln Ala Glu Arg Leu Thr Thr Asp Lys
                100                 105                 110 ggc gaa tgg ctg ctg tat cgc gcc cat gtg aag ggc gaa agc acc gaa     384
Gly Glu Trp Leu Leu Tyr Arg Ala His Val Lys Gly Glu Ser Thr Glu
            115                 120                 125 gca ctg ctg ccg aat atg gtt gcg act tct ctg gcg aaa ctg ccg atc     432
Ala Leu Leu Pro Asn Met Val Ala Thr Ser Leu Ala Lys Leu Pro Ile
        130                 135                 140 ccg aaa ctg atg cgt tgg ggc gca agc gac gtg cac ttc gtg cgt ccg     480
Pro Lys Leu Met Arg Trp Gly Ala Ser Asp Val His Phe Val Arg Pro
145                 150                 155                 160
```

| | | |
|---|---|---|
| gtg cac acc gtg acc ctg ctg ctg ggc gac aaa gtc att ccg gca acc<br>Val His Thr Val Thr Leu Leu Leu Gly Asp Lys Val Ile Pro Ala Thr<br>                      165                      170              175 | 528 |
| att ctg ggc att cag tcc gat cgc gtg att cgc ggc cac cgc ttt atg<br>Ile Leu Gly Ile Gln Ser Asp Arg Val Ile Arg Gly His Arg Phe Met<br>         180                     185                   190 | 576 |
| ggc gag ccg gaa ttc acc atc gat aac gcc gat cag tat ccg gaa att<br>Gly Glu Pro Glu Phe Thr Ile Asp Asn Ala Asp Gln Tyr Pro Glu Ile<br>        195                     200                   205 | 624 |
| ctg cgt gag cgt ggg aaa gtc atc gct gat tac gaa gaa cgt aag gcg<br>Leu Arg Glu Arg Gly Lys Val Ile Ala Asp Tyr Glu Glu Arg Lys Ala<br>    210                     215                   220 | 672 |
| aag att aaa gcc gat gcc gaa gaa gca gcg cgt aag att ggc ggt aac<br>Lys Ile Lys Ala Asp Ala Glu Glu Ala Ala Arg Lys Ile Gly Gly Asn<br>225                   230                   235                  240 | 720 |
| gct gac tta agc gaa agc ctg ctg gaa gaa gtg gct tcg ctg gtg gag<br>Ala Asp Leu Ser Glu Ser Leu Leu Glu Glu Val Ala Ser Leu Val Glu<br>                      245                   250                  255 | 768 |
| tgg ccg gtc gtt ctg acc gca aaa ttc gaa gag aaa ttc ctc gcg gtg<br>Trp Pro Val Val Leu Thr Ala Lys Phe Glu Glu Lys Phe Leu Ala Val<br>              260                   265                  270 | 816 |
| ccg gct gaa gcg ctg gtt tac acc atg aaa ggt gac cag aaa tac ttc<br>Pro Ala Glu Ala Leu Val Tyr Thr Met Lys Gly Asp Gln Lys Tyr Phe<br>        275                     280                   285 | 864 |
| ccg gtg tat gcg aac gac ggc aaa ctg ctg ccg aac ttt atc ttc gtt<br>Pro Val Tyr Ala Asn Asp Gly Lys Leu Leu Pro Asn Phe Ile Phe Val<br>    290                     295                   300 | 912 |
| gcc aac atc gaa tcg aaa gat ccg cag cag att atc tcc ggt aac gag<br>Ala Asn Ile Glu Ser Lys Asp Pro Gln Gln Ile Ile Ser Gly Asn Glu<br>305                   310                   315                  320 | 960 |
| aaa gtc gtt cgt ccg cgt ctg gcg gat gcc gag ttc ttc ttc aac acc<br>Lys Val Val Arg Pro Arg Leu Ala Asp Ala Glu Phe Phe Phe Asn Thr<br>                      325                   330                  335 | 1008 |
| gac cgt aaa aaa cgt ctt gaa gat aac ctg ccg cgc ctg caa acc gtg<br>Asp Arg Lys Lys Arg Leu Glu Asp Asn Leu Pro Arg Leu Gln Thr Val<br>              340                   345                  350 | 1056 |
| ttg ttc cag caa cag ttg ggg acg ctg cgc gac aaa act gac cgc atc<br>Leu Phe Gln Gln Gln Leu Gly Thr Leu Arg Asp Lys Thr Asp Arg Ile<br>        355                     360                   365 | 1104 |
| cag gcg ctg gct ggc tgg att gct gaa cag att ggc gct gac gtt aac<br>Gln Ala Leu Ala Gly Trp Ile Ala Glu Gln Ile Gly Ala Asp Val Asn<br>    370                     375                   380 | 1152 |
| cac gct acc cgt gcg ggt ctg ctg tct aag tgc gac ctg atg acc aac<br>His Ala Thr Arg Ala Gly Leu Leu Ser Lys Cys Asp Leu Met Thr Asn<br>385                   390                   395                  400 | 1200 |
| atg gtc ttc gag ttc acc gac acc cag ggc gtt atg ggg atg cac tat<br>Met Val Phe Glu Phe Thr Asp Thr Gln Gly Val Met Gly Met His Tyr<br>        405                     410                   415 | 1248 |
| gcg cgt cac gat ggc gaa gcg gaa gat gtc gcg gtg gcg ctg aat gag<br>Ala Arg His Asp Gly Glu Ala Glu Asp Val Ala Val Ala Leu Asn Glu<br>                      420                   425                  430 | 1296 |
| cag tat cag ccg cgt ttt gct ggt gat gac ctg ccg tcc aac cca gta<br>Gln Tyr Gln Pro Arg Phe Ala Gly Asp Asp Leu Pro Ser Asn Pro Val<br>        435                     440                   445 | 1344 |
| gct tgt gcg ctg gcg att gct gac aag atg gat acc ctg gcg ggt atc<br>Ala Cys Ala Leu Ala Ile Ala Asp Lys Met Asp Thr Leu Ala Gly Ile<br>    450                     455                   460 | 1392 |
| ttc ggt atc ggt cag cat ccg aaa ggc gac aaa gac ccg ttt gcg ctg<br>Phe Gly Ile Gly Gln His Pro Lys Gly Asp Lys Asp Pro Phe Ala Leu | 1440 |

```
                      465                 470                 475                 480
cgt cgt gcc gcg ctt ggc gtg ctg cga att atc gtt gag aag aac ctc         1488
Arg Arg Ala Ala Leu Gly Val Leu Arg Ile Ile Val Glu Lys Asn Leu
                485                 490                 495 aac ctt gat ctg caa acg ctg acc gaa gaa gcg gtg cgt ctg tat ggc         1536
Asn Leu Asp Leu Gln Thr Leu Thr Glu Glu Ala Val Arg Leu Tyr Gly
            500                 505                 510 gat aag ctg act aat gcc aac gta gtt gat gat gtt atc gac ttt atg         1584
Asp Lys Leu Thr Asn Ala Asn Val Val Asp Asp Val Ile Asp Phe Met
        515                 520                 525 ctc ggt cgc ttc cgc gcc tgg tat cag gac gaa ggt tat acc gtt gac         1632
Leu Gly Arg Phe Arg Ala Trp Tyr Gln Asp Glu Gly Tyr Thr Val Asp
    530                 535                 540 acc atc cag gcg gta ctg gcg cgt cgt ccg act cgt ccg gct gat ttc         1680
Thr Ile Gln Ala Val Leu Ala Arg Arg Pro Thr Arg Pro Ala Asp Phe
545                 550                 555                 560 gat gcc cgt atg aaa gcg gta tcg cat ttc cgt acc ctg gat gca gct         1728
Asp Ala Arg Met Lys Ala Val Ser His Phe Arg Thr Leu Asp Ala Ala
                565                 570                 575 gct gca ctg gcg gcg gcg aac aaa cgt gta tct aac att ctg gcg aaa         1776
Ala Ala Leu Ala Ala Ala Asn Lys Arg Val Ser Asn Ile Leu Ala Lys
            580                 585                 590 tct gac gaa gtg ctg agc gac cgc gtg aat gcc tct acc ctg aaa gag         1824
Ser Asp Glu Val Leu Ser Asp Arg Val Asn Ala Ser Thr Leu Lys Glu
        595                 600                 605 ccg gaa gaa att aaa ctg gcg atg cag gtt gtg gtg cta cgt gac aag         1872
Pro Glu Glu Ile Lys Leu Ala Met Gln Val Val Val Leu Arg Asp Lys
    610                 615                 620 ctg gag ccg tac ttt acg gaa ggt cgt tac cag gat gcg ctg gtc gaa         1920
Leu Glu Pro Tyr Phe Thr Glu Gly Arg Tyr Gln Asp Ala Leu Val Glu
625                 630                 635                 640 ctg gct gag ctg cgt gaa ccg gtt gat gct ttc ttc gat aaa gtg atg         1968
Leu Ala Glu Leu Arg Glu Pro Val Asp Ala Phe Phe Asp Lys Val Met
                645                 650                 655 gtc atg gtt gat gac aaa gaa ttg cgt atc aac cgt ctg acc atg ctg         2016
Val Met Val Asp Asp Lys Glu Leu Arg Ile Asn Arg Leu Thr Met Leu
            660                 665                 670 gag aaa ctg cgc gaa ctg ttc ctg cgc gtt gcg gat att tcg ctg ttg         2064
Glu Lys Leu Arg Glu Leu Phe Leu Arg Val Ala Asp Ile Ser Leu Leu
        675                 680                 685 caa taa                                                                  2070
Gln <210> SEQ ID NO 158
<211> LENGTH: 689
<212> TYPE: PRT
<213> ORGANISM: Escherichia coli

<400> SEQUENCE: 158

Met Ser Glu Lys Thr Phe Leu Val Glu Ile Gly Thr Glu Glu Leu Pro
1               5                   10                  15

Pro Lys Ala Leu Arg Ser Leu Ala Glu Ser Phe Ala Ala Asn Phe Thr
            20                  25                  30

Ala Glu Leu Asp Asn Ala Gly Leu Ala His Gly Thr Val Gln Trp Phe
        35                  40                  45

Ala Ala Pro Arg Arg Leu Ala Leu Lys Val Ala Asn Leu Ala Glu Ala
    50                  55                  60

Gln Pro Asp Arg Glu Ile Glu Lys Arg Gly Pro Ala Ile Ala Gln Ala
65                  70                  75                  80
```

```
Phe Asp Ala Glu Gly Lys Pro Ser Lys Ala Glu Gly Trp Ala Arg
                85                  90                  95

Gly Cys Gly Ile Thr Val Asp Gln Ala Glu Arg Leu Thr Thr Asp Lys
            100                 105                 110

Gly Glu Trp Leu Leu Tyr Arg Ala His Val Lys Gly Ser Thr Glu
        115                 120                 125

Ala Leu Leu Pro Asn Met Val Ala Thr Ser Leu Ala Lys Leu Pro Ile
130                 135                 140

Pro Lys Leu Met Arg Trp Gly Ala Ser Asp Val His Phe Val Arg Pro
145                 150                 155                 160

Val His Thr Val Thr Leu Leu Leu Gly Asp Lys Val Ile Pro Ala Thr
                165                 170                 175

Ile Leu Gly Ile Gln Ser Asp Arg Val Ile Arg Gly His Arg Phe Met
                180                 185                 190

Gly Glu Pro Glu Phe Thr Ile Asp Asn Ala Asp Gln Tyr Pro Glu Ile
            195                 200                 205

Leu Arg Glu Arg Gly Lys Val Ile Ala Asp Tyr Glu Glu Arg Lys Ala
        210                 215                 220

Lys Ile Lys Ala Asp Ala Glu Ala Ala Arg Lys Ile Gly Gly Asn
225                 230                 235                 240

Ala Asp Leu Ser Glu Ser Leu Leu Glu Glu Val Ala Ser Leu Val Glu
                245                 250                 255

Trp Pro Val Val Leu Thr Ala Lys Phe Glu Glu Lys Phe Leu Ala Val
                260                 265                 270

Pro Ala Glu Ala Leu Val Tyr Thr Met Lys Gly Asp Gln Lys Tyr Phe
            275                 280                 285

Pro Val Tyr Ala Asn Asp Gly Lys Leu Leu Pro Asn Phe Ile Phe Val
            290                 295                 300

Ala Asn Ile Glu Ser Lys Asp Pro Gln Gln Ile Ile Ser Gly Asn Glu
305                 310                 315                 320

Lys Val Val Arg Pro Arg Leu Ala Asp Ala Glu Phe Phe Phe Asn Thr
                325                 330                 335

Asp Arg Lys Lys Arg Leu Glu Asp Asn Leu Pro Arg Leu Gln Thr Val
                340                 345                 350

Leu Phe Gln Gln Gln Leu Gly Thr Leu Arg Asp Lys Thr Asp Arg Ile
        355                 360                 365

Gln Ala Leu Ala Gly Trp Ile Ala Glu Gln Ile Gly Ala Asp Val Asn
    370                 375                 380

His Ala Thr Arg Ala Gly Leu Leu Ser Lys Cys Asp Leu Met Thr Asn
385                 390                 395                 400

Met Val Phe Glu Phe Thr Asp Thr Gln Gly Val Met Gly Met His Tyr
                405                 410                 415

Ala Arg His Asp Gly Glu Ala Glu Asp Val Ala Val Ala Leu Asn Glu
                420                 425                 430

Gln Tyr Gln Pro Arg Phe Ala Gly Asp Leu Pro Ser Asn Pro Val
    435                 440                 445

Ala Cys Ala Leu Ala Ile Ala Asp Lys Met Asp Thr Leu Ala Gly Ile
450                 455                 460

Phe Gly Ile Gly Gln His Pro Lys Gly Asp Lys Asp Pro Phe Ala Leu
465                 470                 475                 480

Arg Arg Ala Ala Leu Gly Val Leu Arg Ile Ile Val Glu Lys Asn Leu
                485                 490                 495
```

```
Asn Leu Asp Leu Gln Thr Leu Thr Glu Glu Ala Val Arg Leu Tyr Gly
            500                 505                 510
Asp Lys Leu Thr Asn Ala Asn Val Val Asp Asp Val Ile Asp Phe Met
        515                 520                 525
Leu Gly Arg Phe Arg Ala Trp Tyr Gln Asp Glu Gly Tyr Thr Val Asp
    530                 535                 540
Thr Ile Gln Ala Val Leu Ala Arg Arg Pro Thr Arg Pro Ala Asp Phe
545                 550                 555                 560
Asp Ala Arg Met Lys Ala Val Ser His Phe Arg Thr Leu Asp Ala Ala
                565                 570                 575
Ala Ala Leu Ala Ala Asn Lys Arg Val Ser Asn Ile Leu Ala Lys
            580                 585                 590
Ser Asp Glu Val Leu Ser Asp Arg Val Asn Ala Ser Thr Leu Lys Glu
        595                 600                 605
Pro Glu Glu Ile Lys Leu Ala Met Gln Val Val Val Leu Arg Asp Lys
    610                 615                 620
Leu Glu Pro Tyr Phe Thr Glu Gly Arg Tyr Gln Asp Ala Leu Val Glu
625                 630                 635                 640
Leu Ala Glu Leu Arg Glu Pro Val Asp Ala Phe Phe Asp Lys Val Met
                645                 650                 655
Val Met Val Asp Asp Lys Glu Leu Arg Ile Asn Arg Leu Thr Met Leu
            660                 665                 670
Glu Lys Leu Arg Glu Leu Phe Leu Arg Val Ala Asp Ile Ser Leu Leu
        675                 680                 685
Gln
```

<210> SEQ ID NO 159
<211> LENGTH: 5324
<212> TYPE: DNA
<213> ORGANISM: artificial sequence
<220> FEATURE:
<223> OTHER INFORMATION: Plasmid pDCQ601

<400> SEQUENCE: 159

```
ctcgggccgt ctcttgggct tgatcggcct tcttgcgcat ctcacgcgct cctgcggcgg     60
cctgtagggc aggctcatac ccctgccgaa ccgcttttgt cagccggtcg ccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg ccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcgcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc cctttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
```

```
ttcgccctgc gcggtcgctg cgctcccttg ccagcccgtg gatatgtgga cgatggccgc    1020
gagcggccac cggctggctc gcttcgctcg gcccgtggac aaccctgctg acaagctga    1080 tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380 tgcccccga gacctgcagg ggggggggg cgctgaggtc tgcctcgtga agaaggtgtt    1440
gctgactcat accaggcctg aatcgcccca tcatccagcc agaaagtgag ggagccacgg    1500
ttgatgagag ctttgttgta ggtggaccag ttggtgattt tgaacttttg ctttgccacg    1560
gaacggtctg cgttgtcggg aagatgcgtg atctgatcct tcaactcagc aaaagttcga    1620
tttattcaac aaagccgccg tcccgtcaag tcagcgtaat gctctgccag tgttacaacc    1680
aattaaccaa ttctgattag aaaaactcat cgagcatcaa atgaaactgc aatttattca    1740
tatcaggatt atcaatacca tattttttgaa aaagccgttt ctgtaatgaa ggagaaaact    1800
caccgaggca gttccatagg atggcaagat cctggtatcg gtctgcgatt ccgactcgtc    1860
caacatcaat acaacctatt aatttcccct cgtcaaaaat aaggttatca agtgagaaat    1920
caccatgagt gacgactgaa tccggtgaga atggcaaaag cttatgcatt tctttccaga    1980
cttgttcaac aggccagcca ttacgctcgt catcaaaatc actcgcatca accaaaccgt    2040
tattcattcg tgattgcgcc tgagcgagac gaaatacgcg atcgctgtta aaaggacaat    2100
tacaaacagg aatcgaatgc aaccggcgca ggaacactgc cagcgcatca acaatatttt    2160
cacctgaatc aggatattct tctaatacct ggaatgctgt ttttcccgggg atcgcagtgg    2220 tgagtaacca tgcatcatca ggagtacgga taaaatgctt gatggtcgga agaggcataa    2280
attccgtcag ccagtttagt ctgaccatct catctgtaac atcattggca acgctacctt    2340
tgccatgttt cagaaacaac tctggcgcat cgggcttccc atacaatcga tagattgtcg    2400
cacctgattg cccgacatta tcgcgagccc atttataccc atataaatca gcatccatgt    2460
tggaatttaa tcgcggcctc gagcaagacg tttcccgttg aatatggctc ataacacccc    2520
ttgtattact gtttatgtaa gcagacagtt ttattgttca tgatgatata tttttatctt    2580
gtgcaatgta acatcagaga ttttgagaca aacgtggct ttccccccc ccctgcagg    2640 tcccgagcct cacggcggcg agtgcgggg ttccaagggg gcagcgccac cttgggcaag    2700
gccgaaggcc gcgcagtcga tcaacaagcc ccggagggc cactttttgc cggagggga    2760 gccgcgccga aggcgtgggg gaaccccgca ggggtgccct tctttgggca ccaaagaact    2820
agatataggg cgaaatgcga aagacttaaa aatcaacaac ttaaaaaagg ggggtacgca    2880
acagctcatt gcggcacccc ccgcaatagc tcattgcgta ggttaaagaa aatctgtaat    2940
tgactgccac ttttacgcaa cgcataattg ttgtcgcgct gccgaaaagt tgcagctgat    3000
tgcgcatggt gccgcaaccg tgcggcaccc taccgcatgg agataagcat ggccacgcag    3060
tccagagaaa tcggcattca agccaagaac aagcccggtc actgggtgca aacggaacgc    3120
aaagcgcatg aggcgtgggc cgggcttatt gcgaggaaac ccacggcggc aatgctgctg    3180
catcacctcg tggcgcagat gggccaccag aacgccgtgg tggtcagcca aagacactt    3240 tccaagctca tcggacgttc tttgcggacg gtccaatacg cagtcaagga cttggtggcc    3300
```

```
gagcgctgga tctccgtcgt gaagctcaac ggccccggca ccgtgtcggc ctacgtggtc      3360
aatgaccgcg tggcgtgggg ccagccccgc gaccagttgc gcctgtcggt gttcagtgcc      3420
gccgtggtgg ttgatcacga cgaccaggac gaatcgctgt tggggcatgg cgacctgcgc      3480
cgcatcccga ccctgtatcc gggcgagcag caactaccga ccggcccccgg cgaggagccg     3540 cccagccagc ccggcattcc gggcatggaa ccagacctgc cagccttgac cgaaacggag      3600
gaatgggaac ggcgcgggca gcagcgcctg ccgatgcccg atgagccgtg ttttctggac      3660
gatggcgagc cgttggagcc gccgacacgg gtcacgctgc cgcgccggta gcacttgggt      3720
tgcgcagcaa cccgtaagtg cgctgttcca gactatcggc tgtagccgcc tcgccgccct      3780
ataccttgtc tgcctccccg cgttgcgtcg cggtgcatgg agccgggcca cctcgacctg      3840
aatggaagcc ggcggcacct cgctaacgga ttcaccgttt ttatcaggct ctgggaggca      3900
gaataaatga tcatatcgtc aattattacc tcccacgggga gagcctgagc aaactggcct      3960
caggcatttg agaagcacac ggtcacactg cttccggtag tcaataaacc ggtaaaccag      4020
caatagacat aagcggctat ttaacgaccc tgccctgaac cgacgaccgg gtcgaatttg      4080
ctttcgaatt tctgccattc atccgcttat tatacttatt caggcgtagc accaggcgtt      4140
taagggcacc aataactgcc ttaaaaaaat tacgccccgc cctgccactc atcgcagtac      4200
tgttgtaatt cattaagcat tctgccgaca tggaagccat cacagacggc atgatgaacc      4260
tgaatcgcca gcggcatcag caccttgtcg ccttgcgtat aatatttgcc catggtgaaa      4320 acggggggcga agaagttgtc catattggcc acgtttaaat caaaactggt gaaactcacc      4380
cagggattgg ctgagacgaa aaacatattc tcaataaacc ctttagggaa ataggccagg      4440
ttttcaccgt aacacgccac atcttgcgaa tatatgtgta gaaactgccg gaaatcgtcg      4500
tggtattcac tccagagcga tgaaaacgtt tcagtttgct catggaaaac ggtgtaacaa      4560
gggtgaacac tatcccatat caccagctca ccgtctttca ttgccatacg gaattcgcta      4620
gcgtcgacac tagtcaattc cggatgagca ttcatcaggc gggcaagaat gtgaataaag      4680
gccggataaa acttgtgctt attttttcttt acggtcttta aaaaggccgt aatatccagc      4740
tgaacggtct ggttataggt acattgagca actgactgaa atgcctcaaa atgttcttta      4800
cgatgccatt gggatatatc aacggtggta tatccagtga tttttttctc cattttagct      4860
tccttagctc ctgaaaatct cgataactca aaaaatacgc ccggtagtga tcttatttca      4920
ttatggtgaa agttggaacc tcttacgtgc cgatcaacgt ctcattttcg ccaaaagttg      4980
gcccagggct tccggtatc aacagggaca ccaggattta tttattctgc gaagtgatct      5040
tccgtcacag gtatttattc ggcgcaaagg gcctcgtgat acgcctattt ttataggtta      5100
atgtcatgat aataatggtt tcttagacgt caggtggcac ttttcgggga atgtgcgcg      5160 cccgcgttcc tgctggcgct gggcctgttt ctggcgctgg acttcccgct gttccgtcag      5220
cagcttttcg cccacggcct tgatgatcgc ggcggccttg gcctgcatat cccgattcaa      5280
cggccccagg gcgtccagaa cgggcttcag gcgctcccga aggt                      5324

<210> SEQ ID NO 160
<211> LENGTH: 590
<212> TYPE: DNA
<213> ORGANISM: Escherichia coli

<400> SEQUENCE: 160
atgtctgaga aaactttct ggtggaaatc ggcactgaag agctgccacc aaaagcactg       60
cgcagcctgg ctgagtcctt tgctgcgaac tttactgcgg agctggataa cgctggcctc      120
```

```
gcacacggca ccgttcaatg gtttgctgct ccgcgtcgtc tggcgctgaa agtagctaac    180
ctggcggaag cgcaaccgga tcgtgaaatc gaaaaacgcg gcccggcgat tgcccaggcg    240
ttcgacgctg aaggcaaacc gagcaaagcg gcagaaggtt gggcgcgtgg ttgcggtatt    300
accgttgacc aggctgagcg tctgactacc gataaaggcg aatggctgct gtatcgcgcc    360
catgtgaagg gcgaaagcac cgaagcactg ctgccgaata tggttgcgac ttctctggcg    420
aaactgccga tcccgaaact gatgcgttgg ggcgcaagcg acgtgcactt cgtgcgtccg    480
gtgcacaccg tgaccctgct gctgggcgac aaagtcattc cggcaaccat tctgggcatt    540
cagtccgatc gcgtgattcg cggccaccgc tttatgggcg agccggaatt             590
```

<210> SEQ ID NO 161
<211> LENGTH: 196
<212> TYPE: PRT
<213> ORGANISM: Escherichia coli

<400> SEQUENCE: 161

```
Met Ser Glu Lys Thr Phe Leu Val Glu Ile Gly Thr Glu Glu Leu Pro
1               5                   10                  15

Pro Lys Ala Leu Arg Ser Leu Ala Glu Ser Phe Ala Ala Asn Phe Thr
            20                  25                  30

Ala Glu Leu Asp Asn Ala Gly Leu Ala His Gly Thr Val Gln Trp Phe
        35                  40                  45

Ala Ala Pro Arg Arg Leu Ala Leu Lys Val Ala Asn Leu Ala Glu Ala
    50                  55                  60

Gln Pro Asp Arg Glu Ile Glu Lys Arg Gly Pro Ala Ile Ala Gln Ala
65                  70                  75                  80

Phe Asp Ala Glu Gly Lys Pro Ser Lys Ala Ala Glu Gly Trp Ala Arg
                85                  90                  95

Gly Cys Gly Ile Thr Val Asp Gln Ala Glu Arg Leu Thr Thr Asp Lys
            100                 105                 110

Gly Glu Trp Leu Leu Tyr Arg Ala His Val Lys Gly Glu Ser Thr Glu
        115                 120                 125

Ala Leu Leu Pro Asn Met Val Thr Ser Leu Ala Lys Leu Pro Ile
    130                 135                 140

Pro Lys Leu Met Arg Trp Gly Ala Ser Asp Val His Phe Val Arg Pro
145                 150                 155                 160

Val His Thr Val Thr Leu Leu Leu Gly Asp Lys Val Ile Pro Ala Thr
                165                 170                 175

Ile Leu Gly Ile Gln Ser Asp Arg Val Ile Arg Gly His Arg Phe Met
            180                 185                 190

Gly Glu Pro Glu
        195
```

<210> SEQ ID NO 162
<211> LENGTH: 21
<212> TYPE: DNA
<213> ORGANISM: artificial sequence
<220> FEATURE:
<223> OTHER INFORMATION: primer

<400> SEQUENCE: 162

```
gcgatgaaaa cgtttcagtt t                                              21
```

<210> SEQ ID NO 163
<211> LENGTH: 21

```
<212> TYPE: DNA
<213> ORGANISM: artificial
<220> FEATURE:
<223> OTHER INFORMATION: primer

<400> SEQUENCE: 163
cacaagtttt atccggcctt t                                              21

<210> SEQ ID NO 164
<211> LENGTH: 1284
<212> TYPE: DNA
<213> ORGANISM: Escherichia coli

<400> SEQUENCE: 164
atggctgata caaaagcaaa actcaccctc aacggggata cagctgttga actggatgtg     60
ctgaaaggca cgctgggtca agatgttatt gatatccgta ctctcggttc aaaaggtgtg    120
ttcacctttg acccaggctt cacttcaacc gcatcctgcg aatctaaaat tacttttatt    180
gatggtgatg aaggtatttt gctgcaccgc ggtttcccga tcgatcagct ggcgaccgat    240
tctaactacc tggaagtttg ttacatcctg ctgaatggtg aaaaaccgac tcaggaacag    300
tatgacgaat ttaaaactac ggtgacccgt cataccatga tccacgagca gattacccgt    360
ctgttccatg ctttccgtcg cgactcgcat ccaatggcag tcatgtgtgg tattaccggc    420
gcgctggcgg cgttctatca cgactcgctg atgttaaca atcctcgtca ccgtgaaatt    480
gccgcgttcc gcctgctgtc gaaaatgccg accatggccg cgatgtgtta caagtattcc    540
attggtcagc catttgttta cccgcgcaac gatctctcct acgccggtaa cttcctgaat    600
atgatgttct ccacgccgtg cgaaccgtat gaagttaatc cgattctgga acgtgctatg    660
gaccgtattc tgatcctgca cgctgaccat gaacagaacg cctctacctc caccgtgcgt    720
accgctggct cttcgggtgc gaacccgttt gcctgtatcg cagcaggtat tgcttcactg    780
tggggacctg cgcacggcgg tgctaacgaa gcggcgctga aatgctgga agaaatcagc    840 tccgttaaac acattccgga atttgttcgt cgtgcgaaag acaaaaatga ttctttccgc    900
ctgatgggct tcggtcaccg cgtgtacaaa aattacgacc cgcgcgccac cgtaatgcgt    960
gaaacctgcc atgaagtgct gaaagagctg ggcacgaagg atgacctgct ggaagtggct   1020
atggagctgg aaaacatcgc gctgaacgac ccgtacttta tcgagaagaa actgtacccg   1080
aacgtcgatt ctactctgg tatcatcctg aaagcgatgg tattccgtc ttccatgttc    1140 accgtcattt tcgcaatggc acgtaccgtt ggctggatcg cccactggag cgaaatgcac   1200
agtgacggta tgaagattgc ccgtccgcgt cagctgtata caggatatga aaaacgcgac   1260
tttaaaagcg atatcaagcg ttaa                                          1284

<210> SEQ ID NO 165
<211> LENGTH: 427
<212> TYPE: PRT
<213> ORGANISM: Escherichia coli

<400> SEQUENCE: 165

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
            20                  25                  30

Arg Thr Leu Gly Ser Lys Gly Val Phe Thr Phe Asp Pro Gly Phe Thr
        35                  40                  45

Ser Thr Ala Ser Cys Glu Ser Lys Ile Thr Phe Ile Asp Gly Asp Glu
```

```
                50                  55                  60
Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Thr Val Thr Arg His Thr
                100                 105                 110

Met Ile His Glu Gln Ile Thr Arg Leu Phe His Ala Phe Arg Arg Asp
                115                 120                 125

Ser His Pro Met Ala Val Met Cys Gly Ile Thr Gly Ala Leu Ala Ala
            130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
                180                 185                 190

Ser Tyr Ala Gly Asn Phe Leu Asn Met Met Phe Ser Thr Pro Cys Glu
                195                 200                 205

Pro Tyr Glu Val Asn Pro Ile Leu Glu Arg Ala Met Asp Arg Ile Leu
            210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
                260                 265                 270

Leu Lys Met Leu Glu Glu Ile Ser Ser Val Lys His Ile Pro Glu Phe
            275                 280                 285

Val Arg Arg Ala Lys Asp Lys Asn Asp Ser Phe Arg Leu Met Gly Phe
290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
            355                 360                 365

Ile Leu Lys Ala Met Gly Ile Pro Ser Ser Met Phe Thr Val Ile Phe
            370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
                420                 425
```

RECOMBINANT HOST CELLS HAVING AN INCREASE IN BUOYANT DENSITY

CROSS-REFERENCE TO RELATED APPLICATION

This application claims priority to Indian Provisional Patent Application No. 441/DEL/2011 filed Feb. 21, 2011, currently pending.

FIELD OF THE INVENTION

The invention relates to the field of molecular biology, microbiology, industrial biotechnology and more particularly to recombinant peptide production.

BACKGROUND OF THE INVENTION

Efficient production of bioactive polypeptides and peptides is an important goal of the biomedical and biotechnology industries. Bioactive peptides and proteins are used as therapeutic and diagnostic agents in a variety of diseases such as diabetes (insulin), viral infections and leukemia (interferon), diseases of the immune system (interleukins), and red blood cell deficiencies (erythropoietin), to name a few. Additionally, large quantities of proteins and peptides are needed for various industrial applications including, but not limited to, pulp and paper industries, textiles, food industries, personal care and cosmetics industries, sugar refining, wastewater treatment, production of alcoholic beverages, and as catalysts for the generation of new pharmaceuticals.

In biomedical-related fields small peptides are sometimes used as linkers for the attachment of diagnostic and pharmaceutical agents to surfaces (see U.S. Pat. App. Pub. No. 2003/0185870 to Grinstaff et al. and U.S. Pat. No. 6,620,419 to Lintner, K.). In the field of personal care, small peptides have been used to couple benefit agents to body surfaces such as hair, skin, nail, and teeth (U.S. Pat. Nos. 7,220,405; 7,309,482; 7,129,326; 7,585,495 and 7,285,264; U.S. Pat. App. Pub. Nos. 2002/0098524; 2005/0112692; 2005/0226839; 2007/0196305; 2006/0199206; 2007/0065387; 2008/0107614; 2007/0110686; 2008/0280810; 2006/0171885; and 2008/0175798).

Peptides may be prepared by chemical synthesis or isolated from natural sources. However, these methods are often expensive, time consuming, and characterized by limited production capacity. The preferred method of producing large quantities of peptides or proteins is through the fermentation of recombinant microorganisms engineered to express a genetic construct encoding the peptide or protein of interest. However, recombinant microbial peptide production has a number of obstacles to overcome in order to be cost-effective. For example, peptides produced within a recombinant microbial host cell are often degraded by endogenous proteases, which decrease the yield and increase the cost of production. Additionally, microbial production of smaller peptides in high yield may be adversely affected by size and the amino acid composition of the peptide. This is especially evident when the peptide of interest is soluble under typical physiological conditions found within the production host.

One way to mitigate the difficulties associated with recombinantly producing a soluble peptide of interest (POI) is to produce it in an insoluble form that may accumulate within the host cell as an inclusion body. Soluble POIs may be produced as insoluble fusion proteins by coupling at least one peptidic tag that promotes insolubility (i.e., an inclusion body tag or "IBT") to the peptide of interest. Producing the peptide of interest in the form of inclusion bodies provides a convenient means to isolate the protein from other cellular components.

One of the difficulties associated with recombinant protein production is controlling the costs associated with processing the recombinant biomass to obtain the desired peptide or protein of interest. Processing steps may include harvesting cells by centrifugation (to "spin down") to recover the cells from the fermentation medium, lysis or homogenization to disrupt the cells to release the peptide, and the application of various separation methods to isolate the fusion polypeptide. Host cell modifications that aid in distinguishing polypeptides comprising POIs would further decrease the cost of POI recovery. Thus, cellular modifications that render any of these steps more rapid and/or easy to perform would be expected to reduce the cost and/or time associated with processing the recombinant host cells.

Altered expression of endogenous genes and/or the introduction of additional expressible genetic constructs may enhance recombinant peptide/protein production. Chen et al. (*Biotech Bioengin* (2004) 85 (5):463-474) disclose mutations affecting endogenous periplasmic proteases reported to increase recombinant antibody fragment accumulation in the *E. coli* periplasmic space. Further, although single gene knockout libraries are available for *E. coli* (Baba, T., et al., (2006) *Mol. Syst. Biol.* 2: article 2006.0008), down-regulating or disrupting specific genes or combinations of genes in *Escherichia* species that significantly effect heterologous peptide production and/or downstream processing are not as well known.

U.S. Pat. No. 7,662,587 to Cheng et al. discloses *Escherichia* host cells comprising a combination of knockout mutations to gcvA (encoding the glycine cleavage enzyme) and spr (encoding a suppressor of prc) that increased the amount of heterologous peptide produced within the modified host cell. U.S. Pat. Appl. Pub. No. 2010/0227361 to Chen et al. discloses a recombinant *Escherichia* host cell having a knockout mutation to gcvA, a knockout mutation to spr, and at least one mutation to a portion of the endogenous yejM gene.

Centrifugation is often included as at least one step when recovering the peptide of interest from the recombinant biomass. Rendering cells and/or inclusion bodies denser, larger or heavier than typical inclusion bodies could provide for easier and more rapid isolation. Faster flow rate could be used in continuous centrifugation to harvest cells producing denser inclusion bodies and subsequent washes of the inclusion bodies, which would lead to higher throughput in downstream processing.

One way of achieving this is to provide recombinant host cells having at least one modification that increases the buoyant density of the cell or inclusion bodies within the cell when synthesizing heterologous polypeptides and/or a relative increase in the buoyant density of the inclusion bodies formed within the modified host cell. Increases in buoyant density provides a relatively simple means to identify and obtain cells capable of producing increased amounts of insoluble heterologous protein and/or denser inclusion bodies comprising the heterologous protein.

However, the genetic modifications that one can introduce to a recombinant microbial host cell to increase the buoyant density of the cell or the buoyant density of an inclusion body formed within such a cell are not well understood. The problem to be solved is to provide a method to obtain recombinant host cells having at least one modification that enables more efficient isolation of recombinant polypeptides, including fusion polypeptides comprising the polypeptide of interest.

Increasing the buoyant density of the recombinant host cells or the density of the inclusion bodies produced by recombinant host cells should reduce the cost of isolating the polypeptide of interest. As such, an additional problem to be solved is to provide recombinant microbial host cells having one or more genetic modifications that increase the buoyant density of the cell or inclusion bodies produced within recombinant host cell and methods of using such modified microbial host cells to produce a polypeptide of interest.

SUMMARY OF THE INVENTION

A method to obtain recombinant microbial host cells having an increase in buoyant density is provided. Recombinant microbial host cells having at least one genetic modification increasing the buoyant density of the cell or inclusion bodies provided within the microbial host cell are provided as well as method of using such cells for the production of a polypeptide of interest.

In one embodiment, a method to obtain recombinant microbial cells having at least one genetic modification that increases the buoyant density of the recombinant microbial cell is provided comprising:
  a) providing a population of recombinant microbial cells, the recombinant microbial cells in the population comprising;
    i) at least one introduced genetic modification; and
    ii) a chimeric genetic construct encoding a polypeptide of interest;
  b) growing the recombinant microbial cells under suitable conditions whereby the polypeptide of interest is produced and accumulates within the recombinant microbial cells;
  c) fractionating the population of recombinant microbial cells grown in (b) by a density gradient centrifugation;
  d) isolating a subpopulation of the recombinant microbial cells from a fraction having a higher buoyant density; and
  e) optionally repeating steps (a) through (d).

Several genetic modifications were identified that increased the buoyant density of recombinant microbial cells. The identified genetic modifications increasing buoyant density may be introduced into other recombinant microbial host cells to increase buoyant density. In another embodiment, a method is provided comprising:
  a) providing a recombinant microbial cell comprising a chimeric genetic construct encoding a polypeptide of interest; and
  b) introducing a genetic modification comprising:
    i) increasing expression of a gene encoding a polypeptide selected form the group consisting of GlyS, GlyQ, YsaB or a combination thereof;
    ii) decreasing or eliminating expression of gltA encoding citrate synthase; or
    iii) a combination of (i) and (ii); and
  c) growing the recombinant microbial cell of (a) under conditions whereby the polypeptide of interest is produced in the form inclusion bodies; wherein the presence of the genetic modification introduced in step (b) increases the buoyant density of the recombinant microbial cell.

In another embodiment, a recombinant *Escherichia* host cell is provided, comprising:
  a) a chimeric gene encoding a polypeptide of interest; wherein the peptide of interest is not GlyS, GlyQ, or YsaB; and
  b) a genetic modification that increases expression of at least one endogenous gene selected from the group consisting of the g/yS, glyQ, ysaB, or a combination thereof.

In another embodiment, a recombinant *Escherichia* host cell is provided, comprising:
  a) a chimeric genetic construct encoding a polypeptide of interest; and
  b) a knockout mutation in gene gltA (encoding citrate synthase).

In another embodiment, a method of producing a polypeptide of interest in a recombinant *Escherichia* host cell is provided comprising:
  a) providing a recombinant *Escherichia* host cell comprising
    i) at least one chimeric genetic construct encoding a polypeptide of interest; and
    ii) a knockout mutation in the endogenous gltA gene encoding citrate synthase;
  b) growing the *Escherichia* host cell of (a) to produce the polypeptide of interest; and
  c) recovering the polypeptide of interest produced in step (b).

In another embodiment, the polypeptide of interest in the above compositions and methods is produced in the form of an insoluble fusion protein comprising at least one inclusion body tag, wherein the fusion protein optionally comprises a peptide spacer separating said at least one inclusion body tag from the peptide/polypeptide of interest.

DESCRIPTION OF THE FIGURES

FIGS. 2(a-d). Images of centrifuge tubes showing separation of uninduced QC1525 cells (FIG. 2a; arrow 1) and induced QC1525 *E. coli* cells producing HC415 peptide tagged to inclusion body tag (IBT139) in large scale density gradient centrifugation 3.5 hours after induction (FIG. 2b; arrow 2), 21.5 hours after induction (FIG. 2c; arrows 3, 4, and 5), and 24 hours after induction (FIG. 2d; arrows 6, 7, and 8).

FIG. 6b) is circled and corresponds to the peptide of interest from the control. Lane 8 is the peptide of interest (circled) from band 8 in colony 181 (FIG. 6e; band 8). Note the increase in the approximately 28 kDa peptide of interest in lane 8 compared to lane 3. A SeeBlue Plus 2 molecular weight ladder is shown in the far left lane.

FIG. 8. Image of micro-density gradient centrifugation of selected isolates (F1, B3, C6, F1, A12, B11, D2, and E4) from density gradient sorting of the Keio collection strains. Top panel is the whole cells (WC) and bottom panel is the inclusion bodies (IB). The control is labeled BW. Note the increased buoyant density in isolates F1 and A12.

FIGS. 9(a-f). Images of various centrifuge tubes after density gradient centrifugation.

BRIEF DESCRIPTION OF THE BIOLOGICAL SEQUENCES

Figures 1A, 1B, 1C, 1D:
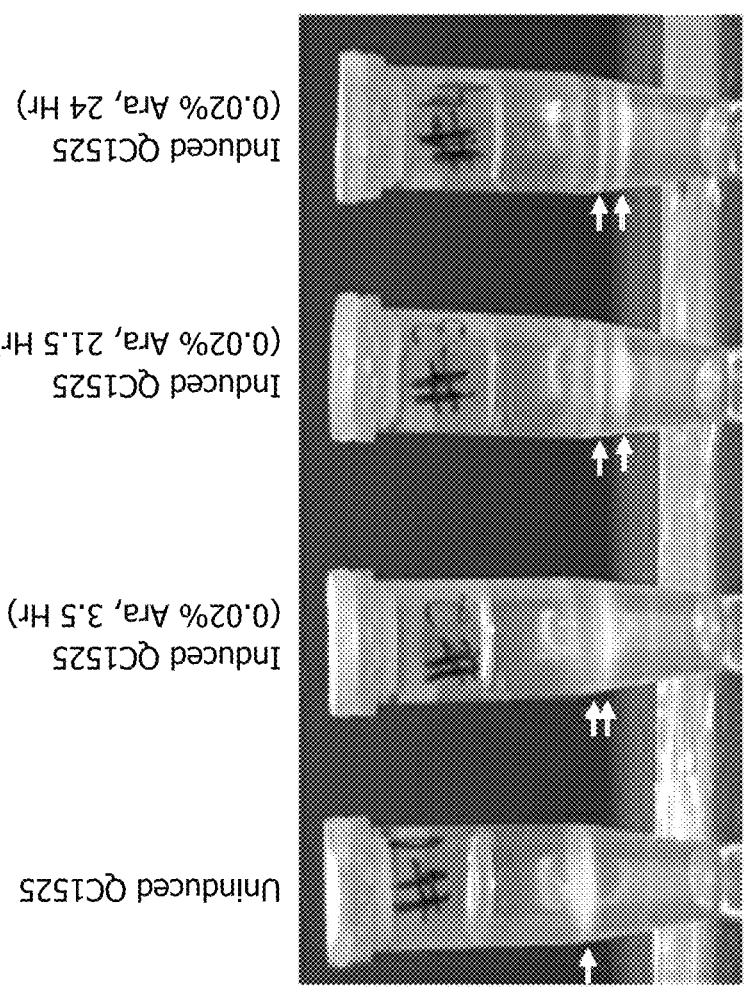
FIGS. 1(a-d). Separation of uninduced QC1525 cells (FIG. 1a) from induced QC1525 cells producing HC415 peptide tagged to inclusion body tag (IBT139) in small scale Percoll™ density gradient 3.5 hours after induction (FIG. 1b), 21.5 hours after induction (FIG. 1c), and approximately 24 hours after induction (FIG. 1d). Note appearance of 2 bands in induced cells (FIGS. 1b, 1c, and 1d), one upper band corresponding to the uninduced population (top arrows) and a lower band corresponding to the induced cells with greater buoyant density (lower arrows).

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

Sequences 1 to 125 are peptides having various target-binding functions. The targets include a variety of body surfaces (e.g., hair, skin, tooth, finger and toe nail, and the like), polymers and pigments. These peptides are provided as an illustrative but non-exhaustive list of examples of polypeptides of interests for incorporating into various heterologous fusion polypeptides that can accumulate in inclusion bodies.

SEQ ID NOs: 1-11 are the amino acid sequences of several hair-binding peptides.

SEQ ID NOs: 12-22 are the amino acid sequences of several skin-binding peptides.

SEQ ID NOs: 23-24 are the amino acid sequences of several nail-binding peptides.

SEQ ID NOs: 25-33 are the amino acid sequences of several tooth pellicle-binding peptides.

SEQ ID NOs: 34-44 are the amino acid sequences of several tooth enamel-binding peptides.

SEQ ID NOs: 45-51 are the amino acid sequences of several anti-microbial peptides.

SEQ ID NOs: 52-62 are the amino acid sequences of several clay-binding peptides.

SEQ ID NOs: 63-75 are the amino acid sequences of several calcium carbonate-binding peptides.

SEQ ID NOs: 76-82 are the amino acid sequences of several polypropylene-binding peptides.

SEQ ID NOs: 83-91 are the amino acid sequences of several polytetrafluoroethylene-binding peptides.

SEQ ID NOs: 92-98 are the amino acid sequences of several polyethylene-binding peptides.

SEQ ID NOs: 99-104 are the amino acid sequences of several nylon-binding peptides.

SEQ ID NOs: 105-107 are the amino acid sequences of several polystyrene-binding peptides.

SEQ ID NOs: 108-111 are the amino acid sequences of several cellulose acetate-binding peptides.

SEQ ID NOs: 112-115 are the amino acid sequences of several carbon black-binding peptides.

SEQ ID NOs: 116-120 are the amino acid sequences of CROMOPHTAL® yellow-binding peptides.

SEQ ID NOs: 121-125 are the amino acid sequences of several SUNFAST® magenta-binding peptides.

SEQ ID NOs: 126-139 are the amino acid sequences of several inclusion-body tags.

SEQ ID NO: 140 is the amino acid sequence of a tetracysteine peptide tag.

SEQ ID NO: 141 is the nucleic acid sequence of plasmid pLR199.

SEQ ID NO: 142 is the nucleic acid sequence of the polynucleotide encoding for fusion peptide IBT139-CCPGCC-HC124.

SEQ ID NO: 143 is the amino acid sequence encoding fusion peptide IBT139-CCPGCC-HC124.

SEQ ID NO: 144 is the nucleic acid sequence of plasmid pDCQ523.

SEQ ID NO: 145 is the nucleic acid sequence of a polynucleotide encoding fusion peptide IBT139(5C)-CCPGCC-HC415.

SEQ ID NO: 146 is the amino acid sequence of fusion peptide IBT139(5C)-CCPGCC-HC415.

SEQ ID NO: 147 is the nucleic acid sequence of a peptide linker.

SEQ ID NO: 148 is the nucleic acid sequence of araBAD promoter.

SEQ ID NO: 149 is the nucleic acid sequence encoding the SlyD protein.

SEQ ID NO: 150 is the amino acid sequence of the SlyD protein.

SEQ ID NO: 151 is the amino acid sequence of a caspase 3 cleavage site.

SEQ ID NO: 152 is the nucleic acid sequence of the approximately 2 Kb polynucleotide fragment comprising the ysaB, glyQ and partial glyS genes.

SEQ ID NO: 153 is the nucleic acid sequence encoding the YsaB protein.

SEQ ID NO: 154 is the amino acid sequence of the YsaB protein.

SEQ ID NO: 155 is the nucleic acid sequence encoding the GlyQ polypeptide.

SEQ ID NO: 156 is the amino acid sequence of the GlyQ polypeptide.

SEQ ID NO: 157 is the nucleic acid sequence encoding the complete GlyS polypeptide.

SEQ ID NO: 158 is the amino acid sequence of the GlyS polypeptide.

SEQ ID NO: 159 is the nucleic acid sequence of plasmid pDCQ601.

SEQ ID NO: 160 is the nucleic acid sequence encoding the partial GlyS protein.

SEQ ID NO: 161 is the amino acid sequence of the partial GlyS protein.

SEQ ID NO: 162 is the nucleic acid sequence of primer pBHR1F.

SEQ ID NO: 163 is the nucleic acid sequence of primer pBHR1R.

SEQ ID NO: 164 is the nucleic acid sequence encoding the E. coli GltA citrate synthase.

SEQ ID NO: 165 is the amino acid sequence of the E. coli GltA citrate synthase, which is deleted in Keio library knockout clone JWO710.

DETAILED DESCRIPTION OF THE INVENTION

The downstream processing of recombinant microbial biomass accounts for a substantial portion of the total cost to produce a peptide/polypeptide/protein of interest. Centrifugation is often included during the downstream purification process. Genetic modifications to the recombinant microbial cell (not including chimeric genetic construct encoding the peptide/protein of interest) that increase the buoyant density of the recombinant microbial cells or the inclusion bodies comprising the desired peptide/protein should reduce the cost to obtain the desired product.

A method to identify recombinant microbial cells having a genetic modification that increases the buoyant density of the cell or the buoyant density of inclusion bodies produced within the cell is provided herein. Recombinant microbial cells having at least one genetic modification that increases the buoyant density of the cell and/or inclusion bodies produced within the cell are provided as well as methods of using such cells for recombinant peptide/protein production.

The following definitions are used herein and should be referred to for interpretation of the claims and the specification. Unless otherwise noted, all U.S. Patents and U.S. Patent Applications referenced herein are incorporated by reference in their entirety.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "invention" or "present invention" is a non-limiting term and is intended to encompass all possible variations as described in the specification and recited in the claims.

As used herein, the terms "peptide", "polypeptide", and "protein" will be used interchangeably to refer to a chain of amino acids each of which is joined to the next amino acid by a peptide bond. In one aspect, this term also includes post translational modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

A heterologous polypeptide or peptide is one that the host cell would not normally be expected to synthesize absent some recombinant engineering manipulation that enables the host cell to do so.

As used herein, the terms "peptide of interest", "polypeptide of interest", "protein of interest" or "POI," refer to the desired heterologous peptide/polypeptide/protein product encoded by a recombinantly expressed gene. The peptide of interest may include any peptide/polypeptide product including, but not limited to proteins, fusion polypeptides/peptides, enzymes, peptides, polypeptides, and oligopeptides. In one embodiment, the peptide of interest ranges in size from 14 to 600 amino acids in length. The peptide of interest may be a bioactive peptide. The peptide of interest may have strong affinity for a target surface, such as a body surface. In one embodiment, the peptide of interest may have strong affinity for a surface. In another embodiment, the peptide of interest may have strong affinity for at least one body surface selected from the group consisting of hair, skin, nails, tooth, and tooth pellicle. In one embodiment, the peptide of interest is a single chain peptide from 14 to 600 amino acids in length and lacks any immunoglobulin folds or immunoglobulin subunits or fragments thereof.

As used herein, the terms "bioactive" or "peptide of interest activity" refer to the activity or characteristic associated with a peptide/polypeptide/protein of interest. The bioactive peptides may be used as, for example, curative agents for diseases (e.g., insulin, interferon, interleukins, anti-angiogenic peptides (U.S. Pat. No. 6,815,426); enzymes; polypeptides that bind to defined cellular targets such as receptors, channels, lipids, cytosolic proteins, and membrane proteins; peptides having antimicrobial activity; peptides having an affinity for a particular material (e.g., hair-binding polypeptides, skin-binding polypeptides, nail-binding polypeptides, tooth-binding peptides (include both tooth enamel and tooth pellicle-binding peptides), print media-binding peptides, cellulose-binding polypeptides, polymer-binding polypeptides, clay-binding polypeptides, calcium carbonate-binding peptides, cellulose acetate-binding peptides, carbon nanotube-binding polypeptides and peptides that have an affinity for particular animal or plant tissues) for targeted delivery of benefit agents.

As used herein, the "benefit agent" refers to a molecule that imparts a desired functionality or benefit when applied or coupled to a target surface. The benefit agent may be the polypeptide of interest or a peptide-based reagent coupled to benefit agent. The peptide-based reagent may be used to couple (covalently or non-covalently) a benefit agent to a target surface. The peptide reagent may couple a benefit agent to a body surface by forming a complex between the peptide reagent, the benefit agent, and the body surface. The benefit agent may be a particulate benefit agent (e.g., pigment, particles comprising an active agent) or may be a bioactive peptide, such as an enzyme.

As used herein, an "antimicrobial peptide" is a bioactive peptide having the ability to kill microbial cell populations (U.S. Pat. No. 7,427,656). Examples of antimicrobial peptides are provided as SEQ ID NOs: 45-51.

As used herein, the term "body surface-binding peptide" refers to a peptide having strong affinity for a body surface. Examples of body surfaces include, but are not limited to hair, skin, nail, and tooth. The body surface-binding peptides are typically used to couple a personal or health care benefit agent to the body surface. These agents include colorants, conditioners, antimicrobials, and enzymes, to name a few. Means to identify suitable body-surface binding peptides are well known in the art and may include biopanning techniques such as phage display, bacterial display, yeast display, ribosome display, and mRNA-display. The body surface-binding peptide may also be empirically-generated.

As used herein, "HBP" means hair-binding peptide. As used herein, the term "hair-binding peptide" refers to a peptide that binds with high affinity to hair. Examples of hair-binding peptides have been reported (U.S. Pat. App. Publication No. 2005-0226839 to Huang et al.; International Pub. No. WO 0179479; U.S. Pat. App. Pub. No. 2002-0098524 to Murray et al.; U.S. Pat. No. 7,129,326 to Janssen et al.; U.S. Pat. App. Pub. No 2006-0171885; U.S. Pat. Nos. 7,736,633; and 7,749,957). Examples of hair-binding peptides are provided as SEQ ID NOs: 1-11. The hair-binding peptides may be from about 7 amino acids to about 60 amino acids, more preferably, from about 7 amino acids to about 25 amino acids, most preferably from about 7 to about 20 amino acids in length.

As used herein, "SBP" means skin-binding peptide. As used herein, the term "skin-binding peptide" refers to a peptide sequence that binds with high affinity to skin. Examples of skin-binding peptides have also been reported (U.S. Pat. No. 7,309,482 to Buseman-Williams; U.S. Pat. Nos. 7,341, 604; and 7,749,957). Skin as used herein as a body surface will generally comprise a layer of epithelial cells and may additionally comprise a layer of endothelial cells. Examples of skin-binding peptides are provided as SEQ ID NOs: 12-22. The skin-binding peptides may be from about 7 amino acids to about 60 amino acids, more preferably, from about 7 amino acids to about 25 amino acids, most preferably from about 7 to about 20 amino acids in length.

As used herein, "NBP" means nail-binding peptide. As used herein, the term "nail-binding peptide" refers to a peptide that binds with high affinity to nail. Examples of nail-binding peptides have been reported (U.S. Pat. No. 7,749, 957). Examples of nail-binding peptides are provided as SEQ ID NOs: 23-24. The nail-binding peptides may be from about 7 amino acids to about 60 amino acids, more preferably, from about 7 amino acids to about 25 amino acids, most preferably from about 7 to about 20 amino acids in length.

As used herein, "TBP" means tooth-binding peptide. A tooth-binding peptide is a peptide that binds with high affinity to a mammalian or human tooth surface. As used herein, the term "tooth-binding peptide" will refer to a peptide that binds to tooth enamel or tooth pellicle. The tooth-binding peptides may be from about 7 amino acids to about 60 amino acids in length, more preferably, from about 7 amino acids to about 25 amino acids in length, most preferably from about 7 to about 20 amino acids in length. The tooth-binding peptides may be combinatorially-generated peptides. Examples of tooth-binding peptides having been disclosed in co-pending and co-owned U.S. Pat. App. Pub. 2008-0280810. Several examples of tooth-binding peptides and are provided as SEQ ID NOs: 25-44.

As used herein, the term "tooth surface" refers to a surface comprised of tooth enamel (typically exposed after professional cleaning or polishing) or tooth pellicle (a surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" will refer to the thin film (typically ranging from about 20 nm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will expose more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e., hydroxyapatite) along with water and some organic material. In one embodiment, the tooth surface is selected from the group consisting of tooth enamel and tooth pellicle.

As used herein, the terms "peptide linker", "linker", and "peptide spacer" refer to a peptide used to link together two or more peptides. Peptide linkers/spacers may be comprised of any naturally occurring amino acids and may range from 1 to 100 amino acids in length, 1 to 50 amino acids in length, 1 to 30 amino acids in length, and most preferably 3 to 30 amino acids in length. An example of a peptide linker is provided as SEQ ID NO: 147.

As used herein, the terms "cleavable linker element" and "cleavable peptide linker" are used interchangeably and refer to cleavable peptide segments typically incorporated between an inclusion body tag and the peptide of interest. After the inclusion bodies are separated and/or partially-purified or purified from the cell lysate, the cleavable linker element can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary. An example of an enzymatically cleavable peptide linker is provided by SEQ ID NO: 151 (Caspase-3 cleavage sequence). The cleavable linker may be an acid cleavable aspartic acid-proline dipeptide (D-P) moiety. The cleavable peptide linkers may be incorporated into the fusion proteins using any number of techniques well known in the art.

As used herein, a polymer-binding peptide is a peptide that binds with high affinity to a specified polymer (see, for example, U.S. Pat. No. 7,427,656). Examples of polymer-binding peptides may include, but are not limited to, polypropylene-binding peptide (SEQ ID NOs: 76-82), polytetrafluoroethylene-binding peptides (SEQ ID NOs: 83-91), polyethylene-binding peptides (SEQ ID NOs: 92-98), nylon-binding peptides (SEQ ID NOs: 99-104), and polystyrene-binding peptides (SEQ ID NOs: 105-107).

As used herein, a clay-binding peptide is a peptide that binding with high affinity for a clay. Examples of clay-binding peptides include SEQ ID NOs: 52-62.

As used herein, a calcium carbonate-binding peptide is a peptide that binding with high affinity to calcium carbonate. Examples of calcium carbonate-binding peptides include SEQ ID NOs: 63-75.

As used herein, a cellulose acetate-binding peptide is a peptide that binds with high affinity to cellulose acetate. Examples of cellulose acetate-binding peptide are provided as SEQ ID NOs: 108-111.

As used herein, a pigment-binding peptide is a peptide that binds with high affinity for a specified pigment. Examples may include, but are not limited to, carbon black-binding peptides (SEQ ID NOs: 112-115), CROMOPHTAL® yellow-binding peptides (SEQ ID NOs: 116-120), and SUNFAST® magenta-binding peptides (SEQ ID NOs: 121-125).

As used herein, the terms "coupling" and "coupled" refer to any chemical association and may include both covalent and non-covalent interactions in one coupling event. Coupling may also refer to separate, individual covalent interaction or separate, individual non-covalent interaction.

As used herein, a "tetracysteine tag" is a peptide tag having an effective number cysteine residues (typically 4) which are capable of binding a biarsenical labeling agent (U.S. Pat. No. 7,794,963; incorporated herein by reference). An example of a tetracysteine tag is provided as SEQ ID NO: 140.

As used herein, the terms "solubility tag" and "inclusion body tag" and the abbreviation "IBT" refer to a polypeptide that promotes or enhances the formation of inclusion bodies when fused to a peptide/polypeptide of interest. The polypeptide of interest, i.e. POI, may be soluble within the host cell and/or host cell lysate when not fused to an inclusion body tag. Fusion of the polypeptide of interest to the inclusion body tag produces a fusion protein that agglomerates into intracellular bodies, also called inclusion bodies, within the host cell. The fusion protein comprises a portion having an inclusion body tag and a peptide/protein of interest. The polypeptide/protein of interest may be separated from the inclusion body tags using cleavable peptide linker elements (See U.S. Pat. Nos. 7,732,569, 7,662,913, and 7,678,883; each incorporated herein by reference). Examples of inclusion body tags include, but are not limited to, SEQ ID NOs: 126-139.

The inclusion body tag(s) and the peptide of interest may exhibit a different solubility in a defined medium, typically aqueous, thereby facilitating separation of the inclusion body tag from the peptide of interest. Preferably, the inclusion body tag is insoluble in an aqueous solution while the protein/peptide of interest is appreciably soluble in an aqueous solution. The pH, temperature, and/or ionic strength of the aqueous solution can be adjusted to facilitate recovery of the peptide of interest. The differential solubility between the inclusion body tag and the polypeptide of interest may occur in an aqueous solution having a pH of 5 to 10 and a temperature range of 15° C. to 50° C.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, an expression cassette, a vector, a plasmid and the like.

As used herein, the term "endogenous gene" refers to a native gene in its natural form and location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

As used herein, the term "*Escherichia*" refers to a genus of Gram-negative, non-spore forming, facultatively anaerobic, rod-shaped bacteria from the family Enterobacteriaceae. The genus *Escherichia* include various species, such as *Escherichia coli*. The *Escherichia* host cell is an *Escherichia coli* cell. The *Escherichia coli* cell may be derived from an *Escherichia coli* K-12 strain.

As used herein, the terms "fusion protein" and "fusion peptide" are interchangeable and refer to a polymer of amino acids (peptide, oligopeptide, polypeptide, or protein) comprising at least two portions, each portion comprising a distinct function. A first portion of the fusion peptide may comprise at least one inclusion body tag and a second portion of the fusion peptide may comprise at least one peptide of interest. The fusion protein may additionally include at least one cleavable peptide linker that facilitates chemical and/or enzymatic cleavage and separation of the inclusion body tag(s) and the peptide(s) of interest.

As used herein, the term "immunoglobulin fold" refers to a common all-β protein fold that consists of a 2-layer sandwich of ~7 antiparallel β-strands arranged in two β-sheets. The backbone switches repeatedly between the two β-sheets. Typically, the pattern is (N-terminal β-hairpin in sheet 1)-(β-hairpin in sheet 2)-(β-strand in sheet 1)-(C-terminal β-hairpin in sheet 2). The cross-overs between sheets form an "X", so that the N- and C-terminal hairpins are facing each other.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |

-continued

| Amino Acid | Three-Letter Abbreviation | One-Letter Abbreviation |
|---|---|---|
| Serine | Ser | S |
| Threonine | Thr | T |
| Tryptophan | Trp | W |
| Tyrosine | Tyr | Y |
| Valine | Val | V |
| Miscellaneous (or as defined herein) | Xaa | X |

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). The definition of "operably linked" may also be extended to describe the products of chimeric genes. As such, "operably-linked" may also refer to the linking of two or more peptides/polypeptides by at least one peptide linker.

Polynucleotides encoding heterologous polypeptides may be operably linked to various known promoters, specifically encompassing non-inducible and inducible promoters. Suitable promoters exist for virtually all cell types, including mammalian and microbial cell types. Thus, it is well known in the art that both types of promoters that are suitable for heterologous polypeptide expression in bacteria, yeast, fungi, and mammalian cells are commonly used to provide suitably high levels of synthesis of a polypeptide of interest.

Examples of inducible promoters suitable for inducing the expression of the polynucleotide encoding the heterologous polypeptide may include the β-lactamase and lactose promoter systems (Chang et al., *Nature*, (1978) 275: 615; Goeddel et al., *Nature*, (1979) 281: 544), the arabinose promoter system (Guzman et al., *J. Bacteriol.*, (1992) 174: 7716-7728), alkaline phosphatase, a tryptophan (trp) promoter system (Goeddel, *Nucleic Acids Res.*, (1990)8: 4057 and EP 36,776) and hybrid promoters such as the tac promoter (deBoer et al., *Proc. Natl. Acad. Sci. USA*, (1983) 80: 21-25). However, persons of ordinary skill in the art are clearly aware of the numerous non-inducible and inducible promoters are available and have the means to construct the corresponding gene expression cassettes tailored for their systems. For example, the nucleotide sequences of non-inducible and inducible promoters for numerous microbial and mammalian species have been published, thereby enabling a skilled worker to ligate them operably to any DNA encoding a polypeptide of interest, using restriction enzymes or, if necessary, linkers or adaptors or polymerase chain reaction (i.e., PCR) to supply any required restriction sites.

Density Gradient Centrifugation

As used herein, the terms "density gradient centrifugation" and "equilibrium density gradient centrifugation" will be used to describe a technique to separate cellular components on the basis of their buoyant density. A mixture of components is centrifuged through a steep density gradient. The density gradient medium often contains a high concentration of sucrose, or more often, cesium chloride (CsCl). In these gradients, the molecules being studied have a density somewhere in between the highest and lowest densities generated in the gradient. The components of the sample begin to move down this gradient until a point is reached where the density of the solution is equal to the individual components density. The component then stops moving further and forms a distinct band. The position of the band in the tube is characteristic of the buoyancy of that component. Buoyancy, or buoyant density of a substance is its tendency to float in a medium, which in this case is the density gradient.

The isolation of either the cells containing the inclusion bodies or the inclusion bodies that formed therein may be conveniently performed by density gradient centrifugation using a gradient medium selected from the group consisting of PERCOLL™, FICOLL™, metrizamide, sucrose or cesium chloride. PERCOLL™ is a preferred medium but others can be adapted for the relevant purposes encompassed by the methods disclosed herein. As described in the Examples, removal from the density gradient after centrifugation of either cells or inclusion bodies can be achieved with the use of conventional pipetting devices.

The components with a mixture are separated/fractionated within the density gradient based on their respective buoyant density, forming distinct bands within the centrifuge tube. As used herein, the term "fractionating" will be used to describe the step of performing equilibrium density gradient centrifugation whereby a population of cells or inclusion bodies having different buoyant densities is separated into subpopulations based on differences in buoyant density. Recombinant microbial cells and/or inclusion bodies produced by such cells can be fractionated based on their respective buoyant density. Bands corresponding to relative higher buoyant density can be collected and the process can be repeated to obtain cells and/or inclusion bodies produce by such cells having higher buoyant density.

The genetic modification associated with the increase in buoyant density identified by the present methods can be introduced into other microbial production hosts. Through repeated genetic modification and selection, one can obtain 1) modified microbial host cells having even higher buoyant density or 2) modified microbial host cells capable producing inclusion bodies having increased buoyant density.

Introducing Genetic Modifications to Increase Buoyant Density

Provided herein is a method to identify a genetic modification that increases the buoyant density of a recombinant microbial cell and/or an inclusion body produced by a recombinant microbial cell. In one embodiment, the introduced genetic modification increases the buoyant density of the recombinant microbial cell. In another embodiment, the introduced genetic modification increases the buoyant density of the inclusion body. In one aspect, the buoyant density of the inclusion body increases without increasing the amount of POI in the inclusion body (i.e., denser inclusion bodies formed). In a further embodiment, the introduced genetic modification increases the buoyant density of the recombinant microbial cell comprising at least one inclusion body (comprising the polypeptide of interest).

The present genetic modifications are modifications in addition to the chimeric genetic construct designed to recombinantly express a polypeptide of interest. As such, the introduced genetic modification does not include chimeric genetic construct producing the desired polypeptide of interest. Conversely, the desired polypeptide of interest (POI) will not include, by proviso, the protein encoded by ysaB, glyQ, glyS, a truncated glyS or any combination thereof.

The introduced genetic modification may include recombinant expression of an introduced polynucleotide, decreased or disrupted expression of an endogenous gene or a combination there.

Recombinant Expression of a Polynucleotide to Increase Buoyant Density

Described herein are compositions and methods for increasing the buoyant density of a microbial cell or inclusion body produced by a microbial cell by expressing or over-expressing a polynucleotide encoding ysaB, glyQ, glyS, a truncated glyS or any combination thereof. In one embodiment, the source of the polynucleotide comprising ysaB, glyQ, glyS or a truncated glyS is *Escherichia*. In a further embodiment, the source of polynucleotide is *Escherichia coli*. In a preferred embodiment, the source of the polynucleotide is *Escherichia coli* BL21.

In one embodiment, the recombinantly expressed polynucleotide used to increase buoyant density encodes the YsaB protein having the amino acid sequence SEQ ID NO: 154. In one aspect, the polynucleotide comprises the nucleic acid sequence SEQ ID NO: 153.

In one embodiment, the recombinantly expressed polynucleotide used to increase buoyant density encodes the GlyQ protein having the amino acid sequence SEQ ID NO: 156. In one aspect, the polynucleotide comprises the nucleic acid sequence SEQ ID NO: 155.

In one embodiment, the recombinantly expressed polynucleotide used to increase buoyant density encodes the complete GlyS protein having the amino acid sequence SEQ ID NO: 158. In one aspect, the polynucleotide comprises the nucleic acid sequence SEQ ID NO: 157.

In one embodiment, the recombinantly expressed polynucleotide used to increase buoyant density encodes a truncated GlyS protein having the amino acid sequence SEQ ID NO: 161. In one aspect, the polynucleotide comprises the nucleic acid sequence SEQ ID NO: 160.

In one embodiment, the recombinantly expressed polynucleotide used to increase the buoyant density encodes the combination of proteins comprising amino acid sequences SEQ ID NOs: 154, 156, and 161. In yet a further aspect, the polynucleotide used to increase the buoyant density comprises nucleic acid sequence SEQ ID NO: 152.

Screening a Genomic Library

As exemplified herein, a genomic library having DNA fragments ranging from about 2 kb to about 3 kb was prepared. The present method may use larger or smaller DNA fragments, however, an average size of 1 kb to 4 kb is preferred. The random fragments were inserted into an expression vector. The vector was introduced into recombinant microbial host cells comprising a chimeric genetic construct encoding a polypeptide of interest. The recombinant microbial cells were grown under conditions whereby the introduced polynucleotide from the genomic library and the chimeric gene encoding the polypeptide of interest were expressed. The polypeptide of interest accumulated within the cells in the form of inclusion bodies. The inserted DNA fragment may be expressed by operably linking the fragment to suitable regulatory sequence or may have its own regulatory sequence capable of expression within the recombinant microbial host cell.

The population of cells comprising the genomic inserts and the polypeptide of interest were then fractioned using density gradient centrifugation. Subpopulations of cells exhibiting higher buoyant density were selected. The subpopulation exhibiting an increase in buoyant density can be obtained after the first fractionation. In one embodiment, the process may be repeated to obtain recombinant microbial cells and/or inclusion bodies having even higher buoyant densities.

The genomic DNA used to prepare the genomic library may be obtained for any source organism. In one embodiment, the genomic DNA library is prepared from a microbial cell is selected from the group consisting of *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, the source of the genomic DNA used to prepare the library is *Escherichia*. Preferably the source is *Escherichia coli*. In another embodiment, the source may be derived from *Escherichia coli* BL21.

Method to Obtain Recombinant Microbial Cells Having Genetic Modifications which Increase Buoyant Density The process exemplified herein may be repeated to obtain cells having further increases buoyant density. The process may be used to screen libraries of mutants to identify further genetic modifications that may increase the buoyant density of the cells and/or inclusion bodies produced by the modified cells.

As such, a method to obtain recombinant microbial cells having at least one genetic modification that increases the buoyant density of the recombinant microbial cell is provided herein comprising:
  a) providing a population of recombinant microbial cells, the recombinant microbial cells in the population comprising;
    i) at least one introduced genetic modification; and
    ii) a chimeric genetic construct encoding a polypeptide of interest;
  b) growing the recombinant microbial cells under suitable conditions whereby the polypeptide of interest is produced and accumulates within the recombinant microbial cells;
  c) fractionating the population of recombinant microbial cells grown in (b) by a density gradient centrifugation;
  d) isolating a subpopulation of the recombinant microbial cells from a fraction having a higher buoyant density; and
  e) optionally repeating steps (a) through (d).

Decreased or Disrupted Expression of Endogenous Genes to Increase Buoyant Density As used herein, the terms "disrupted functional expression", "disrupted expression", and "disrupted gene" refer to a genetic modification to a specified gene that stops functional expression of the gene's product, such as an active enzyme, functional RNA, and/or functional regulatory protein. Generally, disruption in the production a gene product can be accomplished by, for example, an insertion, deletion, or substitution to a portion of the gene, which results in no formation or reduced formation of the active gene product. The disruption may preferably be a partial or complete deletion of the gene. A genetic modification that complete abolishes production of the gene product may be referred to as a "knockout" and may be denoted by the symbol "Δ". For example, "ΔgltA" would refer to a knockout of the gltA gene that complete disrupted production of a functional GltA protein.

When the sequence of the gene to be disrupted is known, down regulating gene expression may be accomplished by targeted gene disruption and involves creating genetic cassettes that includes DNA to be inserted into the to-be-disrupted gene. This DNA is often a genetic marker and is flanked by sequence(s) having a high degree of homology to a portion of the targeted gene. Introduction of the cassette into the host cell results in insertion of the foreign DNA into the targeted gene via native DNA replication mechanisms of the cell (Hamilton et al., *J. Bacteriol.*, 171:4617-4622 (1989); Balbas et al., *Gene*, 136:211-213 (1993); Gueldener et al., *Nucleic Acids Res.*, 24:2519-2524 (1996); and Smith et al., *Methods Mol. Cell. Biol.*, 5:270-277 (1996)) and interferes with transcription of the targeted gene, which produces no mRNA transcripts from which to translate a gene product.

Down regulation of expression does not require completely eliminating all expression of the gene and its corresponding gene product. Targeted genes may be down-regulated using several other techniques known in the art. For example, target genes can be modified to be under the control of non-native promoters. When desired that a pathway and/or functional gene product operate at a particular point in a cell cycle or during a fermentation run, regulated or inducible promoters can replace the native promoter of the target gene. Similarly, the native or endogenous promoter can be modified to decrease gene expression. For example, endogenous promoters can be altered in vivo by mutation, deletion, and/or substitution (see, U.S. Pat. No. 5,565,350 to Kmiec, Eric B.).

Down regulating can involve antisense technology when the sequence of the target gene is known. Here, a nucleic acid segment from the desired gene is cloned and operably linked to a promoter such that the anti-sense strand of RNA will be transcribed. This construct is then introduced into the host cell and the antisense strand of RNA is produced, which inhibits gene expression by preventing the accumulation of mRNA. Antisense technology is within the skill of the art. That is, a skilled artisan understands that achieving a down-regulated expression through antisense genes involves the use of chimeric genes having various regulatory elements.

Besides targeted gene disruption and antisense technology, other down regulation methods exist that do not require knowing the sequence of the to-be-disrupted gene. For example, cells may be exposed to UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., (hereinafter "Brock") or Deshpande, Mukund V., *Appl. Biochem. Biotechnol.*, 36:227 (1992) (hereinafter "Deshpande").

Transposon mutagenesis represents another non-specific method of gene disruption and is exemplified herein. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid molecule in the presence of the transposase, the transposable element will randomly insert into the nucleic acid molecule. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Exemplified herein is a method of increasing the buoyant density of a recombinant microbial cell and/or inclusion body produced by a recombinant microbial cell by decreasing or disrupting expression the gene gltA (encoding citrate synthase).

In one aspect, the endogenous copy of gltA is a knockout mutation. In a preferred aspect, the recombinant microbial host cell comprising the decreased or disrupted expression of gltA is a genetically engineered *Escherichia* cell expressing a chimeric gene encoding a polypeptide of interest (POI).

Methods to Identify Substantially Similar Nucleic Acid Sequences Associated with Increasing Buoyant Density Nucleic acid hybridization may also be used to identify substantially similar nucleic acid molecules to those reported herein to increase buoyant density. The present nucleic acid molecules described herein may be used to identify genes encoding substantially similar polypeptides/proteins expected to have similar function (increased buoyant density). Nucleic acid hybridization may be conducted under stringent conditions. Substantially similar sequences are defined by their ability to hybridize, under the following stringent conditions (0.1×SSC, 0.1% SDS, 65° C. and washed with 2×SSC, 0.1% SDS followed by 0.1×SSC, 0.1% SDS, 65° C.).

Each of the proposed modifications is well within the routine skill in the art (see Sambrook, J. and Russell, D., *Molecular Cloning: A Laboratory Manual*, Third Edition, Cold Spring Harbor Laboratory Press, Cold Spring Harbor, N.Y. (2001)). Moreover, the skilled artisan recognizes that substantially similar sequences are also encompassed by the present invention. Furthermore, the genetic modifications illustrated herein in *Escherichia coli* should apply to other members of the genus *Escherichia*.

As illustrated herein, the *Escherichia* host cell may also have a knockout to the endogenous chromosomal araBAD operon (a pBAD expression vector and arabinose induction was used to drive expression of the chimeric gene encoding the fusion peptide) and a knockout to the slyD gene (to remove possible binding between the LUMIO™ biarsenical labeling reagent and cysteine rich sequences in slyD). The recombinant *Escherichia* production host may comprise decreased expression and/or a disruption (such as a knockout) in the endogenous araBAD operon, the slyD gene, or a combination thereof (in addition to the genetic modification increasing buoyant density).

Peptide/Polypeptide of Interest

The function of the peptide of interest is not limited by the present method and may include, but is not limited to bioactive molecules that act as curative agents for diseases, such as insulin, interferon, interleukins, peptide hormones, immunoglobulins, antibodies, anti-angiogenic peptides, active enzymes, and peptides that bind to and affect defined cellular targets such as receptors, channels, lipids, cytosolic proteins, and membrane proteins (see U.S. Pat. No. 6,696,089); peptides having an affinity for a particular material, such as biological tissues, biological molecules, hair-binding peptides (see U.S. patent application Ser. No. 11/074,473; Intl Pat. App. No. WO 0179479; U.S. Pat. App. Pub. No. 2002/0098524; U.S. Pat. App. Pub. No. 2003/0152976; Intl Pat. App. No. WO 04048399; U.S. Pat. App. Pub. No 2007/0067924; and U.S. Pat. App. Pub. No. 2007/0249805), skin-binding peptides (see U.S. Pat. No. 7,309,482; Intl. Pat. App. No. WO 2004/000257; and U.S. Pat. App. Pub. No. 2007/0249805), nail-binding peptides (see U.S. Pat. App. Pub. No. 2007/0249805), cellulose-binding peptides, polymer-binding peptides (see U.S. Pat. App. Pub. Nos. 2007/0141629, 2007/0264720, 2008/0207872, 2007/0141628, and 2007/0261775), clay-binding peptides for targeted delivery of at least one benefit agent (see U.S. patent application Ser. No. 10/935,642; U.S. patent application Ser. No. 11/074,473; and U.S. Pat. App. Pub. No. 2007/0249805).

The peptide of interest may be a single chain peptide ranging in size from about 14 to about 600 amino acids in length and lacks an immunoglobulin fold. The peptide of interest may range in size from 14 to 400 amino acids in length, 14 to 300 amino acids in length, or 14 to about 200 amino acids in length.

The heterologous polypeptide of interest can be a polypeptide that may accumulate in inclusion bodies upon culturing a recombinant cell comprising a heterologous polypeptide-encoding polynucleotide operably linked to a promoter, to synthesize the heterologous polypeptide. The heterologous polypeptide of interest may be integrated into chromosome of production host and synthesized from chromosome, or it could be synthesized from expression plasmids present in production host. The polypeptide of interest may be produced in the form of an insoluble fusion protein. The fusion protein may include at least one peptidic solubility tag (inclusion body tag; "IBT") to enhance accumulation of the fusion protein as inclusion bodies. Inclusion body tags are exemplified herein and in other patent applications and issued patents that are incorporated by reference. Example of inclusion body tags are provided by SEQ ID NOs: 126-139.

In general, the polypeptide can be composed of two or preferably three, segments; the IBT, the POI and optionally but preferably a peptide linker that joins the IBT and POI to each other. It is irrelevant which of the IBT or POI is positioned at the amino-terminal portion and carboxyl-terminal portion of the heterologous fusion polypeptide and vice versa.

In one embodiment, the fusion peptide may be comprised of at least one solubility tag, such as an inclusion body tag. The fusion peptide/polypeptide/protein may have the general form of:

IBT-CL-POI
or
POI-CL-IBT
wherein;
IBT=at least one inclusion body tag;
CL=at least one cleavable peptide linker; and
POI=the polypeptide of interest.

When using a cleavage peptide linker, it is preferable that the peptide linker have an enzymatic and/or chemically cleavable site. With this in mind, a linker may be designed to have any recognition and cleavage site that corresponds to the many known proteases that have been purified; such as trypsin, proteinase K, a Caspase such as Caspase 3, and the like. An example of a Caspace-3 cleavage sequence is provided as SEQ ID NO: 151.

It is similarly desirable to have one or more chemically sensitive cleavage sites on the linker that, preferably, does not also cleave the IBT and POI. A convenient chemical sensitivity is pH cleavage of the linker, more specifically, low pH. Such acid-cleavable sites may be comprised of one or more aspartic acid-proline, i.e., DP, pairs. In such embodiments of the inventive method, the pH range at which cleavage of the linker occurs is between about pH 1 to about pH 6, preferably from about pH 2 to about pH 5 and most preferably between about pH 2 to about pH 4.

The applicability of the method is broad with respect to cell type. Therefore, virtually any recombinant host cell capable of synthesizing suitable amounts of a heterologous polypeptide such that the synthesized heterologous polypeptide accumulates in inclusion bodies may be used. In a preferred embodiment, the recombinant host cell is a recombinant microbial host cell, such as yeast, fungi and bacteria. In one embodiment, the recombinant microbial cell is selected from the group consisting of *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. The more preferred cell types for use in the method are *Saccharomyces* sp., *Salmonella* sp., *Bacillus* sp. and *Escherichia* sp. Even more preferred is *Escherichia coli*.

Single Chain Peptides Having Affinity for a Target Surface

Proteinaceous materials having strong affinity for a body surface can target delivery of one or more personal care benefit agents. Some of these materials comprise or derive from immunoglobulins or immunoglobulin fragments (antibodies, antibody fragments, $F_{ab}$, single-chain variable fragments (scFv), and Camelidae $V_{HH}$) having affinity for the target surface. Other such proteinaceous materials comprise non-immunoglobulin derived scaffold proteins. Further, these materials for delivery of a personal care benefit agent can include a single chain, linear peptide.

The peptide of interest used in the fusion proteins described herein may be proteinaceous material that has at least one domain having strong affinity for a target surface but does not comprise an immunoglobulin fold or underlying scaffold support. Thus, the POI preferably comprises at least one single chain peptide. Moreover, the peptide of interest described herein is heterologous to the recombinant microbial host cell and may be produced in the cytoplasm and not targeted for secretion and/or accumulation in the periplasm.

Single-chain peptides that target surfaces can be identified and isolated from peptide libraries using any number of biopanning techniques well known to those skilled in the art including, but not limited to bacterial display, yeast display, combinatorial solid phase peptide synthesis, phage display, ribosome display, and mRNA display. Techniques to generate random peptide libraries are described in Dani, M., *J. of Receptor & Signal Transduction Res.*, 21(4):447-468 (2001). Phage display libraries are available commercially from companies such as New England BioLabs (Beverly, Mass.).

The peptide of interest may be a peptide-based reagent comprising a plurality of biopanned target surface-binding peptides coupled together (optionally through one or more spacers) to form at least one target surface binding domain. The peptide of interest may comprise multiple target surface-binding domains, wherein each domain may have affinity for the same or a different target surface. The individual biopanned target surface-binding peptides are typically about 7 to about 60 amino acids in length and often have a binding affinity (as measured or reported as an $MB_{50}$ or $K_D$ value) of $10^{-5}$ M or less for the surface of the target material. The individual biopanned target surface-binding peptides may be from about 7 amino acids to about 60 amino acids in length, more preferably, from about 7 amino acids to about 25 amino acids in length, most preferably from about 7 to about 20 amino acids in length. The peptide of interest may also be a an individual target surface-binding peptide.

Examples of single chain peptide-based reagents having affinity for at least one target surface include, but are not limited to body surfaces such as hair, skin, nail, and teeth (U.S. Pat. Nos. 7,220,405; 7,309,482; and 7,285,264; U.S. Pat. App. Pub. Nos. 2005/0226839; 2007/0196305; 2006/0199206; 2007/0065387; 2008/0107614; 2007/0110686; and 2006/0073111; and Intl Pat. App. Pub. Nos. WO2008/054746; WO2004/048399, and WO2008/073368) as well as other surfaces such as pigments and miscellaneous print media (U.S. Pat. App. Pub. No. 2005/0054752), and various polymers such as polymethyl methacrylate (U.S. Pat. App. Pub. No. 2007/0265431), polypropylene (U.S. Pat. App. Pub. No. 2007/0264720), nylon (U.S. Pat. App. Pub. Nos. 2007/0141629 and 2003/0185870), polytetrafluoroethylene (U.S. patent application Ser. No. 11/607,734), polyethylene (U.S. Pat. App. Pub. No. 2007/0141628), and polystyrene (U.S. Pat. App. Pub. No. 2007/0261775). Examples of various target surface-binding peptides are provided in the present sequence listing.

The target surface-binding peptide may have strong affinity for a particulate benefit agent surface (such as a pigment, a sunscreen agent, a whitening agent, etc.), a polymeric coating applied to a particulate benefit agent (such as a coated pigment), a clay, calcium carbonate or a body surface.

Binding Affinity

The term "$MB_{50}$" refers to the concentration of the binding peptide that gives a signal that is 50% of the maximum signal obtained in an ELISA-based binding assay (see present Example 11 and U.S. Published Patent Application No. 2005-0226839). The $MB_{50}$ value provides an indication of the strength of the binding interaction or affinity of the components of the complex. The lower the $MB_{50}$ value, the stronger the interaction of the peptide with its corresponding substrate. The term "binding affinity" refers to the strength of the interaction of a binding peptide with a given substrate. The binding affinity is defined herein in terms of the $MB_{50}$ value, determined in an ELISA-based binding assay.

Peptides having an affinity for a target surface (i.e., target surface-binding peptides) may be selected using combinatorial methods that are well known in the art or may be empirically generated. It is preferred that the polypeptide of interest having affinity for a target surface has a binding affinity as measured by $MB_{50}$ values, of less than or equal to about $10^{-5}$ M, more preferably less than or equal to about $10^{-6}$ M, even more preferably less than or equal to about $10^{-7}$ M, and even more preferably less than or equal to about $10^{-8}$ M.

In one embodiment, the term "high affinity" or "strong affinity" will be used to describe a binding affinity, as measured by an $MB_{50}$ value, less than or equal to about $10^{-5}$ M, preferably less than or equal to about $10^{-6}$ M, more preferably less than or equal to about $10^{-7}$ M, and even more preferably less than or equal to about $10^{-8}$ M.

Microbial Host Cells

Transcription, translation, and the protein biosynthetic apparatus are universal genetic processes. Examples of microbial production hosts may include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferably, the microbial host strain is a member of the genus *Escherichia*. The host strain may be *Escherichia coli*. The *Escherichia coli* host strain used to produce the polypeptide of interest is preferably derived from a K-12 strain, such as *E. coli* K-12 substrain MG1655 (ATCC® 47076™).

Inclusion Body Isolation

Because of the insolubility of the inclusion body, a convenient method for isolating it would start with lysing the cells, with or without mechanical disruption. These methods generally involve suspending cells in an isotonic or hypotonic solution containing a non-denaturing surfactant (e.g., octylglucoside, TRITON® x-100, NP-40 and the like) and, optionally, disrupting the cells, such as by (ultra)sonication, pressure cycling or other homogenization method. In some methods, the suspended bacteria are treated with commercially available enzymes that lyse the cell wall, e.g., lysozyme. The relevant end point is that the contents of the bacterial cytoplasm, i.e., the polypeptide of interest, preferably in the form of inclusion bodies, are released into the lysing media.

Once lysed or disrupted, the cell lysate is usually subjected to one or more kinds of centrifugation in order to obtain a preparation of the inclusion bodies. For example, the density of the medium may be increased to an empirically determined value that is suitable for allowing the inclusion bodies to form a pellet after centrifugation. The increase in density range of the gradient may be achieved by adding sucrose, glycerol, FICOLL™ and the like, to the desired concentration. The relative buoyant density of the inclusion bodies may be determined by density gradient centrifugation, as illustrated herein.

Cleavable Peptide Linkers

The use of cleavable peptide linkers is well known in the art. Fusion peptides comprising at least one inclusion body tag will typically include at least one cleavable sequence separating the inclusion body tag from the peptide of interest. The cleavable sequence facilitates separation of the inclusion body tag(s) from the peptide(s) of interest. The cleavable sequence may be provided by a portion of the inclusion body tag and/or the peptide of interest (e.g., inclusion of an acid cleavable aspartic acid-proline moiety). The cleavable sequence preferably includes in the fusion peptide at least one cleavable peptide linker between the inclusion body tag and the peptide of interest.

Means to cleave the peptide linkers are well known in the art and may include chemical hydrolysis, enzymatic cleavage agents, and combinations thereof. One or more chemically cleavable peptide linkers are included in the fusion construct to facilitate recovery of the peptide of interest from the inclusion body fusion protein. Examples of chemical cleavage reagents include cyanogen bromide, which cleaves methionine residues; N-chloro succinimide, iodobenzoic acid or BNPS-skatole [2-(2-nitrophenylsulfenyl)-3-methylindole], which cleaves tryptophan residues; dilute acids, which cleave at aspartyl-prolyl bonds, one or more aspartic acid-proline acid cleavable recognition sites (i.e., a cleavable peptide linker comprising one or more D-P dipeptide moieties) may preferably be included in the fusion protein construct to facilitate separation of the inclusion body tag(s) form the peptide of interest. The fusion peptide may include multiple regions encoding peptides of interest separated by one or more cleavable peptide linkers.

Moreover, one or more enzymatic cleavage sequences may be included in the fusion protein construct to facilitate recovery of the peptide of interest. Proteolytic enzymes and their respective cleavage site specificities are well known in the art.

Preferably, the proteolytic enzyme is selected to specifically cleave only the peptide linker separating the inclusion body tag and the peptide of interest. Examples of enzymes useful for cleaving the peptide linker include, but are not limited to, Arg-C proteinase, Asp-N endopeptidase, chymotrypsin, clostripain, enterokinase, Factor Xa, glutamyl endopeptidase, Granzyme B, Achromobacter proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Talanian et al., *J. Biol. Chem.* (1997) 272(15): 9677-9682).

Typically, cleavage occurs after the insoluble inclusion bodies and/or insoluble fusion peptides are isolated from the cell lysate. Methods of lysing cells and isolation peptide from the cell lysate are well known in the art. Once isolated, the insoluble inclusion bodies and/or fusion peptides can be treated with a chemical cleavage agent or enzymatic cleavage agent to cleave the inclusion body tag from the peptide of interest. After cleavage step, preferably, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. The peptide of interest may be soluble or insoluble while the inclusion body tag and/or fusion protein is insoluble or soluble in the defined process matrix, typically aqueous. Optionally, the peptide of interest may be further purified using any number of well known purification techniques in the art such as ion exchange, gel purification techniques, and column chromatography (see U.S. Pat. No. 5,648,244).

Fermentation Media

Fermentation media must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. L-arabinose is used to induce the present arabinose inducible expression system. As such, L-arabinose is typically not included in the fermentation media until expression of the desired chimeric gene (encoding the peptide or protein of interest) is desired. L-arabinose can be added at any time during the fermentation, although it is often preferable to induce expression only after a desired cell density/mass is achieved in the fermentor. It is contemplated that the source of carbon utilized in the present invention may encompass a wide variety of carbon containing substrates and will only be limited by the choice of organism. Preferred carbon substrates include glucose, fructose, and sucrose.

In addition to a carbon source, fermentation media may or must contain other components suitable and/or necessary for the growth of the cultures and promotion of the expression of the present fusion peptides. These are known to those skilled in the art and include minerals, salts, cofactors, buffers, etc.

Culture Conditions

Suitable growth conditions can vary and depend on the chosen production host and are generally known in the art. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred. Fermentation may be performed under either aerobic or anaerobic conditions whereas aerobic conditions are generally preferred.

Industrial Batch and Continuous Fermentations

Classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, (1992) 36:227-234.

Although typically performed in batch mode, it is contemplated that the methods described herein would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The methods described herein may be practiced using either batch, fed-batch or continuous processes and that any known mode of fermentation would be suitable.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), "ng" means nanogram(s), "g" means gravity, "gf" means maximum grams force, "HPLC" means high performance liquid chromatography, "dd H$_2$O" means distilled and deionized water, "dcw" means dry cell weight, "ATCC" or "ATCC®" means the American Type Culture Collection (Manassas, Va.), "rpm" means revolution(s) per minute, and "EDTA" means ethylenediaminetetraacetic acid.

Compositions of Growth Media and Buffers

TABLE 1

Media and Buffers

| Media/Buffer | Ingredient | Amount |
|---|---|---|
| Miller LB | Casein protein | 10 g/L |
| | NaCl | 10 g/L |
| | Yeast extract | 5 g/L |
| Dubelco's 1X PBS | KCl | 0.2 g/L |
| | KH$_2$PO$_4$ | 0.2 g/L |
| | NaCl | 8 g/L |
| | Na$_2$HPO$_4$•7H$_2$O | 2.16 g/L |
| DEK Media | KH$_2$PO$_4$ | 9 g/L |
| | (NH$_4$)$_2$HPO$_4$ | 4 g/L |
| | Citric acid•H$_2$O | 1.86 g/L |
| | Yeast extract | 5 g/L |
| | Biospumex 153K (Post sterilization) | 0.1 mL/L |
| | MgSO$_4$•7H$_2$O | 1.2 g/L |
| | Thiamine HCl | 4.5 mg/L |
| | Trace elements (batch - see below) | 10 mL/L |
| | Uracil | 50 mg/L |
| Trace elements | EDTA | 840 mg/L |
| | CoCl$_2$•6H$_2$O | 250 mg/L |

TABLE 1-continued

Media and Buffers

| Media/Buffer | Ingredient | Amount |
|---|---|---|
| | MnCl$_2$•4H$_2$O | 1500 mg/L |
| | CuCl$_2$•2H$_2$O | 150 mg/L |
| | H$_3$BO$_3$ | 300 mg/L |
| | Na$_2$MoO$_4$•2H$_2$O | 250 mg/L |
| | Zn(CH$_3$COO)$_2$•2H$_2$O | 1300 mg/L |
| | Fe(III) Citrate | 10000 mg/L |

EXAMPLE 1

Density Gradient Separation of Uninduced *E. coli* Cells from Induced *E. coli* Cells Expressing the POI as Inclusion Bodies This example describes a method for separating *E. coli* cells producing a peptide of interest (POI) that accumulates as inclusion bodies from those cells lacking inclusion bodies. The method of separating these populations of cells is based on their differences in buoyant density. PERCOLL™ (Sigma-Aldrich) was chosen as the density gradient medium because of its non-toxic nature, low viscosity at high concentrations, and its self-forming gradient properties.

In order to reach high production yield and reduce separation costs, peptides of interest were produced to accumulate in the form of insoluble inclusion bodies (i.e., "IB") in *E. coli* production hosts. Inclusion body promoting sequences referred to as inclusion body tags ("IBT") were usually fused to the N-terminus of the POI to direct peptide accumulation into inclusion bodies. An acid cleavable site consisting of an aspartic acid-proline pair (i.e., DP) was introduced between the inclusion body promoting sequence and the POI in order to facilitate the release of the POI from the IB. Following are the strains used in this study; 1) QC1100: KK2000 ΔslyD, 2) QC1525: KK2000 ΔslyD containing plasmid pDCQ523 (SEQ ID NO:144), which expresses the genetic construct encoding IBT139(5C)-CCPGCC-HC415 (SEQ ID NO:146) peptide (~28 kDa) under araBAD promoter (SEQ ID NO:148), 3) QC1101: KK2000 ΔslyD containing plasmid pLR199 (SEQ ID NO:141), which expresses IBT139-CCPGCC-HC124 peptide (SEQ ID NO: 143) (~28 kDa) under araBAD promoter (SEQ ID NO: 148). KK2000 is a derivative of *E. coli* MG1655 (ATCC® 47076) that contained the deletion of the endogenous araBAD genes. IBT139(5C) is in an inclusion body tag derived from IBT139 where an effective number of cross-linkable cysteine residues (5 resides) was inserted into inclusion body tag IBT139 (see co-owned U.S. Patent Application Publication 2009-0043075A to Alsop et al.; hereby incorporated by reference in its entirety).

QC1525 cells were grown overnight in LB medium containing ampicillin (100 µg/mL). QC1525 cells from fresh overnight cultures were grown until they reached an optical density (OD$_{600}$) of approximately 0.5-0.7, and were then inoculated into four flasks, one flask of cells that were grown but not induced and another 3 flasks of cells that were induced with 0.02% L-arabinose (Sigma-Aldrich). Induced cells were incubated for 3.5 h, 21.5 h or 24 h at 37° C. with 250 rpm shaking speed. Following induction and incubation as described, the OD$_{600}$ of all four flasks of cells were measured and cells corresponding to 9 OD$_{600}$ (45×10$^8$ cells total) were added to a mix of 30 mL comprising of 21 mL (70%) PERCOLL™ (a density gradient-forming composition comprising non colloidal silica (15-30 nm diameter coated with a non-dialyzable polyvinylpyrrolidone coating), and LB medium was added to a final volume of 30 mL and mixed well. One mL of each mix was centrifuged in 2-mL centrifuge tubes in a table top centrifuge (Eppendorf, model 5417R) at 14000 rpm for 90 minutes. The distribution of the cells in the 2-mL centrifuge tubes was then photographed.

Figure 3:
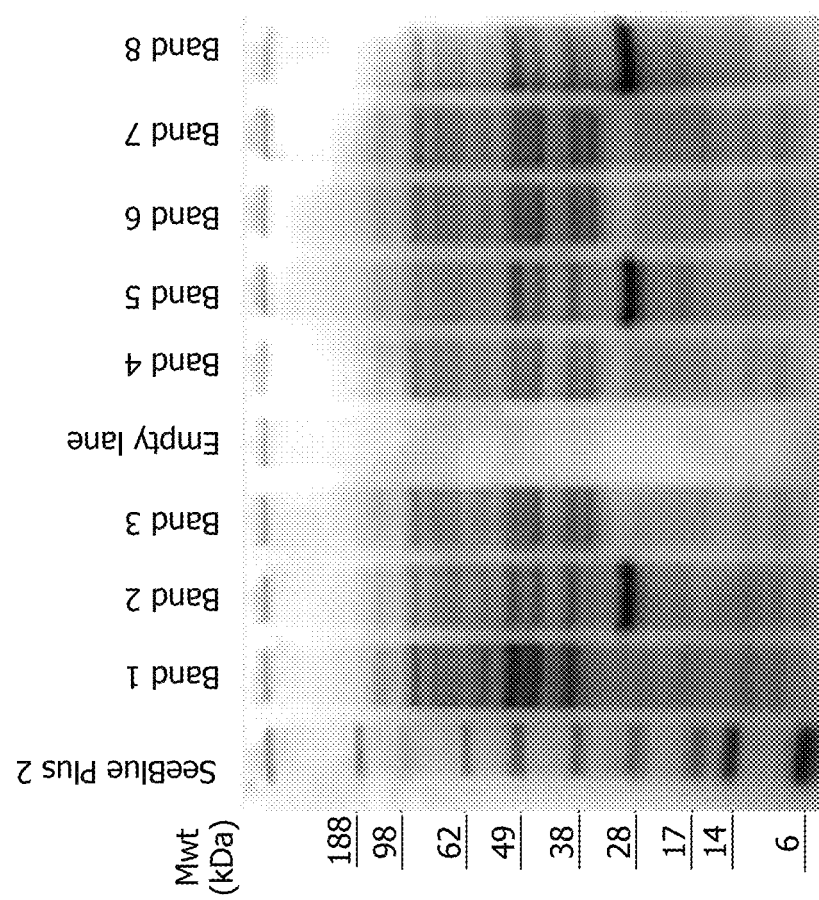
FIG. 3. Image of SDS-PAGE of the bands extracted from density gradient as shown by numbered arrows pointing to different bands in FIGS. 2a, 2b, 2c, and 2d. The lowermost band corresponding to higher buoyant density from each tube produced the ~28 kDa peptide of interest.

The uninduced cells showed a single band (FIG. 1a), while cells induced for 3.5 h, 21.5 h or 24 h showed 2 major bands including a band lower than that observed in the uninduced cells (FIGS. 1b, 1c, and 1d, respectively). The remaining 29 mL of each mixed sample was centrifuged in a polycarbonate tube at 15000 rpm in a SS-34 rotor (~27000×g) at 20° C. for one hour in a Sorvall RC-5B centrifuge. Polycarbonate tubes with the density gradient profile of uninduced and induced cells (3.5 h, 21.5 h or 24 h) were photographed (FIGS. 2a, 2b, 2c, and 2d). Different density gradient profiles were observed for uninduced and induced cells. The uninduced cells (FIG. 2a) had a major band of cells more towards the meniscus at the top of the gradient while cells induced for 3.5 h (FIG. 2b) had one faint upper band and one major band (arrow 2) significantly lower than the band observed in the uninduced cells. Cells induced for 21.5 h (FIG. 2c) or 24 h (FIG. 2d) showed multiple bands all lower than the band seen in uninduced cells (FIG. 2a). The bands as indicated in FIGS. 2a, 2b, 2c, and 2d were extracted by inserting a sterile syringe from the top of the centrifuge tubes. To prevent contamination of cells from one layer to another, a new syringe was used for every layer. The extracted cells were washed with 1×PBS, cells were pelleted down at 6500 rpm for 15 minutes, resuspended in 1 mL of 1×PBS, and then the $OD_{600}$ was measured. Cell samples were normalized to 0.4 OD, to which was added 15 µL of deionized water and 15 µL of 2×SDS loading dye. The cells within the resultant mix of each sample were lysed by heating to 100° C. for 15 min in a heated dry block and centrifuged briefly. The samples were run on a NUPAGE® 4-12% Bis-Tris gel with the SEEBLUE® Plus2 pre-stained standard (Invitrogen). At the end of the run the gel was rinsed with water, stained with SIMPLYBLUE™ (Invitrogen) and destained with deionized water. A band corresponding to a ~28 kDa protein was observed in cells extracted from lower band of the induced cells (FIG. 3, bands 2, 5, and 8). The ~28 kDa band was absent in uninduced cells and the upper layers from induced cells (FIG. 3, bands 1, 3, 4, 6, and 7). Therefore, this density gradient centrifugation method can be utilized for the separation of uninduced cells from induced cells expressing a polypeptide of interest (POI).

EXAMPLE 2

Density Gradient Separation of Induced E. coli Cells Producing Different Inclusion Bodies This example illustrates that cells producing different inclusion bodies can have sufficiently distinct buoyant densities to permit separation on density gradients.

The density gradient band profile of QC1101 cells (Strain QC1101: KK2000 ΔslyD containing plasmid pLR199 (SEQ ID NO: 141), which expresses IBT139-CCPGCC-HC124 (SEQ ID NO: 143) under control of an araBAD promoter (SEQ ID NO:148) were compared with the QC1525 cells described above, which express IBT139(5C)-CCPGCC-HC415 (SEQ ID NO: 146) peptide. Both E. coli strains were grown overnight in LB medium containing ampicillin (100 µg/mL). The following morning, QC1101 and QC1525 cells were respectively sub-cultured into LB flasks containing carbenicillin (100 µg/mL). One batch each of QC1101 and QC1525 cells was induced with 0.02% L-arabinose (Sigma-Aldrich) at $OD_{600}$~0.5-0.7, while a batch of QC1101 cells was not induced (control). All three flasks of cells were grown for 22 hours following the time of induction and the $OD_{600}$ was monitored.

As previously described a total of 9 $OD_{600}$ (approximately 45×10$^8$ cells total) cells of each of the above described samples were individually added to their respective tubes containing 21 mL (70%) PERCOLL™ in 0.9% NaCl followed by LB media to a total volume of 30 mL. In addition to QC1101 uninduced (QC1101 U), QC1101 induced (QC1101 I), and QC1525 (QC1525 I) induced samples, another sample was prepared by mixing QC1101 induced cells and QC1525 induced cells (QC1101 I+QC1525 I) and added to a tube containing 21 mL (70%) PERCOLL™, 0.9% NaCl in a total volume of 30 mL. All samples were mixed well and transferred to polycarbonate centrifuge tubes and centrifuged as described above. The tubes after centrifugation were digitally photographed and bands corresponding to the cells were compared (FIGS. 4a, 4b, 4c, and 4d).

Figures 4A, 4B, 4C, 4D:
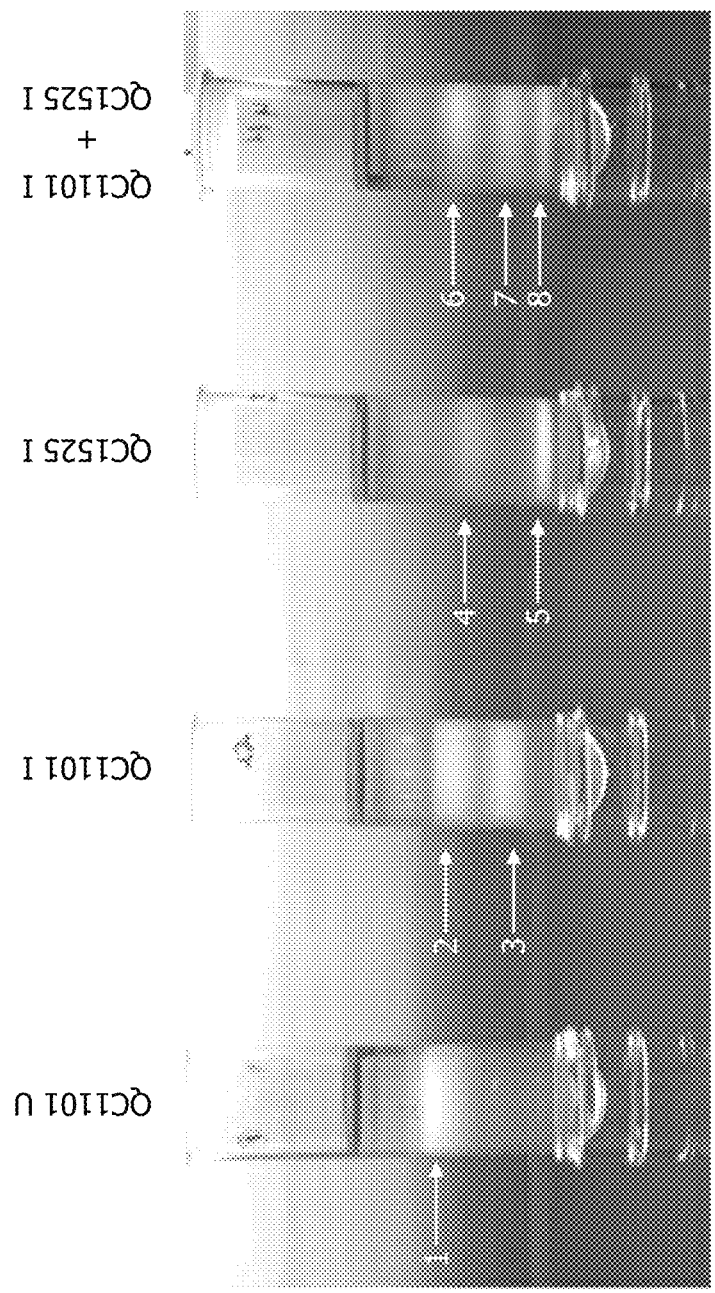
FIGS. 4(a-d). Images of centrifuge tubes showing separation of uninduced cells (FIG. 4a; arrow to band 1), and induced cells producing different fusion peptides. Induced QC1101 I (FIG. 4b; arrows to bands 2 and 3), induced QC1525 I (FIG. 4c; arrows 4 and 5), and a mixture of induce cells QC1101 I+DC1525 I (FIG. 4d; arrows 6, 7, and 8).

QC1101 uninduced cells showed a major band towards the top of the gradient (FIG. 4a; arrow 1) while QC1101 induced cells showed 2 prominent bands, upper and lower (FIG. 4b; arrows 2 and 3). QC1525 induced cells also showed 2 bands, an upper band (arrow 4) that is much fainter than the QC1101 induced sample and a lower band (arrow 5) that is lower than lower band seen in QC1101 induced cells (FIG. 4c). The sample which had both QC1101 induced and QC1525 induced cells mixed together had an intermediate profile matching QC1101 induced and QC1525 induced cells (FIG. 4d). The three bands (FIG. 4d; arrows 6, 7, and 8) characteristic of QC1101 and QC1525 induced cells were all clearly distinguishable indicating that the separation of the three bands was based on the respective buoyant densities of the cell samples.

Bands as indicated in FIGS. 4a, 4b, 4c, and 4d were extracted by inserting a sterile syringe from top and processed as described earlier in Example 1. A band corresponding to the ~28 kDa POI was observed in cells extracted from lower band of the QC1101 induced cells, while no bands were seen in upper band of QC1101 induced or QC1101 uninduced cells. A band corresponding to the ~28 kDa POI was seen in cells extracted from the lower band of induced QC1525 cells, while no protein specific band was visualized from upper band of QC1525 induced cells. QC1525 induced cells had higher buoyant density compared to QC1101 induced cells and could be separated on density gradient as seen in density gradient pattern of the mixed sample containing both QC1101 induced and QC1525 induced cells (FIG. 4d). This was confirmed by the SDS-PAGE pattern of the same. In order to quantify the difference in buoyant density, the experiment was repeated with custom synthesized density marker beads (American density Material Inc., VA, USA) for approximating the densities of specific points of buoyant density that correspond to those of QC1101 and QC1525.

The buoyant density of QC1101 uninduced cells was ~1.082 g/mL, while the upper band of QC1101 induced cells had buoyant density of ~1.103 g/mL and lower band had a buoyant density of ~1.118 g/mL. QC1525 induced cells had buoyant density of ~1.126 g/mL for the major lower band. One milliliter of each of the above 4 samples, (i.e., QC1101 uninduced, QC1101 induced, QC1525 induced, and mixed samples of QC1101 induced and QC1525 induced) were mixed with 70% PERCOLL™, LB media, and 0.9% NaCl and centrifuged in microcentrifuge tubes as described in Example 1. It was demonstrated that cells with different inclusion bodies (i.e., induced QC1101 cells) could be distinguished from induced QC1525 cells, thus allowing the method to be applied for larger scale density gradient screening.

EXAMPLE 3

Generation of BL21 Genomic DNA Library to Identify Genes that May Increase Buoyant Density of E. coli Cells Producing HC124

To identify genes that can increase the buoyant density of E. coli cells, genomic DNA library from E. coli BL21 strain was constructed. Genomic DNA fragments of approximately 2 to 3 kb in size were obtained from E. coli BL21 strain by partial digestion of the BL21 genomic DNA with Tas I restriction enzyme at a non-ideal temperature (to prevent complete digestion) of 55° C. for 50 minutes. The digested fragments were subjected to agarose gel electrophoresis alongside a DNA molecular weight ladder. Agarose slices containing genomic DNA fragments corresponding in size to approximately 2 to 3 kb were excised from gel and the DNA therein eluted.

Vector pDCQ601 (SEQ ID NO: 159) was digested with 5 units of EcoRI (NEB, USA) at 37° overnight. The 5.3 kb fragment corresponding to EcoRI digested plasmid was eluted from an agarose gel. The eluted EcoRI digested plasmid was treated with Antarctic phophatase (New Engand Biolabs, USA) for 1 hour at 37° C., followed by heat inactivation of the Antarctic phophatase by incubating the reaction mix at 65° C. for 5 minutes. The reaction mix was cleaned by using DNA Cleanup Kit (Zymo Research, USA). Aliquots of the eluates of both EcoRI digested and phosphatase treated vector and the Tas I digested genomic DNA (2-3 Kb fragments) were combined for ligation using Roche Rapid DNA Ligation Kit (Roche, USA). The ligation reaction used vector ends and insert ends ratio of 1:3 at 24° C. for 15 min in a total volume of 21 µL.

An aliquot of 10 µL of the ligation mix was used to transform CB5 alpha competent cells (Chromous Biotech, Bangalore, India; Catalog #PCR 16-NP) which were then plated on 4 different LB Kan plates. An average of 2000 colonies per plate was obtained. Additional ligations were done in four batches and four plasmid pools of approximately 15000 colonies each were prepared and transformed into QC1101 electrocompetent cells to have ~10-fold coverage of the E. coli BL21 genome. Thirty colonies from transformed QC1101 cells were randomly picked and tested for ~2-3 Kb inserts by colony PCR using PBHR1F (SEQ ID NO: 162) and PBHR1R (SEQ ID NO: 163) primers in the following manner. Random colonies were picked from $LB^{Amp+Kan+}$ plates and were lysed by heating at 95° C. for 5 min. Standard PCR was performed with annealing temperature of 55° C. for 30 sec and extension temperature of 72° C. for 3.5 min. All colonies were found to have ~2-3 kb inserts. Sequencing of greater than 30 plasmids isolated from these colonies revealed that all of them had unique DNA inserts. The BL21 genomic DNA library with 2-3 kb insert size (designated as RK1) was used to screen for genes that can increase the buoyant density of E. coli cells that are synthesizing polypeptides that accumulate in the form of inclusion bodies.

EXAMPLE 4

Density Gradient Sorting of Inclusion Bodies is Influenced by Genes Obtained from a BL21 Genomic DNA Library and Introduced into Inclusion Body-Expressing E. coli Cells To screen and identify genes that can increase the buoyant density of E. coli that contain inclusion bodies, QC1101 cells that harbor plasmid pLR199 (SEQ ID NO: 141), which expresses the genetic construct encoding IBT139-CCPGCC-HC124 (SEQ ID NO: 142) under the araBAD (SEQ ID NO: 148) promoter and transformed with pDCQ601 plasmid library pools of 2-3 Kb BL21 genomic DNA fragments (RK1 library) were grown overnight in LB medium containing 100 µg/mL ampicillin, 50 µg/mL kanamycin. The following morning, the RK1-transformed cells were freshly inoculated into 2 flasks of LB medium containing 100 µg/mL carbenicillin, 50 µg/mL kanamycin and grown to an $OD_{600}$ of ~0.6. One flask of cells was induced with 0.02% L-arabinose while the other flask was used as an uninduced control. Cells were grown for 5 hours following induction and $OD_{600}$ of both the flasks of cells was measured. Cells corresponding to 9 $OD_{600}$ (45×10$^8$ cells total) were added to a mix of 30 mL volume comprising of 21 mL (70%) PERCOLL™, 0.9% NaCl and rest of the volume was made up with LB medium. A density marker sample with varying density marker beads (American Density Materials Inc.) was prepared similarly. All the samples were mixed well and spun at 15000 rpm (approximately 27000×g) in a SS-34 rotor at 20° C. for one hour in Sorvall centrifuge in polycarbonate tubes. Following centrifugation the tubes were digitally photographed.

In comparison with control (i.e., uninduced cells) which had a single band upwards towards the meniscus with buoyant density of ~1.094, induced cells had 2 bands, an upper band with buoyant density of ~1.106 and a lower band which was significantly lower than the band seen in uninduced cells with a buoyant density of ~1.120. All bands were aspirated out with sterile 10-mL syringes and washed with 1×PBS by centrifuging at 6500 rpm at 4° C. for 15 min and $OD_{600}$ was taken. $OD_{600}$ of the extracted cells was normalized. Cell lysates from the uninduced and induced samples were electrophoresed on 4-12% bis-tris gel as described in Example 1.

Figure 5:
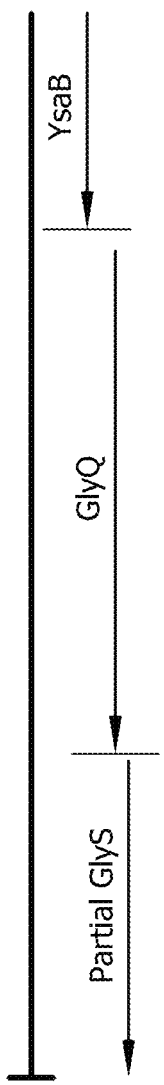
FIG. 5. Genetic arrangement of the approximate 2 kb region in *E. coli* BL21 genome that was identified in colony 181 which showed increased buoyant density from sorting of plasmid expression library. This region contains the full length ysaB and glyQ genes and a polynucleotide sequence encoding the N terminal portion of the glyS gene.

The lower band corresponded to cells having intracellular inclusion body was confirmed by SDS-PAGE. Cells extracted from the lower band of RK1 induced cells from the density gradient were used as the inoculum for the next round of growth and sorting. Four more sorting cycles for a total of 5 rounds of sorting were performed. Cells from each sorting cycle were plated onto $LB^{Amp+Kan+}$ plate and 20 random colonies were picked for DNA sequencing and for micro density gradient centrifugation. One of the colonies in the fifth sort, colony 181, demonstrated increased buoyant density in the micro density gradient. The sequence of the insert (SEQ ID NO: 152) identified the region to be an approximately 2 Kb genomic DNA insert containing ysaB, glyQ, and partial glyS genes (FIG. 5). The vector housing the BL21 library, pDCQ601, did not provide a heterologous promoter in an orientation that would account for the expression of the insert containing ysaB, glyQ, and partial glyS genes. Accordingly, it is believed that the insert contains one or more endogenous promoters in addition to the nucleotide sequences encoding the YsaB (a conserved hypothetical protein), GlyQ (glycyl-tRNA synthetase; subunit alpha) and partial GlyS (glycyl-tRNA synthetase; beta subunit) polypeptides.

Figure 6:
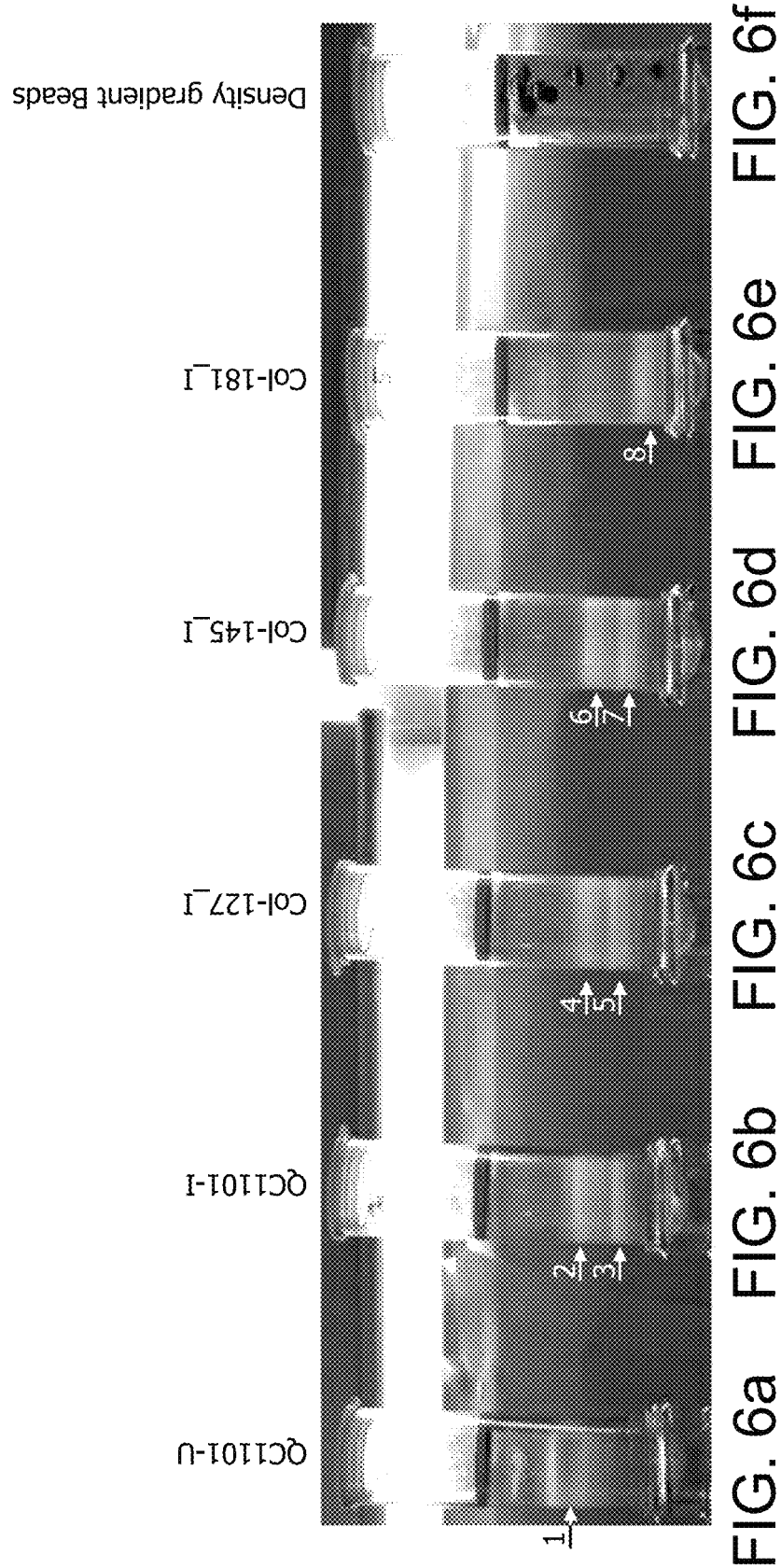
FIGS. 6(a-f). Images of centrifuge tubes showing confirmation of isolate of interest by density gradient centrifugation. Uninduced cells QC1101-U (FIG. 6a; arrow to band 1), induced QC1101-I (FIG. 6b; arrows to bands 2 and 3), induced Col-127_I (FIG. 6c, arrows to bands 4 and 5), induced Col-145_I (FIG. 6d, arrows to bands 6 and 7), induced Col-181__1 (FIG. 6e, arrow to band 8), and a tube containing density gradient beads (FIG. 6f). Note the increased buoyant density in induced colony 181 (FIG. 6e; band 8) in comparison to QC1101-I lower band (FIG. 6b; band 3).
Figure 7:
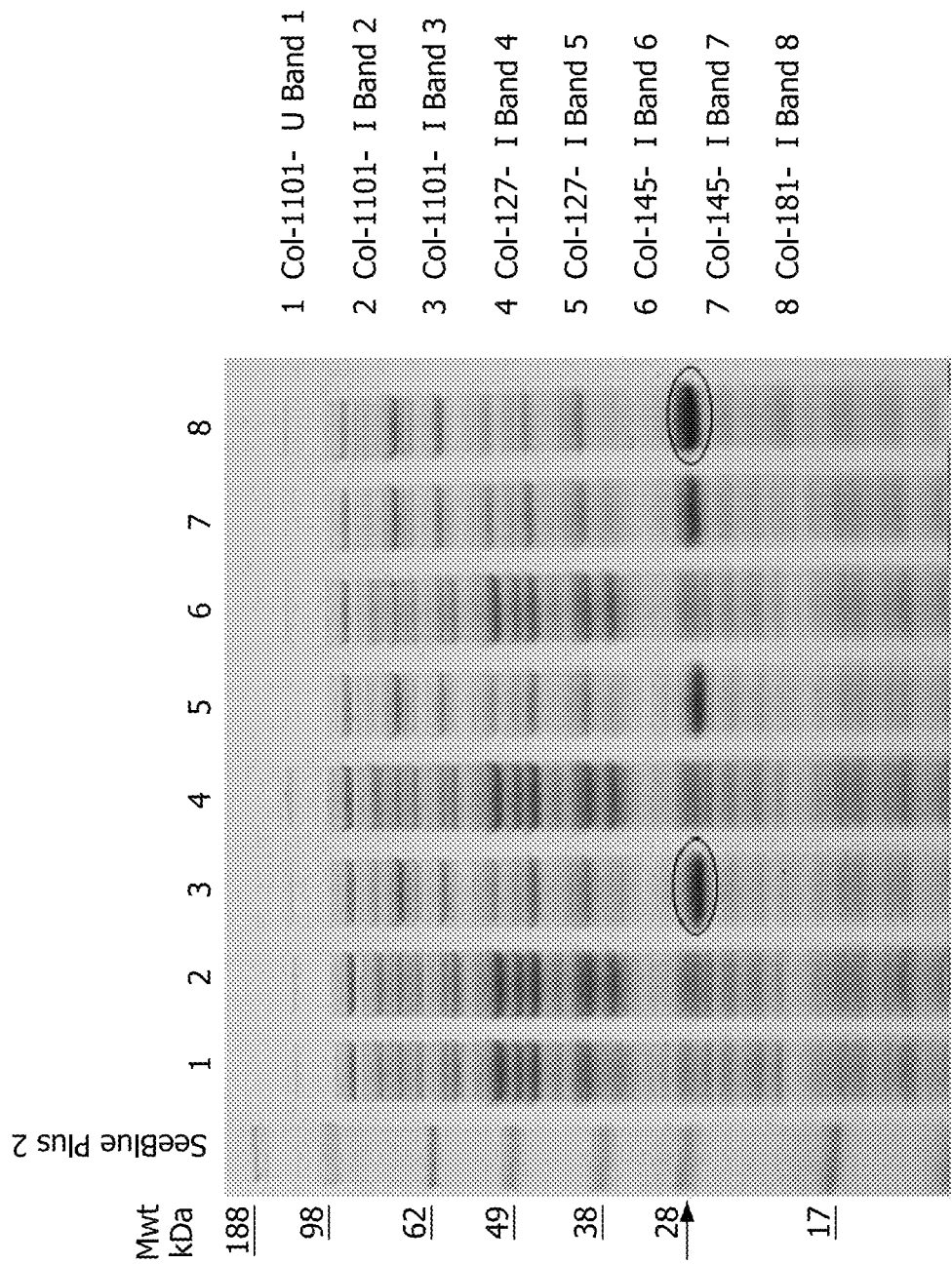
FIG. 7. Image of SDS-PAGE of the cell lysate extracted from the bands shown in the PERCOLL™ density gradient of FIGS. 6a, 6b, 6c, 6d, and 6e. The number at the top of each lane corresponds to the numbered bands in the PERCOLL™ gradients shown in FIGS. 6a through 6e. Lane 3 (from band 3.

A density gradient was set up with control strain QC1101, two other candidates from sort 3 (colony 127 and colony 145) and colony 181 (sort 5) were grown and induced along with uninduced QC1101 cells as control as described earlier in the Example 3. All samples, i.e., QC1101 uninduced cells (FIG. 6a; QC1101-U), QC1101 induced cells (FIG. 6b; QC1101-I), colony 127 induced cells (FIG. 6c; Col-127_1), colony 145 induced cells (FIG. 6d; Coli-145_I), and colony 181 induced cells (FIG. 6e; Col-181_1) were subjected to a density gradient separation as described earlier. Density gradient beads were also subjected to a density gradient (FIG. 6f). QC1101 induced cells had two bands of cells with buoyant density of ~1.098 g/mL and ~1.118 g/mL) (FIG. 6b; arrows 2 and 3), while colony 181 induced cells had a single band with buoyant density of ~1.125 g/mL) (FIG. 6e; arrow 8) confirming the increase in the buoyant density of E. coli cells with the DNA insert comprising ysaB, glyQ, and partial glyS genes. Cells from each of the cultures of QC1101 uninduced cells, QC1101 induced cells, colony 127 induced cells, colony 145 induced cells, and colony 181 induced cells were normalized by $OD_{600}$ and following lysis and electrophoresis were examined for band intensity corresponding to ~28 kDa band of interest by densitometry in Bio-Rad densitometer. An increase of ~34% in ~28 kDa POI was noted in colony 181 induced cells in comparison to induced QC1101 cells (FIG. 7, lane 3 and lane 8).

It was then determined whether or not this increased buoyant density was a result of having the DNA insert (comprising ysaB, glyQ, and partial glyS gene (SEQ ID NO: 152)). Vector pDCQ601 (SEQ ID NO: 159) carrying a ~2 Kb DNA insert (ysaB, glyQ, partial glyS gene as explained above) and pLR199 (SEQ ID NO: 141) were extracted from colony 181 induced cells by standard plasmid extraction methods. The vector and plasmid were transformed into new QC1100 host cells that lack both of the above described plasmids. The transformed QC1100 strain, along with QC1101 induced and uninduced controls were checked for changes in buoyant density and peptide expression. QC1101 was grown and induced exactly as described earlier as a control. Uninduced and induced QC1101 cells along with transformed QC1100 induced cells were subjected to a density gradient. The increase in buoyant density was evident in transformed QC1100 cells in comparison to induced QC1101 and uninduced QC1101. SDS-PAGE of cell lysates from these samples revealed an increase of ~34% in ~28 kDa POI in QC1100 transformed with the plasmids validating that the BL21 genomic region comprising ysaB, glyQ and partial glyS (SEQ ID NO: 152) was responsible for conferring the phenotype of heavier buoyant density to E. coli cells.

EXAMPLE 5

Density Gradient Sorting of a Knock-Out Library to Identify Genes Altering the Buoyant Density of Inclusion Body-Expressing E. coli Cells To screen for gene knockouts that may increase buoyant density of inclusion body producing cells, a gene knockout library was made by pooling the individual gene deletions of E. coli in the Keio collection (Baba, T., et al., supra). The Keio collection is essentially a library of non-lethal in-frame single gene knockouts.

The plasmid which expresses the genetic construct encoding IBT139(5C)-CCPGCC-HC415 (SEQ ID NO: 145) under araBAD promoter (SEQ ID NO: 148) was transformed into the pooled Keio deletion strains. The transformed cells were plated on LB plates with carbenicillin 100 μg/mL. All the colonies grown on carbenicillin selection plates were scraped off and resuspended in DEK medium with carbenicillin 100 μg/mL. This suspension was diluted to an $OD_{600}$ ~4 and used to inoculate 10 mL of fresh DEK medium with carbenicillin 100 μg/mL. The cultures were grown at 37° C. with shaking for 2 hours until an $OD_{600}$ ~1.5 was reached. The cells were induced with 0.2% L-arabinose for 3 hours. Six milliliters of the induced cultures were diluted with 3 mL of fresh DEK medium and mixed with 21 mL of PERCOLL™ to make the final volume of 30 mL. The mixture was centrifuged at 27,000×g for 1 hour at 18° C. The cells from the bottom one-third of the band on density gradient were recovered using a 1-mL pipette. The cells were washed twice with 35 mL of phosphate buffered saline (PBS) and resuspended in fresh DEK medium with 100 μg/mL carbenicillin and were used as the seed culture for the next round of enrichment. A total of three rounds of enrichment of denser inclusion body-producing cells were performed. At the end of the third round, the recovered cells were diluted and plated on LB medium with 100 μg/mL carbenicillin plates. Colonies were randomly picked for sequencing to identify the gene mutation. Eight clones with multiple hits were selected to be tested by density gradient centrifugation. The eight individual isolates (F1, B3, C6, F1, A12, B11, D2, and E4) were grown in LB medium with carbenicillin (100 μg/mL) and kanamycin (25 μg/mL) together with the control; wild type strain BW25113 (FIG. 8; "BW") containing the same inclusion body producing plasmid) in LB medium with carbenicillin (100 μg/mL) till $OD_{600}$ ~0.6 and induced with 0.2% L-arabinose for approximately 17 hours. Normalized concentrations of whole cells were loaded in 70% PERCOLL™ in microfuge tubes.

Figure 8:
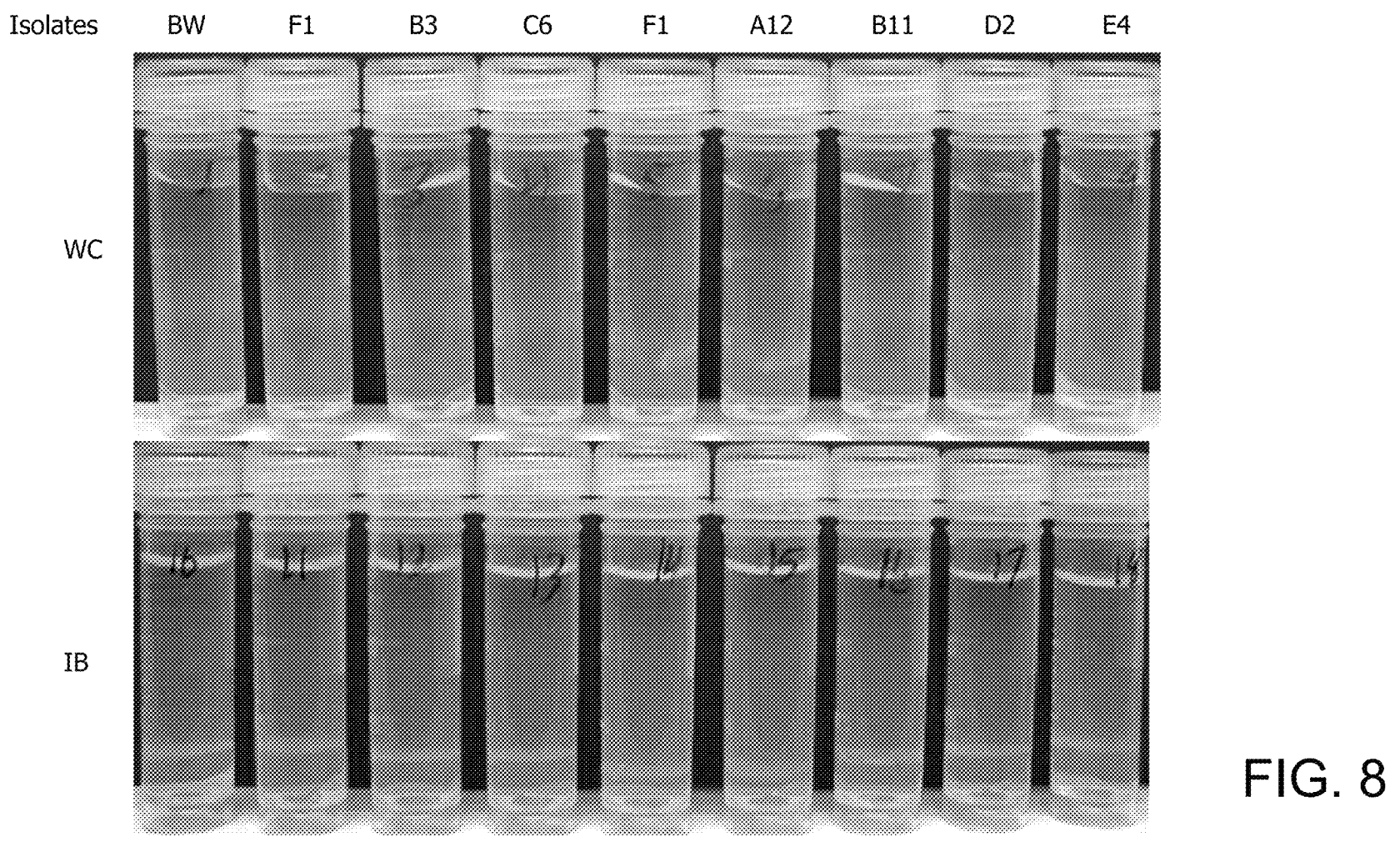

In addition, whole cells were frozen at −80° C. and subsequently lysed using Celytic Express (Sigma-Aldrich, St Louis, Mo.) for 1 hour at 37° C. The crude inclusion body preparations obtained from the lysed cells were also loaded in 70% PERCOLL™ in microfuge tubes. The microfuge density gradient samples were centrifuged at 15,000×g for 90 min. After centrifugation, the samples were taken out and photographed as shown in FIG. 8. The top panel (WC) shows the whole cell samples which had wider density gradient bands than were previously observed. The lower panel (IB) shows the banding of the crude inclusion body samples obtained from the corresponding whole cell samples shown directly above (panel WC). The IB bands clearly demonstrate more discrete density gradient bands than the whole cells in FIG. 8. As shown for both the cell bands and the IB bands, isolates F1 and A12 showed increased density when compared to the respective controls (FIG. 8, BW).

The two positive hits were repeated as described above. Additional IB samples were prepared from 3.5 mL of induced cultures by freeze-thawing and lysing with Celytic for 1 hour at 37° C. The crude IB preparation was loaded onto 70% PERCOLL™ in the 30-mL large centrifuge tubes and centrifuged at 27,000×g for 60 min. Both isolates exhibited denser inclusion bodies than the control. Sequencing of the two isolates showed that they contained the gltA deletion (ΔgltA). GRA is encoded by the polynucleotide SEQ ID NO: 164 encoding citrate synthase (SEQ ID NO: 165).

Figures 9A, 9B, 9C:
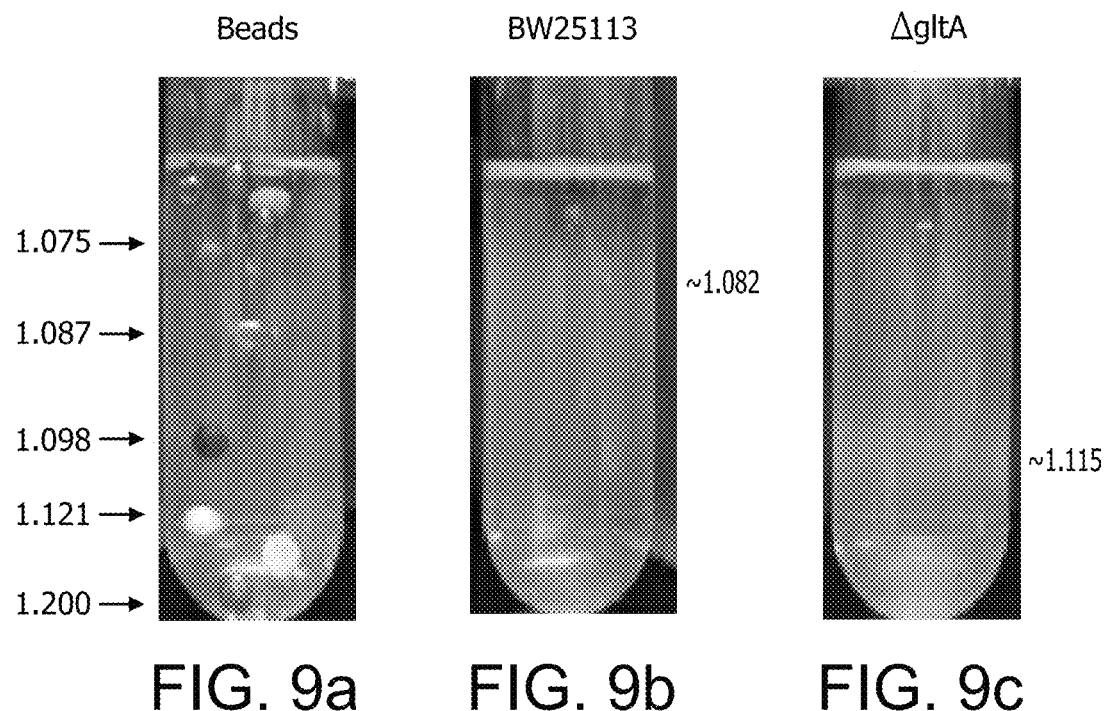
FIGS. 9a and 9d are images of density gradient separated beads of various buoyant densities.
FIG. 9b shows a band (approximately 1.082 g/mL) formed after density gradient centrifugation of whole cells of control strain BW25113.
FIG. 9c shows a band (approximately 1.115 g/mL) formed after density gradient separation of whole cells from a ΔgltA strain.
Figures 9D, 9E, 9F:
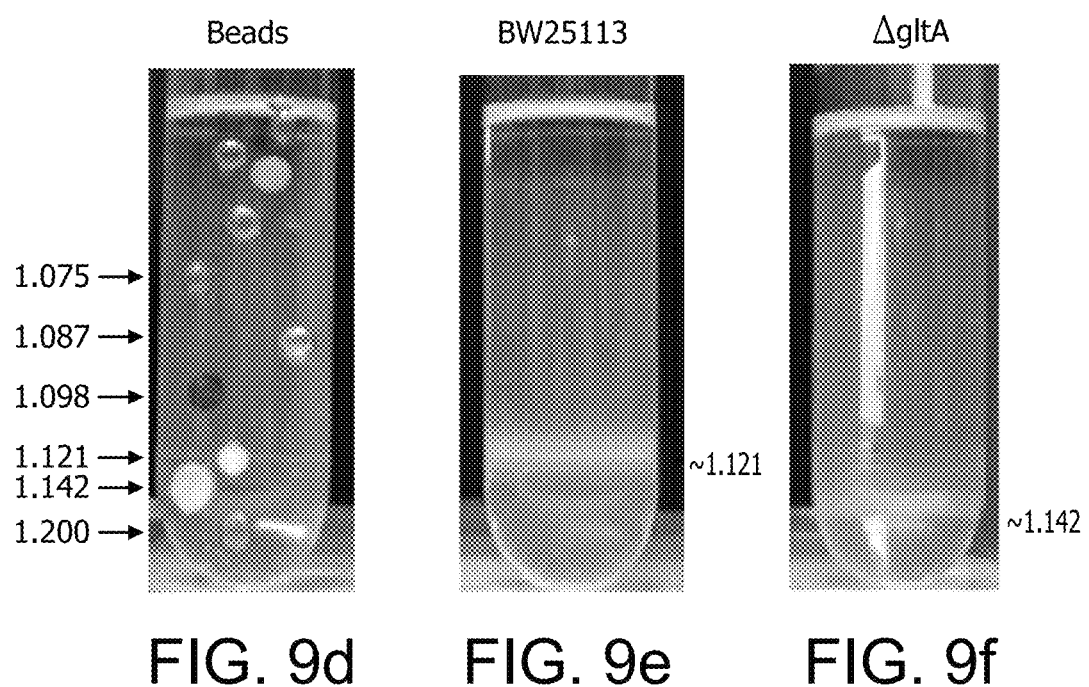
FIG. 9e shows a band (approximately 1.121 g/mL) formed from the density gradient separation of inclusion bodies from control strain BW25113.
FIG. 9f shows a band (approximately 1.142 g/mL) formed from the density gradient separation of inclusion bodies from a strain having a ΔgltA modification.

It was also determined whether or not additional deletions, especially deletions neighboring the gltA deletion, would also confer increased buoyant density to induced cells and their corresponding inclusion bodies. The JW0710 strain (Baba et al., supra) containing the gltA deletion and the JW0709 strain containing the adjacent ybgD deletion from the Keio collection were transformed with the peptide production plasmid. Duplicates of these two cultures and the control were grown and induced as describe above. The whole cells (FIGS. 9b and 9c) and the crude inclusion bodies (FIGS. 9e and 9f) from these cultures were analyzed by density gradient centrifugation. A set of beads were used as density standards to determine the buoyant density values (FIGS. 9a and 9d). The buoyant density of the control cells had a wider distribution of about 1.08-1.09 (FIG. 9b). The buoyant density of the ΔgltA cells was estimated to be about 1.115 (FIG. 9c). The buoyant density of the inclusion body from the control was approximately 1.121 (FIG. 9e) and the buoyant density of the inclusion body from the ΔgltA cells was approximately 1.142. Results confirmed that the cells and the inclusion bodies from the ΔgltA strain showed increased buoyant density than the control strain, whereas the cells and the inclusion bodies from the ΔybgD strain showed similar buoyant densities as the control strain and the corresponding IBs.

The induced cultures were also loaded on SDS-PAGE gel and analyzed. Similar amounts of peptide were produced from all these strains. The results show that more dense inclusion bodies (not more inclusion body) were produced in the ΔgltA strain and that this was indeed due to the deletion of the gltA gene.

What is claimed is:

1. A method comprising:
   a) providing a population of recombinant microbial cells, the recombinant microbial cells in the population comprising;
      i) at least one introduced genetic modification that increases expression of GlyS, GlyQ, YsaB, or a combination thereof; and
      ii) a chimeric genetic construct encoding a polypeptide of interest, which polypeptide is not GlyS, GlyQ, or YsaB;
   b) growing the recombinant microbial cells under suitable conditions whereby the polypeptide of interest is produced and accumulates within the recombinant microbial cells ;
   c) fractionating the population of recombinant microbial cells grown in (b) by a density gradient centrifugation;
   d) isolating a subpopulation of the recombinant microbial cells from a fraction having a higher buoyant density; and
   e) optionally repeating steps (a) through (d).

2. The method of claim 1 wherein the polypeptide of interest accumulates within the recombinant microbial cells in the form of at least one inclusion body.

3. The method of claim 1 wherein polypeptide of interest is 14 to 600 amino acids in length.

4. The method of claim 3 wherein the polypeptide of interest is expressed as a fusion protein.

5. The method of claim 4 wherein the fusion protein comprises the general structure:
   IBT-CL-POI
   or
   POI-CL-IBT
   wherein;
   IBT =at least one inclusion body tag;
   CL =at least one cleavable peptide linker; and POI=the polypeptide of interest.

6. The method of claim 1 wherein the recombinant microbial cells are bacterial cells, yeast cells or fungal cells.

7. The method of claim 6 wherein the recombinant microbial cells are selected from the group consisting of *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

8. The method of claim 7 wherein the recombinant microbial cells are *Escherichia coli*.

9. The method of claim 1 further comprising introducing at least one genetic modification that decreases or disrupts expression of GltA.

10. The method of claim 1 wherein the isolated subpopulation of cells of step (d) has a buoyant density of at least 1.1 g/mL.

11. A method comprising:
    a) providing a population of recombinant microbial cells, the recombinant microbial cells in the population comprising;
       i) at least one introduced genetic modification that decreases or disrupts expression of GltA; and
       ii) a chimeric genetic construct encoding a polypeptide of interest;
    b) growing the recombinant microbial cells under suitable conditions whereby the polypeptide of interest is produced and accumulates within the recombinant microbial cells ;
    c) fractionating the population of recombinant microbial cells grown in (b) by a density gradient centrifugation;
    d) isolating a subpopulation of the recombinant microbial cells from a fraction having a higher buoyant density; and
    e) optionally repeating steps (a) through (d).

12. The method of claim 11 wherein the polypeptide of interest accumulates within the recombinant microbial cells in the form of at least one inclusion body.

13. The method of claim 11 wherein the at least one introduced genetic modification is a knockout mutation.

14. The method of claim 11 wherein polypeptide of interest is 14 to 600 amino acids in length.

15. The method of claim 11 wherein the polypeptide of interest is expressed as a fusion protein.

16. The method of claim 15 wherein the fusion protein comprises the general structure:
    IBT-CL-POI
    or
    POI-CL-IBT
    wherein;
    IBT=at least one inclusion body tag;
    CL=at least one cleavable peptide linker; and POI=the polypeptide of interest.

17. The method of claim 11 wherein the recombinant microbial cells are bacterial cells, yeast cells or fungal cells.

18. The method of claim 17 wherein the recombinant microbial cells are selected from the group consisting of *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

19. The method of claim 18 wherein the recombinant microbial cells are *Escherichia coli*.

20. The method of claim 11 further comprising introducing at least one genetic modification that increases expression of GlyS, GlyQ, YsaB, or a combination thereof.

21. The method of claim 11 wherein the isolated subpopulation of cells of step (d) has a buoyant density of at least 1.1 g/mL.

* * * * *